(12) United States Patent
Robertson et al.

(10) Patent No.: US 7,368,632 B2
(45) Date of Patent: May 6, 2008

(54) PLANT STRESS TOLERANCE GENES, AND USES THEREFOR

(75) Inventors: Albert James Robertson, Saskatoon (CA); Lawrence Victor Gusta, Saskatoon (CA); Guohai Wu, Saskatoon (CA)

(73) Assignee: University of Saskatchewan, Saskatoon, Saskatchewan (CA)

( * ) Notice: Subject to any disclaimer, the term of this patent is extended or adjusted under 35 U.S.C. 154(b) by 0 days.

(21) Appl. No.: 10/534,744

(22) PCT Filed: Nov. 14, 2003

(86) PCT No.: PCT/CA03/01754

§ 371 (c)(1),
(2), (4) Date: Oct. 17, 2005

(87) PCT Pub. No.: WO2004/044207

PCT Pub. Date: May 27, 2004

(65) Prior Publication Data

US 2006/0122375 A1 Jun. 8, 2006

Related U.S. Application Data

(60) Provisional application No. 60/426,012, filed on Nov. 14, 2002.

(51) Int. Cl.
*A01H 5/00* (2006.01)
*C12N 15/82* (2006.01)
*C12N 15/87* (2006.01)
*C12N 5/14* (2006.01)
*C07H 21/00* (2006.01)

(52) U.S. Cl. ............... 800/295; 435/320.1; 435/419; 435/468; 800/287; 800/289; 536/23.6

(58) Field of Classification Search .................. None
See application file for complete search history.

(56) References Cited

FOREIGN PATENT DOCUMENTS

WO WO 00/08187 2/2000

OTHER PUBLICATIONS

Wu et al. (NCBI, GenBank Sequence Accession No. AY057933, Published Oct. 31, 2001).*
Liu et al. (The Plant Cell, 10:1391-1406, Aug. 1998).*
Moloney et al. (Plant Cell Reports, 8:238-242, 1989).*
Wells, (Biochemistry 29:8509-8517; 1990).*
Ngo et al., (The Protein Folding Problem and Tertiary Structure Prediction, K. Merz., and S. Le Grand (eds.) pp. 492-495,1994).*
Keskin et al. (Protein Science, 13:1043-1055, 2004).*
Thornton et al. (Nature structural Biology, structural genomics supplement, Nov. 2000).*
Guo et al. (PNAS, 101: 9205-9210, 2004).*
Buell et al. (NCBI, GenBank Sequence Accession No. Q8s7U3, Published 2002).*
Guy, Charles L.: "Cold Acclimation and Freezing Stress Tolerance: Role of Protein Metabolism", 1990, Annu, Rev. Plant Physiol. Plant Mol. Biol. 41: 187-223.
Robertson et al.: "Protein Synthesis in Bromegrass (*Bromus inermis* Leyss) Cultured Cells during the Induction of Frost Tolerance by Abscisic Acid or Low Temperature", 1987, Plant Physiol. vol. 84: 1331-1337.
Robertson et al.: "Identification of Proteins Correlated with Increased Freezing Tolerance in Bromegrass (*Bromus inermis* Leyss. cv Manchar) Cell Cultures", 1988, Plant Physiol. vol. 86: 344-347.
Robertson et al.: "Abscisic acid-induced heat tolerance in *Bromus inermis* Leyss cell-suspension cultures: Heat-stable, abscisic acid-responsive polypeptides in combination with sucrose confer enhanced thermostability", 1994, Plant Physiol. vol. 105: 181-190.
Ishikawa et al.: "Comparison of viability tests for assessing cross-adaptation to freezing, heat and salt stresses induced by abscisic acid in bromegrass (*Bromus inermis* Leyss) suspension cultured cells", 1995, Plant Science vol. 107: 83-93.
Zhang, H-X and Blumwald, E.: "Transgenic salt-tolerant tomato plants accumulate salt in foliage but not in fruit", 2001, Nature Biotech, vol. 19: 765-768.
Jaglo et al.: "Components of the Arabidopsis C-Repeat/Dehydration-Responsive Element Binding Factor Cold-Responsive Pathway Are Conserved in *Brassica napus* and Other Plant Species", 2001, Plant Physiol, vol. 127: 910-917.
Gilmour, S.J. et al.: "Low temperature regulation of the Arabidopsis CBF family of AP2 transcriptional activators as an early step in cold-induced COR gene expression", 1998, The Plant Journal, vol. 16(4): 433-442.
Gaxiola, R.A. et al.: "Drought- and salt-tolerant plants result from overexpression of the AVP1 $H^+$-pump", 2001, Proc. Natl. Acad. Sci. USA, vol. 98, No. 20: 11444-11449.
Lee, S.P. and T.H.H. Chen: "Molecular Cloning of Abscisic Acid-Responsive mRNAs Expressed during the Induction of Freezing Tolerance in Bromegrass (*Bromus inermis* Leyss) Suspension Culture", 1993. Plant Physiol. vol. 101: 1089-1096.

(Continued)

*Primary Examiner*—David H. Kruse
*Assistant Examiner*—Vinod Kumar

(57) ABSTRACT

Plant stresses such as pest infestations, disease, drought, flood, and excessive temperatures can lead to significant losses of crops each year. There is a continuing need to develop novel plant varieties that are less susceptible to damage or loss by such stresses. The present invention provides for the isolation, characterization and use of an entirely novel class of plant genes, generally designated ROB5. Transgenic plants expressing ROB5 can show a dramatic improvement in their capacity to tolerate a variety of stress conditions. Moreover, ROB5 expression can further lead to marked increases in plant growth rates and plant vigor. The present invention encompasses all such ROB5 genes and peptides encoded thereby, plants expressing corresponding ROB5 constructs, and plant products thereof.

16 Claims, 44 Drawing Sheets

OTHER PUBLICATIONS

Gusta L. et al.: "Genetic engineering of cultivated plants for enhanced abiotic stress tolerance"; Oct. 1, 2002, Kluwer Academic, NY XP008029213. pp. 237-248.

Database EM_PL !Online!: Apr. 26, 2002; Buell C.R. et al.: "Oryza satiza chromosome 3 BACOSJNBa0091P11 genomic sequence, complete sequence" Database accession No. AC073556 XP 002275352, abstract.

Robertson et al.: "The effect of prolonged abscisic acid treatment on the growth, freezing tolerance and protein patterns of *Bromus inermis* (Leyss) cell suspensions cultured at either 3 degrees or 25 degrees C", 1995, Plant Physiol. vol. 145, No. 1-2: 137-142.

In Plant Cold Hardiness: Genetic Regulation and Genetic Engineering Eds: P.H. Li and E.T. Palva, Kluwer Academic/Plenum Publishers, pp. 237-248.

\* cited by examiner

```
GTCGCAATCCATTCAGAGCACGCAAAGCACGCGAGCAGCTGCGCATTCTAGATTCTAGCTCGGGACGATCAGATCA   76

ATGGCGGTCATGTCGCGGTCCAGGAGGCTGGCGGCGCCCGCGCTGCTGGTGCTGCTAGCGCTGGCGGCCGTGGCCGTG  154
 M  A  V  M  S  R  S  R  R  L  A  A  P  A  L  L  V  L  L  A  L  A  A  V  A  V   (26)

GCGGAGACGACGCTGGACGGCGCGGAGGTGGCGCCGGGCAAGGAGGAGTCGTCGTGGGCGGGGTGGGCCAAGGACAAG  232
 A  E  T  T  L  D  G  A  E  V  A  P  G  K  E  S  S  W  A  G  W  A  K  D  K      (52)

GTCTCGGAAGGCCTCGGCCTGGACAAGATCTCCGAGGGGCTCGGGCTCAAGCACCACGCCGACGAGGAGGAGGCCGCG  310
 V  S  E  G  L  G  L  D  K  I  S  E  G  L  G  L  K  H  H  A  D  E  E  A  A       (78)

CGCAAGGCCGGACACACCGTCAAGTCCGCCCGCGAGACCGCCCAGCACGCCGCCTCCGAGACGGGGAGGCAGGCGAGC  388
 R  K  A  G  H  T  V  K  S  A  R  E  T  A  Q  H  A  A  S  E  T  G  R  Q  A  S   (104)

GGCAAGGTGGGGGACGCCAAGGAGGCCGCGGAGCAGGCGGCGACCGGGGCGGCCAACAAGGCGGGGCAGGCCAAAGAC  466
 G  K  V  G  D  A  K  E  A  A  E  Q  A  A  T  G  A  A  N  K  A  G  Q  A  K  D   (130)

AAGGCGGCGGAGACGGTGAAGGGCACGGCCGGCGAGGCGTCCAAGAAGGCGGAGCAGGCCAAGCACAAGACCAAGGAG  544
 K  A  A  E  T  V  K  G  T  A  G  E  A  S  K  K  A  E  Q  A  K  H  K  T  K  E   (156)

GCCGCGGAGGCCGCCGCCAAGACGGGCGCCGAGACGCACGAGCGGTCGAAGCAGGGCAAGGCCAAGGTGGAGGAGATG  622
 A  A  E  A  A  A  K  T  G  A  E  T  H  E  R  S  K  Q  G  K  A  K  V  E  E  M   (182)

GCCAGGGAGTGGTACGAGAGAGCCAAGCACACGGCCGGGGAGGGGTACGAGACGCTGAAGCAAACCAAGGACGCGGCT  700
 A  R  E  W  Y  E  R  A  K  H  T  A  G  E  G  Y  E  T  L  K  Q  T  K  D  A  A   (208)

GCGGAGAAGGCAGCGGCAGCCAAGGACGCCGCCACGAACAAGGCCGGTGCCGCCACGCAGACGGCCGCGGAGAAGGCA  778
 A  E  K  A  A  A  A  K  D  A  A  T  N  K  A  G  A  A  T  Q  T  A  A  E  K  A   (234)

GCGGCAGCCAAGGACACCGCCGCCGGTAAGGCCAAGGCTGCCGAAGGACGCTGCGTGGGAGGAGACAGGCTCTGCCAAG  856
 A  A  A  K  D  T  A  A  G  K  A  K  A  A  K  D  A  A  W  E  E  T  G  S  A  K   (260)

GACGCCACATGGCAGGCGCAGGAGAAGCTGAAGCAATACAACGACGCCGCTTCGGAGAAGGCCGCGGCAGCCAAGGAC  934
 D  A  T  W  Q  A  Q  E  K  L  K  Q  Y  N  D  A  A  S  E  K  A  A  A  A  K  D   (286)

GCCGACGCTGAGAAGGCCGCGGCAGCCAAGGACGCGGCGTGGAAGAACGCCGAGGCGGCCAAGGGAACGGTCGGAGAG 1012
 A  D  A  E  K  A  A  A  A  K  D  A  A  W  K  N  A  E  A  A  K  G  T  V  G  E   (312)

AAGGCACGGGCGGCCAAGGACGCCACGTTGGAGAAGACCGAGTCCGCGAAGGACGCCGCTTGGAGACGGCGGAGGCG  1090
 K  A  G  A  A  K  D  A  T  L  E  K  T  E  S  A  K  D  A  A  W  E  T  A  E  A   (338)

GCCAAGGGCAAGGCTAACGAGGGGTACGAGAAGGTGAAGGAGAAGGACGCGACCAAGGAAAAGCTCGGCGAGGTGAAG 1168
 A  K  G  K  A  N  E  G  Y  E  K  V  K  E  K  D  A  T  K  E  K  L  G  E  V  K   (364)

GACAAGGTCACCGGCGCAGCATCCGACGGCAAGGCGAAGAAGCNCGCAATGGCGACGAGCTGTGAATGAACACGATC  1246
 D  K  V  T  G  A  A  S  D  G  K  A  K  K  X  R  N  G  D  E  L                  (385)

CATCCGCATTTCTTGCCATAGTTCCTTCTTCCATGAATGTTTTCAGTGTTCTTCGAGCTAGTTTTTTTTATGTTGTTC 1324
CTTTTGTACAATAACGTGTCCCATATGTATTGAACCATGCACGATCAAACAAGTTTCTTTCTATAAAAAAAAAAAAAA 1402
AAAAAAAAAAAAAAAAAAA                                                             1420
```

FIG. 1

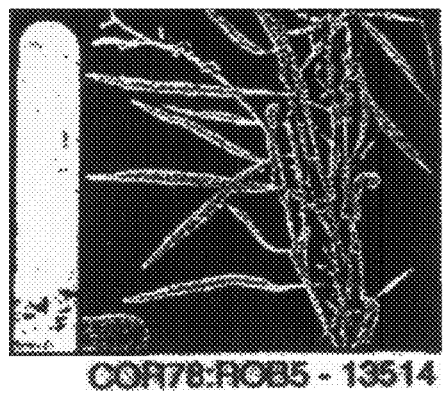
FIG. 7C
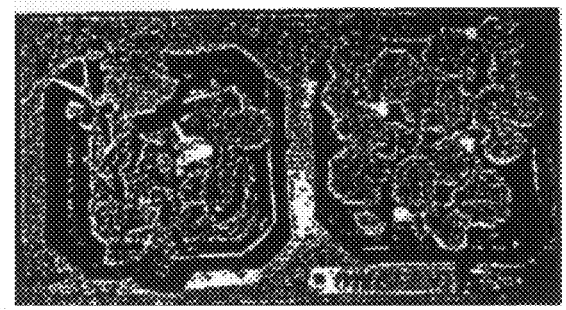
FIG. 7D

|  | P |
|---|---|
| C | ++ |
| 35S:ROB5 | |
| 13645 | ++ |
| 13646 | 0 |
| 13637 | 0 |
| COR78:ROB5 | |
| 13650 | 0 |
| 13665 | + |
| 13955 | ++ |

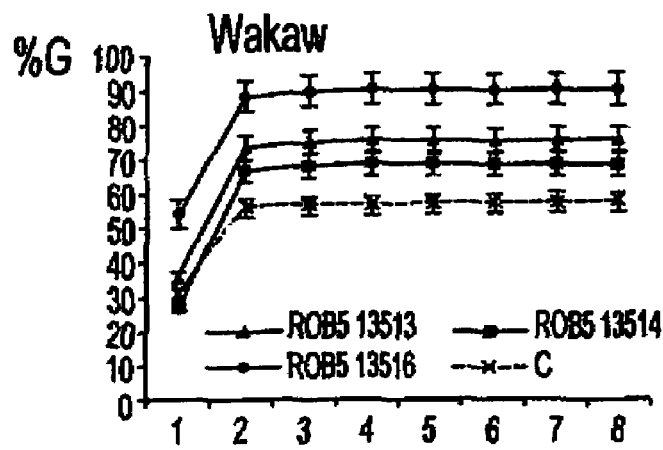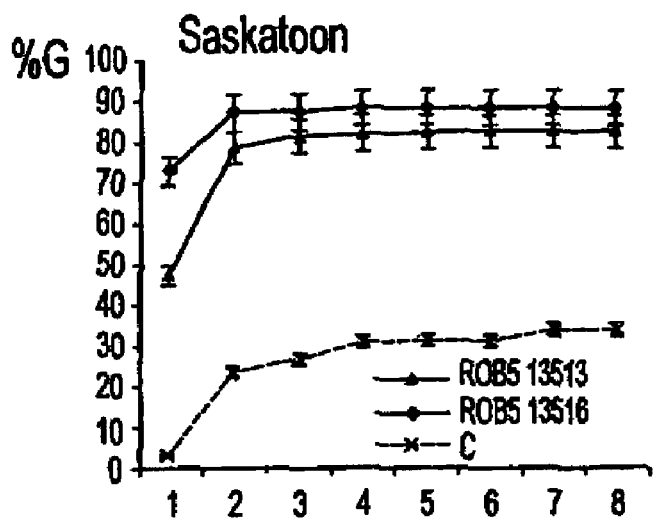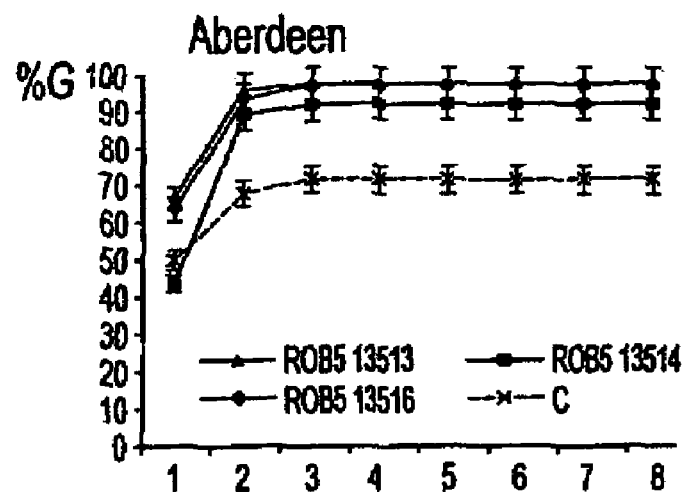
FIG. 37A

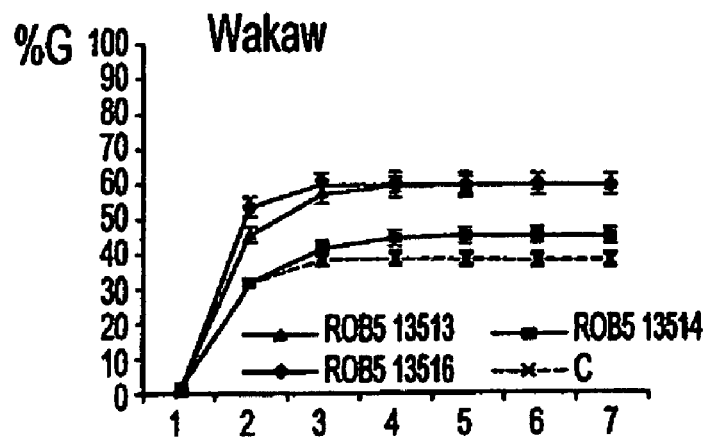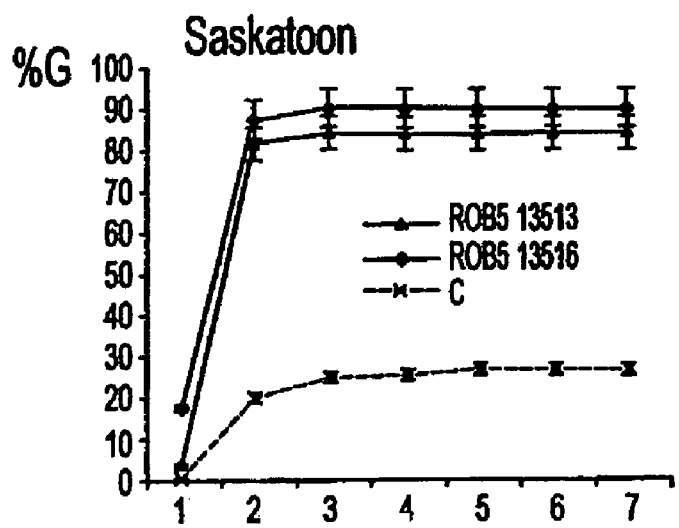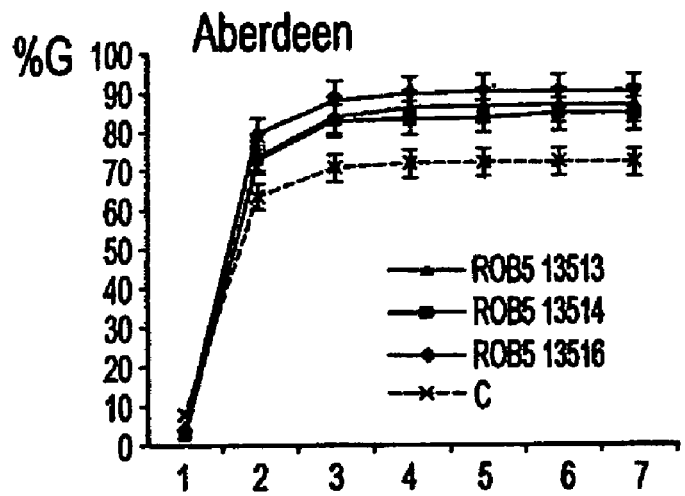
FIG. 37B

SEQUENCE LISTING

<160> NUMBER OF SEQ ID NOS: 4

<210> SEQ ID NO 1
<211> LENGTH: 1420
<212> TYPE: DNA
<213> ORGANISM: Bromus
<220> FEATURE:
<221> NAME/KEY: misc_feature
<222> LOCATION: (1212)..(1212)
<223> OTHER INFORMATION: n = a, c, g, or t
<220> FEATURE:
<221> NAME/KEY: CDS
<222> LOCATION: (77)..(1231)
<223> OTHER INFORMATION:

<400> SEQUENCE: 1

```
gtcgcaatcc attcagagca cgcaaagcac gcgagcagct gcgcattcta gattctagct      60
cgggacgatc agatca atg gcg gtc atg tcg cgg tcc agg agg ctg gcg gcg     112
                  Met Ala Val Met Ser Arg Ser Arg Arg Leu Ala Ala
                    1               5                  10 ccc gcg ctg ctg gtg ctg cta gcg ctg gcg gcc gtg gcc gtg gcg gag      160
Pro Ala Leu Leu Val Leu Leu Ala Leu Ala Ala Val Ala Val Ala Glu
         15                  20                  25 acg acg ctg gac ggc gcg gag gtg gcg ccg ggc aag gag gag tcg tcg      208
Thr Thr Leu Asp Gly Ala Glu Val Ala Pro Gly Lys Glu Glu Ser Ser
     30                  35                  40 tgg gcg ggg tgg gcc aag gac aag gtc tcg gaa ggc ctc ggc ctg gac      256
Trp Ala Gly Trp Ala Lys Asp Lys Val Ser Glu Gly Leu Gly Leu Asp
 45                  50                  55                  60 aag atc tcc gag ggg ctc ggg ctc aag cac cac gcc gac gag gag gag      304
Lys Ile Ser Glu Gly Leu Gly Leu Lys His His Ala Asp Glu Glu Glu
                 65                  70                  75 gcc gcg cgc aag gcc gga cac acc gtc aag tcc gcc cgc gag acc gcc      352
Ala Ala Arg Lys Ala Gly His Thr Val Lys Ser Ala Arg Glu Thr Ala
             80                  85                  90 cag cac gcc gcc tcc gag acg ggg agg cag gcg agc ggc aag gtg ggg      400
Gln His Ala Ala Ser Glu Thr Gly Arg Gln Ala Ser Gly Lys Val Gly
         95                 100                 105 gac gcc aag gag gcc gcg gag cag gcg gcg acc ggg gcg gcc aac aag      448
Asp Ala Lys Glu Ala Ala Glu Gln Ala Ala Thr Gly Ala Ala Asn Lys
    110                 115                 120 gcg ggg cag gcc aaa gac aag gcg gcg gag acg gtg aag ggc acg gcc      496
Ala Gly Gln Ala Lys Asp Lys Ala Ala Glu Thr Val Lys Gly Thr Ala
125                 130                 135                 140 ggc gag gcg tcc aag aag gcg gag cag gcc aag cac aag acc aag gag      544
Gly Glu Ala Ser Lys Lys Ala Glu Gln Ala Lys His Lys Thr Lys Glu
                145                 150                 155
```

| gcc gcg gag gcg gcc gcc aag acg ggc gcc gag acg cac gag cgg tcg | 592 |
| Ala Ala Glu Ala Ala Ala Lys Thr Gly Ala Glu Thr His Glu Arg Ser | |
|         160               165             170 | |

```
gcc gcg gag gcg gcc gcc aag acg ggc gcc gag acg cac gag cgg tcg       592
Ala Ala Glu Ala Ala Ala Lys Thr Gly Ala Glu Thr His Glu Arg Ser
        160                 165                 170 aag cag ggc aag gcc aag gtg gag gag atg gcc agg gag tgg tac gag       640
Lys Gln Gly Lys Ala Lys Val Glu Glu Met Ala Arg Glu Trp Tyr Glu
    175                 180                 185 aga gcc aag cac acg gcc ggg gag ggg tac gag acg ctg aag caa acc       688
Arg Ala Lys His Thr Ala Gly Glu Gly Tyr Glu Thr Leu Lys Gln Thr
190                 195                 200 aag gac gcg gct gcg gag aag gca gcg gca gcc aag gac gcc gcc acg       736
Lys Asp Ala Ala Ala Glu Lys Ala Ala Ala Lys Asp Ala Ala Thr
205                 210                 215                 220 aac aag gcc ggt gcc gcc acg cag acg gcc gcg gag aag gca gcg gca       784
Asn Lys Ala Gly Ala Ala Thr Gln Thr Ala Ala Glu Lys Ala Ala Ala
                225                 230                 235 gcc aag gac acc gcc gcc ggt aag gcc aag gct gcg aag gac gct gcg       832
Ala Lys Asp Thr Ala Ala Gly Lys Ala Lys Ala Ala Lys Asp Ala Ala
                240                 245                 250 tgg gag gag aca ggc tct gcc aag gac gcc aca tgg cag gcg cag gag       880
Trp Glu Glu Thr Gly Ser Ala Lys Asp Ala Thr Trp Gln Ala Gln Glu
                255                 260                 265 aag ctg aag caa tac aac gac gcc gct tcg gag aag gcc gcg gca gcc       928
Lys Leu Lys Gln Tyr Asn Asp Ala Ala Ser Glu Lys Ala Ala Ala Ala
                270                 275                 280 aag gac gcc gac gct gag aag gcc gcg gca gcc aag gac gcg gcg tgg       976
Lys Asp Ala Asp Ala Glu Lys Ala Ala Ala Lys Asp Ala Ala Trp
285                 290                 295                 300 aag aac gcc gag gcg gcc aag gga acg gtc gga gag aag gca ggg gcg      1024
Lys Asn Ala Glu Ala Ala Lys Gly Thr Val Gly Glu Lys Ala Gly Ala
                305                 310                 315 gcc aag gac gcc acg ttg gag aag acc gag tcc gcg aag gac gcc gct      1072
Ala Lys Asp Ala Thr Leu Glu Lys Thr Glu Ser Ala Lys Asp Ala Ala
                320                 325                 330 tgg gag acg gcg gag gcg gcc aag ggc aag gct aac gag ggg tac gag      1120
Trp Glu Thr Ala Glu Ala Ala Lys Gly Lys Ala Asn Glu Gly Tyr Glu
                335                 340                 345 aag gtg aag gag aag gac gcg acc aag gaa aag ctc ggc gag gtg aag      1168
Lys Val Lys Glu Lys Asp Ala Thr Lys Glu Lys Leu Gly Glu Val Lys
350                 355                 360 gac aag gtc acc ggc gca gca tcc gac ggc aag gcg aag aag cnc cgc      1216
Asp Lys Val Thr Gly Ala Ala Ser Asp Gly Lys Ala Lys Lys Xaa Arg
365                 370                 375                 380 aat ggc gac gag ctg tgaatgaaca cgatccatcc gcatttcttg ccatagttcc      1271
Asn Gly Asp Glu Leu
                385 ttcttccatg aatgttttca gtgttcttcg agctagtttt ttttatgttg ttcctttgt    1331 acaataacgt gtcccatatg tattgaacca tgcacgatca acaagtttc tttctataaa    1391 aaaaaaaaaa aaaaaaaaa aaaaaaaa                                        1420

<210> SEQ ID NO 2
<211> LENGTH: 385
<212> TYPE: PRT
<213> ORGANISM: Bromus
<220> FEATURE:
<221> NAME/KEY: misc_feature
<222> LOCATION: (379)..(379)
<223> OTHER INFORMATION: The 'Xaa' at location 379 stands for His, Arg,
      Pro, or Leu.

<400> SEQUENCE: 2
```

```
Met Ala Val Met Ser Arg Ser Arg Arg Leu Ala Ala Pro Ala Leu Leu
1               5                   10                  15

Val Leu Leu Ala Leu Ala Ala Val Ala Val Ala Glu Thr Thr Leu Asp
            20                  25                  30

Gly Ala Glu Val Ala Pro Gly Lys Glu Ser Ser Trp Ala Gly Trp
        35                  40                  45

Ala Lys Asp Lys Val Ser Glu Gly Leu Gly Leu Asp Lys Ile Ser Glu
50                  55                  60

Gly Leu Gly Leu Lys His His Ala Asp Glu Glu Ala Ala Arg Lys
65              70                  75                  80

Ala Gly His Thr Val Lys Ser Ala Arg Glu Thr Ala Gln His Ala Ala
                85                  90                  95

Ser Glu Thr Gly Arg Gln Ala Ser Gly Lys Val Gly Asp Ala Lys Glu
            100                 105                 110

Ala Ala Glu Gln Ala Ala Thr Gly Ala Ala Asn Lys Ala Gly Gln Ala
            115                 120                 125

Lys Asp Lys Ala Ala Glu Thr Val Lys Gly Thr Ala Gly Glu Ala Ser
        130                 135                 140

Lys Lys Ala Glu Gln Ala Lys His Lys Thr Lys Glu Ala Ala Glu Ala
145                 150                 155                 160

Ala Ala Lys Thr Gly Ala Glu Thr His Glu Arg Ser Lys Gln Gly Lys
                165                 170                 175

Ala Lys Val Glu Glu Met Ala Arg Glu Trp Tyr Glu Arg Ala Lys His
            180                 185                 190

Thr Ala Gly Glu Gly Tyr Glu Thr Leu Lys Gln Thr Lys Asp Ala Ala
        195                 200                 205

Ala Glu Lys Ala Ala Ala Lys Asp Ala Ala Thr Asn Lys Ala Gly
    210                 215                 220

Ala Ala Thr Gln Thr Ala Ala Glu Lys Ala Ala Ala Lys Asp Thr
225                 230                 235                 240

Ala Ala Gly Lys Ala Lys Ala Lys Asp Ala Ala Trp Glu Glu Thr
                245                 250                 255

Gly Ser Ala Lys Asp Ala Thr Trp Gln Ala Gln Glu Lys Leu Lys Gln
        260                 265                 270

Tyr Asn Asp Ala Ala Ser Glu Lys Ala Ala Ala Lys Asp Ala Asp
            275                 280                 285

Ala Glu Lys Ala Ala Ala Lys Asp Ala Ala Trp Lys Asn Ala Glu
    290                 295                 300

Ala Ala Lys Gly Thr Val Gly Glu Lys Ala Gly Ala Ala Lys Asp Ala
305                 310                 315                 320

Thr Leu Glu Lys Thr Glu Ser Ala Lys Asp Ala Ala Trp Glu Thr Ala
            325                 330                 335

Glu Ala Ala Lys Gly Lys Ala Asn Glu Gly Tyr Glu Lys Val Lys Glu
        340                 345                 350

Lys Asp Ala Thr Lys Glu Lys Leu Gly Glu Val Lys Asp Lys Val Thr
            355                 360                 365

Gly Ala Ala Ser Asp Gly Lys Ala Lys Lys Xaa Arg Asn Gly Asp Glu
        370                 375                 380

Leu
385

<210> SEQ ID NO 3
<211> LENGTH: 15
<212> TYPE: PRT
```

```
<213> ORGANISM: Bromus

<400> SEQUENCE: 3

Glu Thr Thr Leu Asp Gly Ala Glu Val Ala Pro Gly Lys Glu Glu
1               5                   10                  15

<210> SEQ ID NO 4
<211> LENGTH: 6
<212> TYPE: PRT
<213> ORGANISM: Bromus

<400> SEQUENCE: 4

Lys Ala Ala Ala Ala Lys
1               5
```

PLANT STRESS TOLERANCE GENES, AND USES THEREFOR

CROSS-REFERENCE TO RELATED APPLICATIONS

This application is the national phase of PCT international application Serial No. PCT/CA03/01754 filed Nov. 14, 2003, and claims the priority right of U.S. patent application Ser. No. 60/426,012 filed Nov. 14, 2002 by applicants herein.

FIELD OF THE INVENTION

The present invention relates to the field of plant stress tolerance, and means to alter plant metabolism to improve plant resistance to, for example, drought, heat, cold, pest infection, disease etc. The invention further relates to processes for generating modified plants that exhibit increased stress tolerance, to the plants generated by such processes, and their products.

BACKGROUND TO THE INVENTION

Pest infestation, disease, and adverse environmental conditions can result in severe crop damage or loss. In the Western world, crop devastation can translate into financial ruin for those involved in the agricultural industry. In many other parts of the world the results may be even more drastic including widespread malnutrition and famine. There exists a continuing need to develop plants and crops that exhibit improved resistance to plant stresses, thereby increasing crop yields in adverse conditions and reducing the risk of crop failure. For example, plants with increased tolerance to drought, heat and higher salt conditions may open the possibility of farming in semi-desert climates, where agriculture was previously non-viable. Conversely, the development of novel crops with improved tolerance to cold or freezing temperatures may significantly prolong the growing season in regions with colder climates.

A number of plant genes are known to show increased levels of expression when plants are exposed to stress. Examples include those genes involved in metabolic pathways influenced by abscisic acid; a naturally occurring plant 'growth hormone' that can promote several plant functions including, for example, leaf aging, apical dominance, and seed or bud dormancy. The levels of abscisic acid are known to increase in plants under stress. Moreover, exogenous application of abscisic acid to plants is known to increase tolerance to abiotic stresses including chilling, cold, heat, salt and dehydration (Guy (1990) Annu. Rev. Plant Physiol. Plant Mol. Biol. 41: 187-223.)

Previously, the inventors for the present invention have shown that the application of 75 µM abscisic acid to cell suspension cultures of *Bromus inermis* can result in increased freezing tolerance, with a corresponding increase and de novo synthesis of a specific set of unknown proteins (Robertson et al. 1987 Plant Physiol. 84: 1331-1337; Robertson et al. 1988 Plant Physiol. 86: 344-347). Additional studies have shown that abscisic acid treated bromegrass cells can exhibit an increased tolerance to heat (Robertson et al. 1994 Plant Physiol. 105: 181-190), and salt (Ishikawa et al. 1995 Plant Science 107: 83-93).

Studies using comparative 2-dimensional gel electrophoresis have indicated that a large number of unknown proteins may be upregulated in response to stress (Robertson et al. 1994). Some of these proteins in the 20-30 kDa size range are cross-reactive with an anti-dehydrin antibody and an antibody (Wcs120) to cold-responsive winter wheat protein. Another group of proteins in the 43-45 kDa range were differentiated from those in the 20-30 kDa range by a lack of cross-reactivity with Wcs120 and poor cross-reactivity with the anti-dehydrin antibody. Moreover, some of the proteins in the 43-45 kDa range were found by microsequencing to have some degree of homology within the initial amino-terminal amino acids.

Despite considerable efforts to engineer genetically modified crops with increased stress tolerance, to date there are little or no such crops on the commercial market. Performance Plants Inc. have reported a drought tolerant canola plant with modified stomatal function that shows 10% increased yield over controls under drought conditions. Transgenic tomato plants (Zhang, H-X and Blumwald, E. 2001. Nature Biotech, 19: 765-768) with enhanced salinity were produced by overexpressing a vacuolar $Na^+/H^+$ antiport protein. The freezing tolerance of non-acclimated and cold acclimated canola seedlings can be increased by over expressing CBF (C-repeat/dehydration responsive element binding factor) (Jaglo et al. 2001. Plant Physiol, 103(4): 1047-1053). This work was based on the observation that small increases in freezing tolerance occurred in *Arabidopsis* seedlings constitutively expressing CBF genes (Gilmour, S. J. et al. 1998. Plant J., 16: 433-442.) Enhanced tolerance to both salt and drought stresses has been identified in transgenic *Arabidopsis* plants overexpressing vacuolar $H^+$-pyrophosphatase (Gaxiola, R. A. et al. 2001. Proc. Natl. Acad. Sci. USA, 25: 11444-11449). Most transgenic plant work in abiotic stress has been done with *Arabidopsis thaliana* a non-economic model plant system.

The future prospects of engineering novel plants with an increased capacity to tolerate environmental insults will depend on the availability of critical stress tolerance controlling genes, and knowledge of their functional regulatory properties; The inventors for the present application, and others, have endeavored to decipher the mechanisms of plant stress tolerance in the hope of developing an understanding of the biochemical pathways involved. Nonetheless, the characterization of the genes and proteins involved in plant stress responses presents a number of significant challenges.

There remains a continuing need to develop a better understanding of plant stress responses, so that corresponding methods can be developed to confer advantageous properties to plants. This need extends to the production of crops with an increased capacity to resist damage by both infestation and disease. In addition, there remains a need to develop crops that exhibit resistance to damage by adverse climatic conditions such as excessive temperatures, drought, flood, low levels of nutrients, or high levels of toxins. Even incremental gains in plant stress tolerance may have a significant economic impact in stablizing the quality and supply of grain, oilseed and horticulture. Enhancement of germination, growth and flowering are extremely important in regions that have a short or otherwise difficult growing season.

SUMMARY OF THE INVENTION

It is an object of the present invention, at least in preferred forms, to provide a nucleotide sequence that when exogenously expressed in a plant, the stress tolerance and/or the growth of the plant is increased compared to an unmodified plant.

It is another object of the present invention, at least in preferred forms, to provide a transgenic plant that exhibits altered stress tolerance and/or altered growth compared to an unmodified plant.

It is another object of the present invention to provide a method of modifying a plant, to alter the stress tolerance and/or the growth potential of the plant.

The inventors have succeeded in isolating and characterizing a plant gene that is upregulated in response to the presence of abscisic acid. Moreover, the inventors have found that exogenous expression of the gene, in plants results in an unexpectedly dramatic increase in stress tolerance to a large range of stress conditions. Even more unexpected was the effect of exogenous expression upon plant growth and vigor, which was significantly enhanced in comparison with unmodified plants. The inventors have further determined that corresponding genes are expressed in multiple plant species.

In a first aspect the present invention provides for an isolated nucleotide sequence, characterized in that the sequence encodes a ROB5 protein, or a fragment thereof.

In another aspect, the invention provides for an isolated nucleotide sequence characterized in that the sequence is selected from:

a) a ROB5 gene as shown in SEQ ID NO: 1, or a complement thereof;

b) a nucleotide sequence encoding a peptide with at least 50% identity to a peptide encoded by the nucleotide sequence of a), or a complement thereof; wherein the nucleotide sequence or complement thereof encodes a protein or a part thereof, that alters a stress response and/or growth potential of a transgenic plant exogenously expressing the nucleotide sequence compared to an unmodified plant.

Preferably, the nucleotide sequence has at least 70%, more preferably at least 90%, more preferably at least 95%, most preferably at least 99% identity to the ROB5 gene shown in SEQ ID NO: 1 or a complement thereof.

In a further embodiment there is provided an isolated nucleotide sequence characterized in that the isolated nucleotide sequence is selected from:

a) a ROB5 gene according to SEQ ID NO: 1, or a complement thereof;

b) a nucleotide sequence that hybridizes under stringent conditions to the nucleotide sequence of a), or a complement thereof;

wherein the nucleotide sequence or complement thereof encodes a protein or part thereof that alters a stress response and/or growth potential of a transgenic plant exogenously expressing the nucleotide sequence compared to an unmodified plant.

Preferably, expression of the nucleotide sequence confers on the transgenic plant an altered stress response selected from the group consisting of: increased tolerance to heat, increased tolerance to cold; increased tolerance to frost, increased tolerance to drought, increased tolerance to flood, increase resistance to pests, increased resistance to disease.

Alternatively, expression of the nucleotide sequence confers on the transgenic plant an altered growth potential selected from the group consisting of: faster growth rate, slower growth rate, larger biomass, and smaller biomass, More preferably, expression of the nucleotide sequence in a plant causes the plant to exhibit higher survival rate in adverse conditions compared to an unmodified plant.

The present invention also encompasses an isolated and purified peptide characterized in that the isolated and purified peptide is encoded by a nucleotide sequence as described herein, or a complement thereof. Further provided is a DNA expression cassette comprising a nucleotide sequence of the present invention operably linked to a promoter.

In further aspects, the invention provides a construct comprising a vector and a nucleotide sequence or expression cassette as described herein. Preferably, the construct includes a promoter selected from the group consisting of: a constitutive promoter, an inducible promoter, an organ specific promoter, a tissue-specific promoter, a strong promoter, a weak promoter, and a stress induced promoter.

In another aspect, the invention provides a plant cell or a plant, characterized in that the plant cell or plant is transformed with the construct.

In yet another aspect, the invention provides for a method of genetically modifying a plant, characterized in that the method comprises the steps of:

(a) introducing into a plant cell capable of being transformed and regenerated into a whole plant a construct comprising, in addition to the DNA sequences required for transformation and selection in plants, a nucleotide sequence as described herein, operably linked to a promoter; and (b) recovery of a plant which contains the nucleotide sequence.

Preferably, the plant exhibits an altered stress tolerance and/or altered growth potential compared to an unmodified plant. More preferably, the plant exhibits an altered stress response selected from the group consisting of: increased tolerance to heat, increased tolerance to cold; increased tolerance to frost, increased tolerance to drought, increased tolerance to flood, increase resistance to pests, increased resistance to disease. Preferably, the plant exhibits an altered growth potential selected from the group consisting of: faster growth rate, slower growth rate, larger biomass, and smaller biomass.

In an alternative aspect, the invention includes a method of identifying and isolating a DNA sequence substantially homologous to the nucleotide sequences described herein, characterized in that the method comprises the steps of:

synthesizing a degenerate oligonucleotide primer than can hybridize to the ROB5 nucleotide sequence under stringent conditions;

labelling the degenerate oligonucleotide primer; and using the labelled degenerate oligonucleotide primer as a probe to screen a DNA library for the substantially homologous DNA sequence, and isolating the substantially homologous DNA sequence from the library.

In yet another aspect, the invention pertains to a pair of primers characterized in that the primers hybridize to selected portions of the nucleotide sequences described herein, for amplifying a region of DNA between the primers by polymerase chain reaction.

In further aspects, the invention provides for the use of an isolated nucleotide sequence as described herein, characterized in that the use is for generating a transgenic plant that exhibits an altered stress response compared to an unmodified plant. The invention also provides for the use of an isolated nucleotide sequence as described herein, characterized in that the use is for generating a trangenic plant that exhibits an altered growth potential compared to an unmodified plant.

In another aspect, the invention provides a method of producing a transgenic plant with a modified stress response and/or growth potential, characterized in that the method comprises the steps of:

(a) introducing into a plant cell capable of being transformed and regenerated into a whole plant a construct comprising, in addition to the DNA sequences required for transformation and selection in plants, a nucleotide sequence derived from a ROB5 gene operably linked to a promoter; and (b) recovery of a plant which contains the nucleotide sequence and has a modified stress response and/or growth potential compared to an unmodified plant.

Preferably, the method involves a nucleotide sequence encoding a peptide having at least 50% identity, more preferably at least 70% identity, more preferably at least 90% identity, more preferably at least 95% identity, most preferably at least 99% identity to the peptide indicated in SEQ ID NO: 1, or a part thereof, or a complement thereof.

Alternatively, the method involves the nucleotide sequence indicated in SEQ ID NO: 1, or a part thereof, or a complement thereof, or a nucleotide sequence that binds under stringent conditions to the nucleotide sequence indicated in SEQ ID NO: 1, or a part thereof, or a complement thereof. Various sense/antisense orientation and expression combinations for ROBS expression are within the scope of the constructs, plants and methods of the invention.

In yet another aspect, the invention further encompasses a method of identifying a plant that has been successfully transformed with a construct, characterized in that the method comprises the steps of:

(a) introducing into plant cells capable of being transformed and regenerated into whole plants a construct comprising, in addition to the DNA sequences required for transformation and selection in plants, a nucleotide sequence derived from a ROB5 gene and encoding at least part of a ROB5 gene product, operably linked to a promoter;

(b) regenerating the plant cells into whole plants; and (c) inspecting the plants to determine those plants successfully transformed with the construct, and expressing the nucleotide sequence.

In another aspect, the invention provides for a bicistronic vector characterized in that the bicistronic vector comprises a first ROB5 nucleotide sequence operatively linked to a first tissue-specific promoter, and a second ROB5 nucleotide sequence operatively linked to a second tissue-specific promoter. Preferably, expression of the vector in a transgenic plant induces alternative stress tolerance and growth potential characteristics in difference tissues of the plant according to the first and second nucleotide sequences and the operatively linked first and second promoters. Alternatively, the first nucleotide sequence is oriented in a sense direction relative to the first promoter, and the second nucleotide sequence is oriented in an antisense direction relative to the second promoter. Preferably, the first nucleotide sequence encodes a biologically active form of a ROB5 protein or a part thereof, and the second nucleotide sequence encodes a biologically inactive form of a ROB5 protein or a part thereof.

In a further aspect, the invention includes transgenic plants transformed with a bicistronic or multicistronic vector as described herein.

BRIEF DESCRIPTION OF THE DRAWINGS

FIG. 1 illustrates the cDNA and corresponding peptide sequence for the ROB5 gene isolated from Bromegrass.

FIG. 7(c) provides comparative photographs of control and COR78 :ROB5 transformed seedlings after extended drought conditions (transformed line 13514).

FIG. 7(d) provides comparative photographs of control and COR78:ROB5 transformed plants after extended drought conditions (transformed line 13911).

FIG. 37(a) illustrates enhanced germination and seed quality of COR78:ROB5 transformed canola plants compared to control plants under both non salt stressed and salt stressed conditions. The graphs show percentage germination (% G) for control and transformed plants (mean 4 plates) over an 8day period at stressed sites under conditions of no salt stress (ddH2O applied at 24° C.).

FIG. 37(b) show percentage germination (% G) for control and transformed plants (mean 4 plates) over a 7day period at stressed sites under conditions of salt stress (80 mM salt applied at 24° C.).

DEFINITIONS

Figure 2:
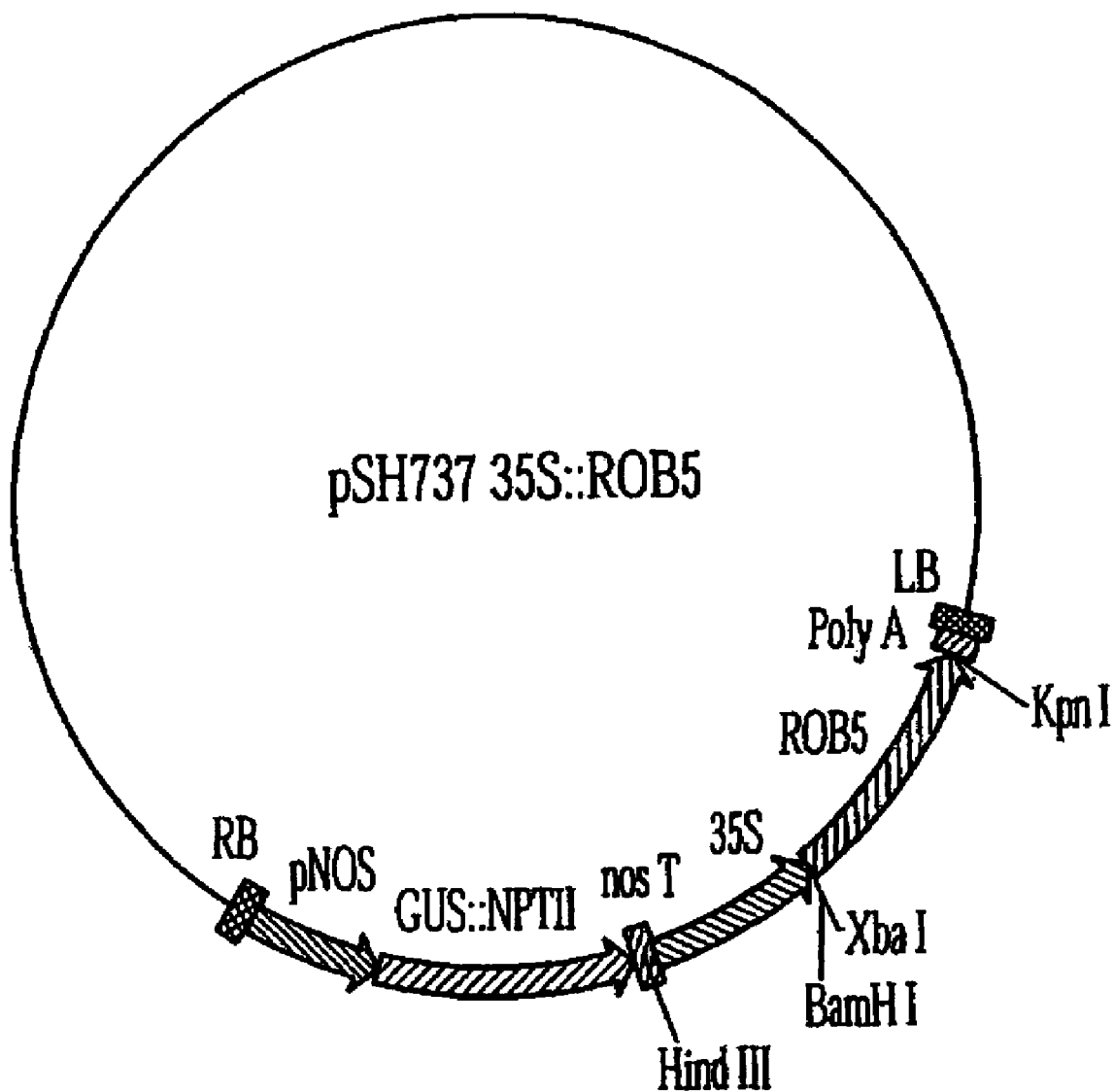
FIG. 2 provides a schematic illustration of transformational vector pBIN19 with the 35S promoter and the ROB5 gene.

The singular forms "a," "an," and "the" include plural reference unless the context clearly dictates otherwise.

A "coding sequence" or "coding region" is the part of a gene that codes for the amino acid sequence of a protein, or for a functional RNA such as a tRNA or rRNA. A coding sequence typically represents the final amino acid sequence of a protein or the final sequence of a structural nucleic acid. Coding sequences may be interrupted in the gene by intervening sequences, typically intervening sequences are not found in the mature coding sequence.

Unless indicated otherwise, "C" as indicated in this specification and Figures means "Control". Control plants or seeds pertain to substantially wild-type plants (which may include an empty vector), which have not undergone modification with a ROB5 transformation vector.

"Exogenous" gene expression pertains to the expression of a gene sequence within a cell, or within the cells of an organism, wherein the gene sequence has been introduced artificially into the cell or organism (e.g. by transformation/transfection). Exogenous gene expression contrasts to "endogenous" gene expression, which occurs from within the wild-type genome of the cell. The presence of the exogenous gene sequence may confer properties to the modified cell or organism that are not present in a corresponding unmodified cell or organism. A gene may be exogenously expressed from a gene cassette that forms part of an expression construct. Moreover, the expression construct may remain independent from the endogenous DNA of the cell(s), or may become more stably integrated into the genome of the cell(s).

A "bicistronic" vector or a "bicistronic" construct encompasses an transformable DNA sequence having at least two promoter sequences. In the case of the bicistronic construct, each promoter sequence is operatively linked to a coding sequence to form a gene cassette, such that expression of each gene cassette results in the production of a corresponding ribonucleic acid. The term "bicistronic" is intended to encompass "multicistronic", such that multicistronic constructs may include multiple gene cassettes.

A "polynucleotide encoding an amino acid sequence" refers to a nucleic acid sequence that encodes the genetic code of at least a portion of a mature protein sequence, typically a contiguous string of amino acids typically linked through a peptide bond. An "amino acid sequence" is typically two or more amino acid residues, more typically 10 or more amino acids in a specific defined order.

A "complement" or "complementary sequence" is a sequence of nucleotides which forms a hydrogen-bonded duplex with another sequence of nucleotides according to Watson-Crick base-pairing rules. For example, the complementary base sequence for 5'-AGCT-3' is 3'-TCGA-5'.

"Expression" refers to the transcription of a gene into structural RNA (rRNA, tRNA) or messenger RNA (mRNA) with subsequent translation into a protein in the case of the mRNA.

Polynucleotides are "functionally equivalent" if they perform substantially the same biological function. By substantially the same biological function it is meant that similar protein activities or protein function are encoded by a mRNA polynucleotide, or a structural polynucleotide has a similar structure and biological activity.

Polynucleotides are "heterologous" to one another if they do not naturally occur together in the same arrangement in the same organism. A polynucleotide is heterologous to an organism if it does not naturally occur in its particular form and arrangement in that organism.

Polynucleotides or polypeptides have "homologous" or "identical" sequences if the sequence of nucleotides or amino acid residues, respectively, in the two sequences is the same when aligned for maximum correspondence as described herein. Sequence comparisons between two or more polynucleotides or polypeptides are generally performed by comparing portions of the two sequences over a portion of the sequence to identify and compare local regions. The comparison portion is generally from about 20 to about 200 contiguous nucleotides or contiguous amino acid residues or more. The "percentage of sequence identity" or "percentage of sequence homology" for polynucleotides and polypeptides, such as 50, 60, 70, 80, 90, 95, 98, 99 or 100 percent sequence identity may be determined by comparing two optimally aligned sequences which may or may not include gaps for optimal alignment over a comparison region, wherein the portion of the polynucleotide or polypeptide sequence in the comparison may include additions or deletions (i.e., gaps) as compared to the reference sequence (which does not comprise additions or deletions) for optimal alignment of the two sequences.

The percentage of homology or similarity is calculated by: (a) determining the number of positions at which the identical nucleic acid base or amino acid residue occurs in both sequences to yield the number of matched positions; (b) dividing the number of matched positions by the total number of positions in the window of comparison; and, (c) multiplying the result by 100 to yield the percentage of sequence identity.

Optimal alignment of sequences for comparison may be conducted by computerized implementations of known algorithms, or by inspection. Readily available sequence comparison and multiple sequence alignment algorithms are, respectively, the Basic Local Alignment Search Tool (BLAST) (Altschul, S. F. et al. 1990. J. Mol. Biol. 215:403; Altachul, S. F. et at 1997. Nucleic Acids Res. 25:3389-3402) and ClustalW programs. Other suitable programs include GAP, BESTF1T, FASTA, and TFASTA in the Wisconsin Genetics Software Package (Genetics Computer Group (GCG), 575 Science Dr., Madison, Wis.). For greater certainty, as used herein and in the claims, "percentage of sequence identity" or "percentage of sequence homology" of amino acid sequences is determined based on optimal sequence alignments determined in accordance with the default values of the BLASTX program, available as described above.

Sequence identity typically refers to sequences that have identical residues in order, whereas sequence similarity refers to sequences that have similar or functionally related residues in order. For example an identical polynucleotide sequence would have the same nucleotide bases in a specific nucleotide sequence as found in a different polynucleotide sequence. Sequence similarity would include sequences that are similar in character for example purines and pyrimidines arranged in a specific fashion. In the case of amino acid sequences, sequence identity means the same amino acid residues in a specific order, where as sequence similarity would allow for amino acids with similar chemical characteristics (for instance basic amino acids, or hydrophobic amino acids) to reside within a specific order.

The terms "stringent conditions" or "stringent hybridization conditions" includes reference to conditions under which a probe will hybridize to its target sequence, to a detectably greater degree than other sequences (e.g. at least 2-fold over background). Stringent conditions are sequence-dependent and will be different in different circumstances. Longer sequences hybridize specifically at higher temperatures. Generally, stringent conditions are selected to be about 5° C. lower than the thermal melting point (Tm) for the specific sequence at a defined ionic strength and pH. The Tm is the temperature (under defined ionic strength and pH at which 50% of a complementary target sequence hybridizes to a perfectly matched probe. Typically, stringent conditions will be those in which the salt concentration is less than about 1.0 M Na ion, typically about 0.01 to 1.0 M Na ion concentration (or other salts) at pH 7.0 to 8.3 and the temperature is at least about 30° C. for short probes (e.g. 10 to 50 nucleotides) and at least about 60° C. for long probes (e.g. greater than 50 nucleotides). Stringent conditions may also be achieved with the addition of destabilizing agents such as formamide. Exemplary low stringency conditions include hybridization with a buffer solution of 30% formamide, 1 M NaCl, 1% SDS at 37° C., and a wash in 2×SSC at 50° C. Exemplary high stringency conditions include hybridization in 50% formamide, 1 M NaCl, 1% SDS at 37° C., and a wash in 0.1×SSC at 60° C. Hybridization procedures are well-known in the art and are described in Ausubel et al.,(Ausubel F. M., et al.,1994, Current Protocols in Molecular Biology, John Wiley & Sons Inc.).

"Isolated" refers to material that is: (1) substantially or essentially free from components which normally accompany or interact with it as found in its naturally occurring environment; or (2) if in its natural environment, the material has been non-naturally altered to a composition and/or placed at a locus in the cell not native to a material found in that environment. The isolated material optionally comprises material not found with the material in its natural environment. For example, a naturally occurring nucleic acid becomes an isolated nucleic acid if it is altered, or if it is transcribed from DNA which is altered, by non-natural, synthetic methods performed within the cell from which it originates.

Two DNA sequences are "operably linked" if the linkage allows the two sequences to carry out their normal functions relative to each other. For instance, a promoter region would be operably linked to a coding sequence if the promoter were capable of effecting transcription of that coding sequence and said coding sequence encoded a product intended to be expressed in response to the activity of the promoter.

A "polynucleotide" is a sequence of two or more deoxyribonucleotides (in DNA) or ribonucleotides (in RNA).

A "DNA construct" is a nucleic acid molecule that is isolated from a naturally occurring gene or which has been modified to contain segments of nucleic acid which are combined and juxtaposed in a manner which would not normally otherwise exist in nature.

A "polypeptide" is a sequence of two or more amino acids.

A "promoter" or transcriptional regulatory region is a cis-acting DNA sequence, generally located upstream of the initiation site of a gene, to which RNA polymerase may bind and initiate correct transcription.

A "recombinant" polynucleotide, for instance a recombinant DNA molecule, is a novel nucleic acid sequence formed through the ligation of two or more nonhomologous DNA molecules (for example a recombinant plasmid containing one or more inserts of foreign DNA cloned into it).

"Stress tolerance" refers to any type of stress that a plant may have to endure, and the capacity of such plant to tolerate the stress. The stress may be selected from a group including, but not limited to, heat, cold, frost, drought, flood, high winds etc. The stress may also be induced by other external factors including pest infestation and plant disease. Therefore the term "stress" further encompasses such insults. Stress tolerance relates to the capacity of a plant to cope with any such stresses without excessive damage and/or death.

"Growth potential" refers to the present and future ability of a plant to exhibit increased growth or vigor. Such growth may pertain to the entire biomass of the plant, but may also relate to the growth of specific organs. Increased growth or vigor relates to the rate at which a particular plant or plant organ changes weight. Typically such change in weight will be a gain in weight, but in certain in circumstances may also pertain to a loss in weight where desirable.

"Transformation" means the directed modification of the genome of a cell by the external application of recombinant DNA from another cell of different genotype, leading to its uptake and integration into the subject cell's genome.

A "transgenic plant" encompasses all descendants, hybrids, and crosses thereof, whether reproduced sexually or asexually, and which continue to harbour the foreign DNA.

DETAILED DESCRIPTION OF THE PREFERRED EMBODIMENTS

The present invention describes the isolation and characterization of genes, and their correspondingly encoded proteins, that will be collectively referred to as 'ROB5'. The inventors have not only successfully isolated ROB5 but have also determined that the expression of ROB5 in a transgenic plant can have an unexpectedly powerful effect upon the stress tolerance of the plant. Even more unexpected was the dramatic effect of ROB5 expression upon the growth potential of the plant. In this regard, exogenous ROB5 expression significantly improves plant vigor and plant biomass for a predetermined time period, compared to an unmodified plant.

The present invention therefore defines a group of genes for which no close homologues are known to exist. Several alignment programs have been used by the inventors to determine that ROB5 gene and protein sequences are unique amongst known plant gene and protein sequences. Table 1 indicates that the ROB5 protein is 100% divergent and generally shows only about 30% or less sequence identity to other proteins known in the art. This data indicates that ROB5 encompasses an entirely novel set of genes and proteins, which likely harbour specialized cellular functions. Since ROB5 is upregulated in response to various plant stresses, ROB5 is likely involved in the mediation of metabolic pathways for preventing cellular or genomic damage within the cells and tissues of the plant. In any event, the capacity of ROB5 to confer advantageous properties to transgenic plants exogenously expressing the protein is unprecedented.

The present invention therefore encompasses nucleotide sequences which include the ROB5 gene sequence, or fragments thereof, of homologues thereof. Such nucleotide sequences include, but are not limited to, the gene sequence indicated in FIG. 1 and fragments thereof. Preferably, the nucleotide sequences of the invention have the capacity to alter plant metabolism, such that exogenous expression of ROB5 in a plant induces the plant to exhibit one or more altered characteristic compared to an unmodified plant, each characteristic being selected from a group including but not limited to: improved tolerance to heat, cold, drought, flood, frost, low nutrient tolerance, high toxin tolerance, pest resistance, disease resistance. The sequences of the present invention further include the nucleotide and peptide sequences derived from the sequence shown in FIG. 1.

For the purposes of the present invention, nucleic acid sequences encoding a protein with substantial homology of 50% or more to the protein encoded by SEQ ID NO: 1, the proteins at least capable of altering plant stress tolerance and/or altering plant growth potential, are herein referred to as "ROB5" coding sequences, encoding a "ROB5" protein. Hence a "ROB5 gene" encodes a protein substantially similar to the protein encoded by the gene indicated in SEQ ID NO: 1, in terms of both amino acid sequence and biological function.

The present invention encompasses the use of the ROB5 gene, and parts thereof, complements thereof, and homologues thereof, for generating transgenic plants with altered stress responses and/or growth characteristics. The present invention also encompasses the use of nucleic acid sequences encoding peptides having at least 50% identity, preferably 70% identity, preferably 90% identity, more preferably 95% identity, most preferably 99% identity to the peptides encoded by the ROB5 gene. In this regard, homologous proteins with at least 50% or 70% predicted amino acid sequence identity are expected to encompass proteins with activity as those defined by the present invention, wherein disruption of expression or overexpression of the homologous proteins is expected to generate plants with altered growth potential as described in the present application. Such proteins may be derived from similar or unrelated species of plants.

The present invention also encompasses polynucleotide sequences encoding peptides comprising at least 90%, 95% or 99% sequence identity to the peptides encoded by the ROB5 gene. This class of related proteins is intended to include close gene family members with very similar or identical catalytic or other biological activity. In addition, peptides with 90% to 99% amino acid sequence identity may be derived from functional homologues of similar species of plant, or from directed mutations to the sequences disclosed in the present application.

The nucleic acid sequences provided in the present invention can be used to alter plant characteristics and morphology by heterologous expression, for example, of SEQ ID NO: 1 and other homologous sequences as described herein.

The polynucleotide sequences of the present invention must be ligated into suitable vectors before transfer of the genetic material into plants. For this purpose, standard ligation techniques that are well known in the art may be used. Such techniques are readily obtainable from any standard textbook relating to protocols in molecular biology, and suitable ligase enzymes are commercially available.

In another embodiment of the present invention, the nucleic acid sequence, or coding region thereof for ROB5 can used to modify plant stress responses and/or growth potential by using said sequence to isolate a homologous nucleic acid that encodes a protein that is at least 50% homologous to the protein encoded by SEQ ID NO: 1, and expressing said homologous nucleic acid as part of a recombinant DNA construct in a host plant species. The recombinant DNA construct so expressed may be engineered to express an altered form of the wild-type protein, or engineered to reduce the expression of the wild-type gene. Method for the identification and isolation of homologous DNA sequences are very well known in the art and are included, for example in Sambrook et al., *Molecular Cloning: A Laboratory Manual,* Cold Spring Harbour Press, Cold Spring Harbour, N.Y.(1989). For example, the nucleotide sequence shown in SEQ ID NO: 1 can be utilized to design oligonucleotide probes. The probes can be labelled (e.g. radiolabelled) and used to screen cDNA or genomic DNA libraries of bromegrass and other plant species for DNA sequences that are homologous to ROB5.As is well known in the art, the hybridization conditions of DNA library screening can determine the degree of specificity of homologous sequence annealing and recognition. For example, conditions of high stringency will identify only those DNA sequences more closely related to ROB5,whereas conditions of lower stringency will identify further DNA sequences that have less homology to ROB5.

In another embodiment of the invention, the nucleotide sequence shown in SEQ ID NO: 1 may be used for the identification of related homologous sequences deposited in public databases through comparative techniques well-known in the art, for the identification of related cDNA or genomic DNA sequences from various species, including plant species where the DNA sequence information is not known. In particular it is contemplated that these sequences so described can be used for the isolation of plant genes encoding peptides having similar activities.

Further, it is apparent to one skilled in the art that the polynucleotide and amino acid sequence of SEQ ID NOS: 1 and 2 can be used to isolate related genes from various other plant species. The similarity or identity of two polypeptide or polynucleotide sequences is determined by comparing sequences. In the art, this is typically accomplished by alignment of the amino acid or nucleotide sequences and observing the strings of residues that match. The identity or similarity of sequences can be calculated by known means including, but not limited to, those described in *Computational Molecular Biology,* Lesk A. M., ed., Oxford University Press, New York, 1988, *Biocomputing: Informatics and Genome Projects,* Smith, D. W., ed., Academic Press, New York, 1993., *Computer Analysis of Sequence Data, Part I,* Griffin, A. M. and Griffin, H. G., eds., Humana Press, New Jersey, 1994 and other protocols known to those skilled in the art. Moreover, programs to determine relatedness or identity are codified in publicly available programs. One of the most popular programs comprises a suite of BLAST programs, three designed for nucleic acid sequences (BLASTN, BLASTX and TBLASTX), and two designed for protein sequences (BLASTP and TBLASTN) (Coulson, Trends in Biotechnology, 12:76-80, 1994). The BLASTX program is publicly available from NCBI and other sources such as the BLAST Manual, Altschul, S., et al., NCBI NLM NIH Bethesda Md. 20984, and Altschul, S., et al., J. Mol. Biol 215:403-410, 1990.

The isolated polynucleotide can be sequenced and the DNA sequence used to further screen DNA sequence collections to identify related sequences from other species.

The DNA sequence collections can comprise EST sequences, genomic sequences or complete cDNA sequences.

Site-directed mutagenesis techniques are also readily applicable to the polynucleotide sequences of the present invention, to make the sequences better suited for use in generated morphologically modified transgenic plants. Related techniques are well understood in the art, for example as provided in Sambrook et al., *Molecular Cloning: A Laboratory Manual*, Cold Spring Harbour Press, Cold Spring Harbour, N.Y.(1989). In this regard, the present invention teaches the use of nucleotide sequences derived from the ROB5 gene. However, the present invention is not intended to be limited to these specific sequences. Numerous directed mutagenesis techniques would permit the non-informed technician to alter one or more residues in the nucleotide sequences, thus changing the subsequently expressed polypeptide sequences. Moreover, commercial 'kits' are available from numerous companies that permit directed mutagenesis to be carried out (available for example from Promega and Biorad). These include the use of plasmids with altered antibiotic resistance, uracil incorporation and PCR techniques to generate the desired mutation. The mutations generated may include point mutations, insertions, deletions and truncations as required. The present invention is therefore intended to encompass corresponding mutants of the ROB5 gene, relating to both cDNA and genomic DNA sequences in accordance with the teachings of the present application.

In another embodiment of the present invention, the ROB5 gene sequence, and parts, complements, and homologues thereof are used to modify plant stress responses and/or growth potential by the transformation of plant cells with a plant transformation vector comprising a ROB5 coding region, for example, a region of said nucleic acid illustrated in FIG. 1 under the control of a heterologous or native/homologous promoter.

In another embodiment of the present invention, one or more portions, of at least 10 amino acids of the protein encoded by the nucleic acid sequence shown in SEQ ID NO: 1 are expressed in a host plant, said expression causing the alteration of plant stress responses and/or growth potential.

In another embodiment of the present invention, the nucleic acid sequence shown in SEQ ID NO: 1, or parts thereof or homologues thereof, is used to modify plant stress responses and/or growth potential by the transformation of plant cells with a plant transformation vector comprising a coding region of said polynucleotide under the control of the promoter normally associated with the ROB5 gene sequences. In alternative embodiments, the ROB5 gene or a derivative thereof may be inserted into a construct under the control of a constitutive promoter such that the gene is expressed from low to high levels in all plant tissues of the transgenic plant. In this way, the modification of plant stress tolerance and/or growth potential will be conferred to the entire plant. In further alternative embodiments, the ROB5 gene or parts or homologues thereof may be inserted into a construct for plant transformation under the control of a tissue specific promoter. In this way, the modification of plant stress responses and/or growth potential will be conferred only to selected tissues and organs of the plant. Alternatively, the promoter may be stress responsive, only activating exogenous expression of ROB5 if certain conditions are met. Such conditions may include, but are not limited to, infestation, disease, or environmental conditions such as heat, cold, frost, drought, flood etc. Many such promoters are well known to those skilled in the art, and their use in conjunction with ROB5 is intended to fall within the scope of the invention.

In one embodiment of the invention the nucleic acid sequence shown in SEQ ID NO: 1 or parts thereof or homologues thereof, is used to alter the phenotype of a bromegrass, canola, flax, or potato plant by the introduction of the nucleotide sequence or a portion thereof into such a plant and recovering a transgenic plant that exhibits altered stress tolerance and/or growth potential relative to an unmodified plant.

In another embodiment of the present invention, nucleic acids encoding a protein with at least 50% identity to the protein sequence indicated in SEQ ID NO: 2 are isolated by routine techniques as described herein, and said nucleic acids are used to alter the stress tolerance and/or growth potential of the plant species from which they were derived by introduction of said nucleic acids or portion thereof, into cells of said plant species and recovering plants wherein the phenotype of the plant has changed as a result of the introduction of the nucleic acid sequence, or portion thereof into the plant species.

In another embodiment of the present invention, said nucleic acids that encode a protein at least 50% identity to the protein encoded by the nucleotide sequence indicated SEQ ID NO: 1 are used to alter the stress tolerance and/or growth potential of a plant by introduction of said nucleic acid into a plant species heterologous to the plant species from which said nucleic acid sequence was derived.

In yet another embodiment of the present invention, the nucleic acid sequence shown in SEQ ID NO: 1 is used as a visible marker for plant transformation, said marker producing plants with an altered stress responses and/or growth potential relative to plants not transformed with the same. In this way, plants may be conferred, for example, with a strong capacity to resist cold temperatures. This new feature can be used to select for only those plant successfully transformed with the construct. Also within the scope of the invention are bicistronic vectors comprising both a ROB5 derived sequence, and an additional sequence or sequences for conferring additional modifications to the plant. By 'cold-selecting' such plants, the presence of the second expression sequence in the bicistronic vector may be analyzed after properly transformed plants have been identified and selected. It is the intention of the invention to encompass all such related plant selection techniques that utilize the ROB5 gene, or parts thereof, or homologues thereof. The advantages of using selection systems that do not include antibiotic/herbicide resistance marker genes for producing transgenic plants are well recognized. Since ROB5 expression generates one or more phenotypes that are readily distinguishable from wild type plants, it is possible to develop transformation vectors based on the ROB5 gene that are devoid of any antibiotic or herbicide selection markers to provide a novel and very efficient alternative to the currently available selection systems.

In yet another embodiment of the present invention, the expression of an endogenous ROB5 gene sequence is modified by the presence of an exogenous ROB5 coding sequence. The exogenous ROB5 coding sequence can be an altered form of the endogenous ROB5 coding region normally found in said plant species, or a ROB5 functional homologue from a different plant species. Expression of the exogenous ROB5 protein may be expected to alter the activity of the native ROB5 protein, or the exogerously produced ROB5 protein can encode an activity that provides a phenotypic distinction.

In another embodiment of the invention there is provided a method of expressing a ROB5 gene sequence or derivative thereof in a plant species comprising the steps of:
  a) introducing into a plant cell capable of being transformed a genetic construct comprising a first DNA expression cassette that comprises, in addition to the DNA sequences required for transformation and selection in said cells, a DNA sequence derived from a ROB5 gene, for example, that encodes a peptide having at least 50% homology to the peptide encoded by ROB5, operably linked to a suitable transcriptional regulatory region and,
  b) recovery of a plant which contains said DNA sequence.

The suitable transcriptional regulatory region can be the regulatory region normally associated with the ROB5 gene or ROB5 coding sequence, or a heterologous transcriptional regulatory region.

In another embodiment of the invention the subject method includes a method for modifying the stress tolerance and/or growth potential of a plant comprising:
  (a) Introducing into a plant cell capable of being transformed and regenerated to a whole plant a genetic construct comprising a first DNA expression cassette that comprises, in addition to the DNA sequences required for transformation and selection in plant cells, a DNA sequence that comprises a polynucleotide region encoding a ROB5 gene or a part thereof, operably linked to a suitable transcriptional regulatory region and,
  (b) recovery of a plant which contains said recombinant DNA.

The use of gene inhibition technologies such as antisense RNA or co-suppression or double stranded RNA interference is within the scope of the present invention. In these approaches, the isolated gene sequence is operably linked to a suitable regulatory element.

Accordingly, in one embodiment of the invention the subject method includes a method to modify the stress response or growth potential of a plant comprising the steps of:
  a.) introducing into a plant cell capable of being transformed a genetic construct comprising a first DNA expression cassette that comprises, in addition to the DNA sequences required for transformation and selection in said cells, a DNA sequence that encodes a ROB5 coding sequence encoding a protein or part thereof having at least 50% sequence identity to the protein encoded by the sequence of SEQ ID NO: 1, at least a portion of said DNA sequence in an antisense orientation relative to the normal presentation to the transcriptional regulatory region, operably linked to a suitable transcriptional regulatory region such that said recombinant DNA construct expresses an antisense RNA or portion thereof of an antisense RNA and,
  b.) recovery of a plant which contains said DNA sequence.

The polynucleotide encoding the ROB5 sequence can be in the antisense (for inhibition by antisense RNA) or sense (for inhibition by co-suppression) orientation, relative to the transcriptional regulatory region. Alternatively a combination of sense and antisense RNA expression can be utilized to induce double stranded RNA interference (Chuang and Meyerowitz, PNAS 97: 4985-4990, 2000, Smith et al., Nature 407: 319-320, 2000).

The present invention also encompasses the use of antisense expression to reduce the levels of ROB5 within the plant, for example for the purposes of reducing the growth potential of the plant. A reduction in stress tolerance or a reduction in growth and vigor (resulting from ROB5 antisense expression) may itself confer significant advantages to a plant, for example for the purposes of reducing wind damage. This concept may be extended to the use of organ-specific and/or tissue-specific promoters and/or the use of bicistronic/multicistronic vectors for modifying overall plant architecture. In one example, a stalk specific promoter may be used with ROB5 in an antisense direction to reduce stalk growth rate. Conversely, a seed specific promoter may be used with ROB5 in a sense direction, thereby increasing the rate of seed development.

Preferably, these two gene cassettes may both be incorporated into a single bicistronic vector. Transgenic plants having such a vector may exhibit short stalks for improved wind damage resistance, and yet may yield large seeds thereby improving productivity. Many more examples of ROB5 sense/antisense expression with various organ or expression combinations specific promoters may be designed, all of which are intended to fall within the scope of the present invention.

These methods and the correspondingly generated transgenic plants rely on the use of transformation techniques to introduce the gene or construct encoding ROB5 (or a part or a homologue thereof) into plant cells. Transformation of a plant cell can be accomplished by a variety of different means. Methods that have general utility include *Agrobacterium* based systems, using either binary and/or cointegrate plasmids of both *A. tumifaciens* and *A. rhyzogenies*. (e.g., U.S. Pat. No. 4,940,838, U.S. Pat. No. 5,464,763), the biolistic approach (e.g, U.S. Pat. No. 4,945,050, U.S. Pat. No. 5,015,580, U.S. Pat. No. 5,149,655), microinjection, (e.g., U.S. Pat. No. 4,743,548), direct DNA uptake by protoplasts, (e.g., U.S. Pat. No. 5,231,019, U.S. Pat. No. 5,453,367) or needle-like whiskers (e.g., U.S. Pat. No. 5,302,523). Any method for the introduction of foreign DNA and/or genetic transformation of a plant cell may be used within the context of the present invention.

The following examples serve to illustrate the method and in no way limit the utility of the invention.

EXAMPLE 1

Attempts to Isolate and Characterize Stress-Response Genes from Bromegrass Using Degenerate Oligonucleotide Probes Derived from Microsequencing Data The inventors' initial attempts to isolate plant stress response proteins were unsuccessful. Abscisic acid responsive heat-stable proteins (enriched for 43-45 kDa polypeptides) were isolated by heat treatment (90° C. for 30 min), $(NH_4)_2 SO_4$ precipitation and Sephadex G-50 chromatography as described previously by Robertson et al. (1994). These protein fractions were used for protection assays and protected thermosensitive proteins against heat and pH induced denaturation in vitro. Sucrose added in combination with the heat-stable abscisic acid responsive proteins showed maximum protection against denaturation.

After heat fractionation and sephadex chromatography, the polypeptides having a size range of about 43-45 kDa were further purified by one and two-dimensional SDS-PAGE prior to N-terminal sequencing and antibody production. N-terminal sequencing confirmed the identity of a 43-45 kDa protein. The sequence was ETTLDD/E AEVAPGKEE (SEQ ID NO: 3). This N-terminal sequence was used to synthesize a degenerate nucleotide probe for screening both cDNA and genomic bromegrass libraries.

Extensive screening of a bromegrass genomic library in EMBL3 Cos with degenerate probes failed to recover the nucleotide sequence coding for the 45 kDa protein.

EXAMPLE 2

Polyclonal Antibody Production, Antibody Purification, and DNA Library Screening Permitted Isolation of ROB5

The 43-45 kDa polypeptides were excised from preparative SDS-PAGE gels, washed with phosphate buffered saline, powdered in liquid nitrogen and prepared for injection into two rabbits using Freunds complete and incomplete adjuvant. Antibody production followed standard procedures and ELISA testing protocols (current protocols In Immunology 1994, Eds. Colgian et al. John Wiley and Sons, Inc. Vols. 1 to 3).

The polyclonal antibodies prepared against the 43 to 45 kDa stress proteins were further purified by crossed-immunoprecipitation against phage (λ ZAP) and host bacterial protein fractions. These antibodies were then used to screen a cDNA library prepared in λ ZAP by using mRNA isolated from abscisic acid (ABA)-treated bromegrass cells and immunoscreening was performed using kits commercially available from Stratagene. Two independent cDNA libraries from bromegrass cells were constructed and screened both with degenerate probes and with polyclonal antibodies directed against the 43-45 kDa proteins. Differential screening using mRNA extracted from control cultures and 5 day ABA-treated (75 µM) bromegrass suspension cultures was also performed. All methods initially failed to isolate putative clones coding for the 43-45 kDa proteins. Differential screening of ABA responsive sequences in other laboratories also failed to isolate cDNAs coding for the 43-45 kDa proteins (Lee, S. P. and T. H. H. Chen. 1993. Plant Physiol. 101: 1086-1096). Further purification of the polyclonal antibodies and screening of a high titer cDNA library gave positive results. Primary screening identified 23 positive clones, three of which were purified and sequenced. Sequencing confirmed that one of the clones coded for one of the 43 to 45 kDa proteins, since part of the translated sequence matched N-terminal sequencing data for the 43 to 45 kDa proteins.

EXAMPLE 3

ROB5 Sequence Analysis

FIG. 1 gives the nucleotide sequence of the ROB5 gene, and the corresponding ROB5 protein thus obtained, the cDNA coding for one of the 43 to 45 kDa proteins previously discussed (see also SEQ ID NOS: 1 and 2). The cDNA is 1419 base pairs long with a translated reading frame of 1158 base pairs. There is a 75 base pair 3'-untranslated region followed by a putative 27 amino acid leader or signal sequence. The N-terminal sequence obtained from proteins purified from bromegrass cells start at amino acid residue 28. The signal sequence is hydrophobic (rich in alanine, valine and leucine) and possibly associates with membranes. Following the stop codon there is a 5' untranslated sequence of 186 base pairs. There are four distinct repeats (KAAAAK: SEQ ID NO: 4)) in the sequence, towards the carboxy terminus. The calculated molecular weight is 39,586.59 Daltons and the calculated isoelectric point is 8.359. The sequence is 29.88% A+T and 70.03% C+G with a melting temperature of 93.18° C.

Several sequence alignment programs were used to look at the relationship of ROB5 to other plant proteins. Table 1 shows ROB5 protein is 100% divergent and shows a 30.6% identity to a Glycine max.PRO, 29.5% to cotton.PRO, and 26.1% to Morus bombycix.PRO group III LEA (Late Embryogenesis Abundant) proteins.

EXAMPLE 4

ROB5 Expression in Response to Plant Stress in Bromegrass Seedlings

Northern and Western blot analyses showed that the ROB5 gene isolated from a bromegrass suspension culture, was not only ABA-responsive, but also drought and cold inducible in bromegrass seedlings. ROB5 expression did not respond to heat shock or salt stress in bromegrass seedlings. However, ABA treated bromegrass suspension cultures show increased tolerance to heat, freezing (Robertson et al. 1994. Plant Physiol. 105:181-190), and salinity (Ishikawa et al. 1995. Plant Science 107:83-93) when the 43 kDa proteins are expressed.

EXAMPLE 5

Construction of ROB5 Plant Expression Vectors

Figure 3:
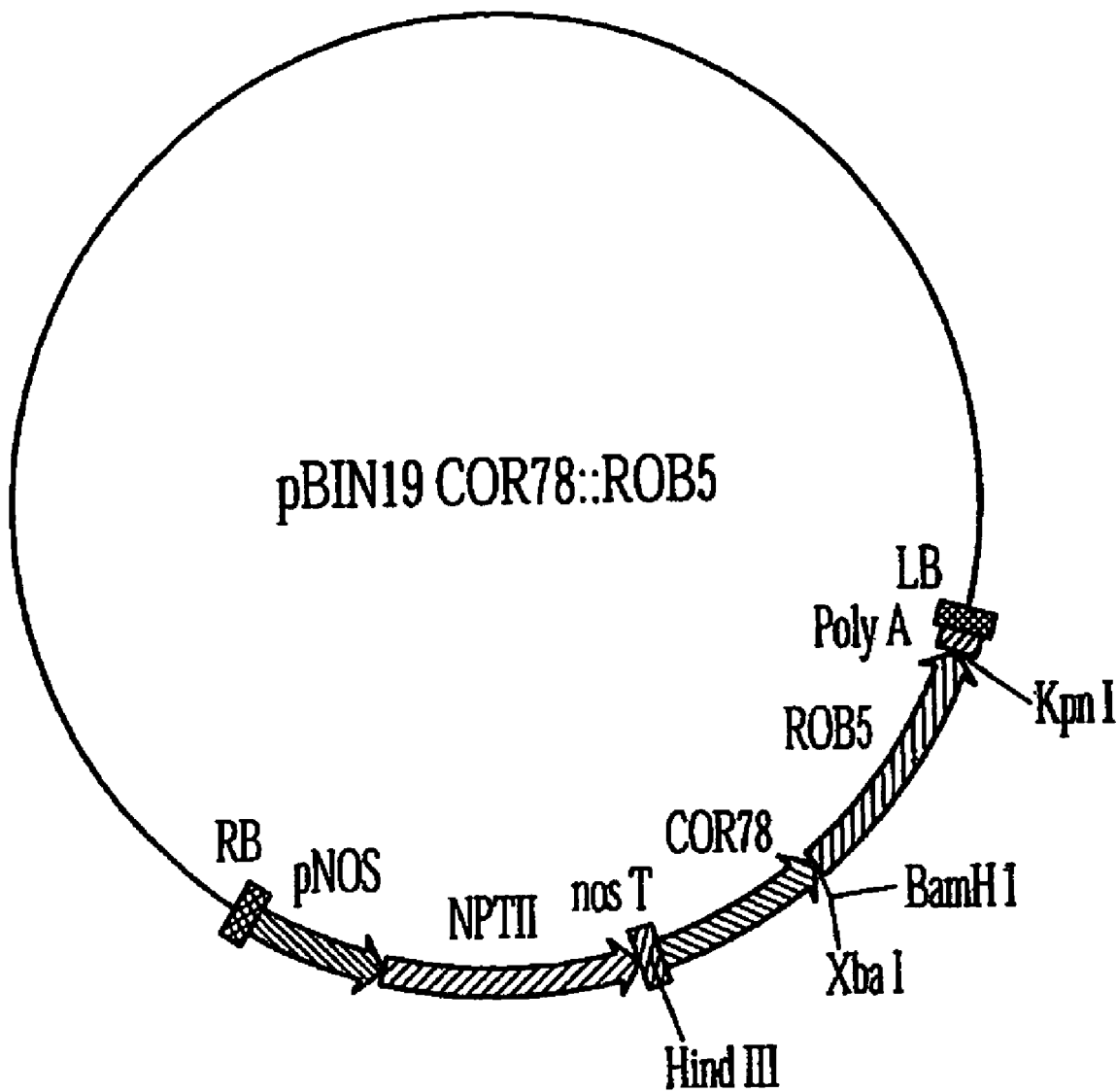
FIG. 3 provides a schematic illustration of the transformational vector pSH737 with the COR78 promoter and the ROB5 gene.
Figure 4:
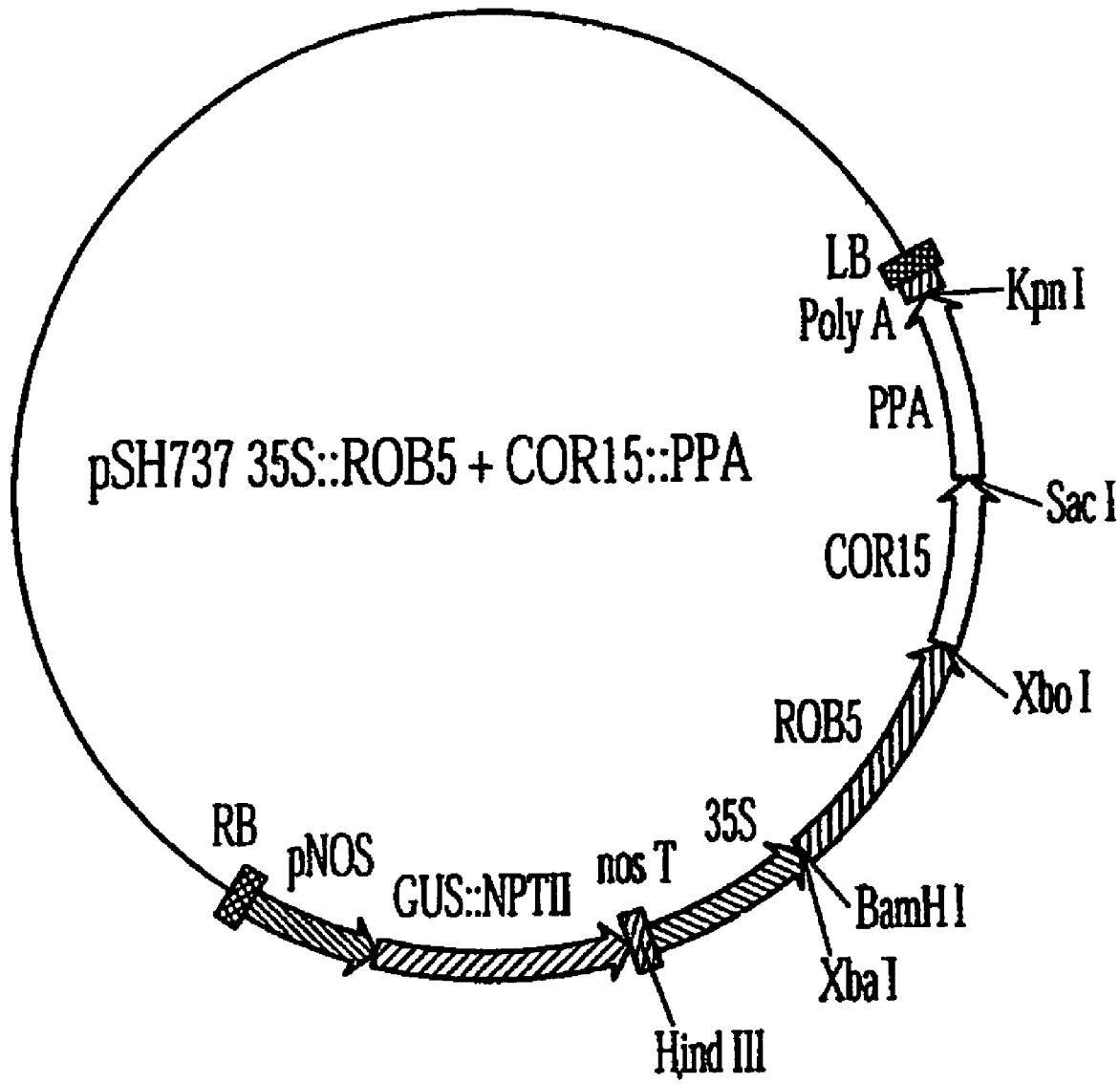
FIG. 4 provides a schematic illustration of the transformational vector pSH737 with the 35S promoter and the ROB5 gene, plus the COR15 promoter and PPA gene.

Three transformation vectors were constructed for the purposes of exogenous expression of ROB5 in plants, as detailed in Table 2. The resulting construct maps are indicated in FIGS. 2, 3, and 4. These vectors were used to transform canola (*Brassica napus*) cv. DH-12075, AAC, Saskatoon, SK, potato (*Solanum tuberosum*) cv Desiree, and flax (*Linum usitatissimum*) cv. CDC Normandy.

The promoters and transformation vectors in this study are publically available. For example, the 35S promoter is available from Monsanto, and the COR78 and COR15 promoters have previously been reported (Thomashow, M. F. 1999. Ann. Rev. of Plant Physiology and Plant Molecular Biology Vol. 50:571-599).

EXAMPLE 6

Figure 5A:
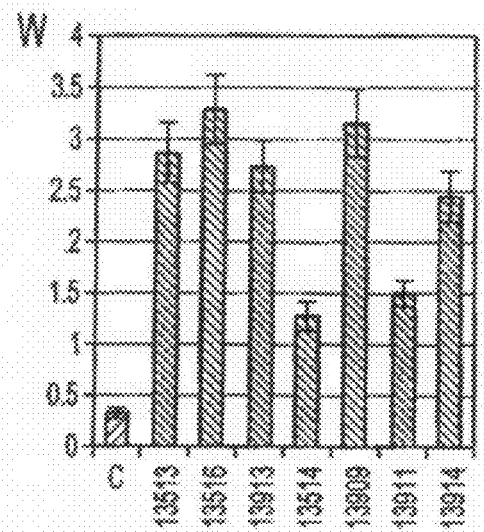
FIG. 5(a) illustrates the effects of ROB5 gene expression in canola, for the purposes of assessing frost tolerance. Plants were incubated at 2° C. (light) and 0° C. (dark) with a 16h photoperiod for 2 days, and then were tested with incubation temperatures as low as −9° C. for 2 cycles over 2 days. The graph compares the total weight of seeds (W) in grams harvested from control canola plants to various lines transformed with the COR78:ROB5 construct.
Figure 5B:
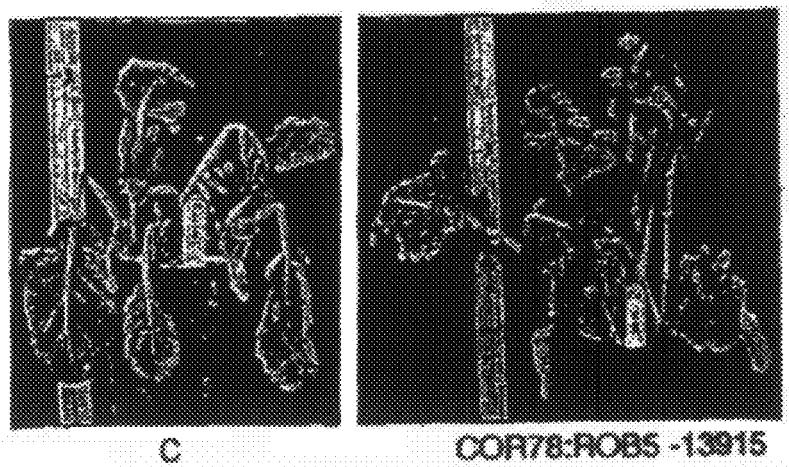
FIG. 5(b) provides comparative photographs of control and COR78:ROB5 transformed line 13915 following frost exposure.
Figure 5C:
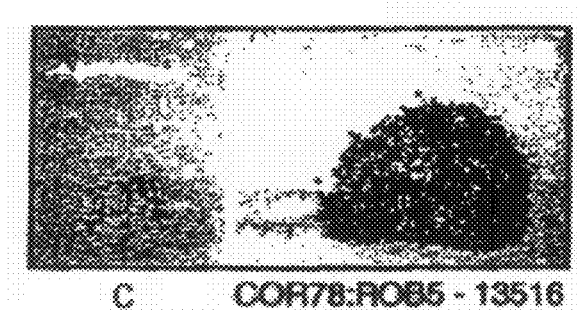
FIG. 5(c) provides comparative photographs of the total seeds harvested from a control plant and COR78:ROB5 transformed line 13516.

Transgenic Canola Plants Expressing ROB5 Exhibit Increased Tolerance to Frost Compared to Control Plants FIG. 5a provides a graph to compare the productivity of seven selected canola lines transformed with COR78:ROB5 and control plants after frost stress testing. Frost tolerance was determined by either controlled freeze tests in the laboratory or by assessing natural frosts in the field. Freezing injury was evaluated either by electrolyte leakage or regrowth. Plants were incubated at 2° C. (light) and 0° C. (dark) with a 16 h photoperiod for 2 days, and then were tested with incubation temperatures as low as −9° C. for 2 cycles over 2 days. The results shown in FIG. 5a indicate that the total weight of seeds (W) in grams harvested from control canola plants was significantly lower compared to each of the various lines transformed with the COR78:ROB5 construct. The comparative photographs shown in FIG. 5b indicate the degree of frost damage in a control plant, and relatively little frost damage in COR78:ROB5 transformed line 13915 following frost exposure. FIG. 5c provides comparative photographs to show that the total seeds harvested from a control plant was significantly less that those harvested from COR78:ROB5 transformed line 13516 following frost exposure. Photographs of the control and one COR78:ROB5 transgenic line are shown after a freeze-thaw cycle and after harvesting seed from control and transgenic plants. In summary, expression of ROB5 in transgenic canola resulted in significant protection against freezing injury and a large increase in final seed yield compared to frost sensitive controls.

EXAMPLE 7

Figure 6A:
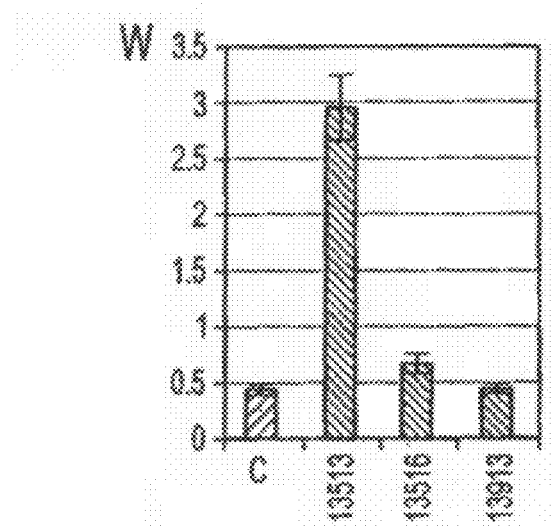
FIG. 6(a) illustrates the effects of ROB5 gene expression in canola, for the purposes of assessing heat tolerance. Plants were incubated at 42° C. for 16h for 2 cycles over 2 days at the flowering stage. The graph compares the total weight of seeds (W) in grams harvested after heat stress of control canola plants to various lines transformed with COR78:ROB5 construct.
Figure 6B:
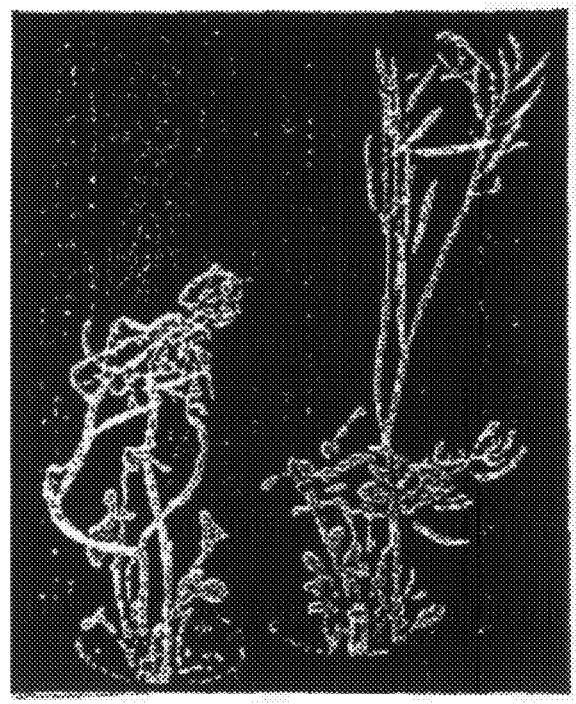
FIG. 6(b) provides comparative photographs of control and COR78:ROB5 transformed line 13513 following heat exposure.

Transgenic Canola Plants Expressing ROB5 Exhibit Increased Tolerance to Heat Compared to Control Plants FIG. 6 shows the effects of heat stress on transgenic plants expressing ROB5. Heat tolerance was determined on whole plants and plant parts (excised stems and leaves). Whole plants or plant parts were heated from 22 to 42° C. over a 12 hour period prior to isothermal incubation at 42° C. Viability was assayed by electrolyte leakage, regrowth, seed yield and seed quality. After described heat stresses most transgenic plants showed better recovery and increased seed yields compared to unmodified plants, as measured by the subsequent number of seeds harvested (FIG. 6a). FIG. 6b provides comparative photographs for control and COR78:ROB5 transformed line 13513 after heat stress.

EXAMPLE 8

Figure 7A:
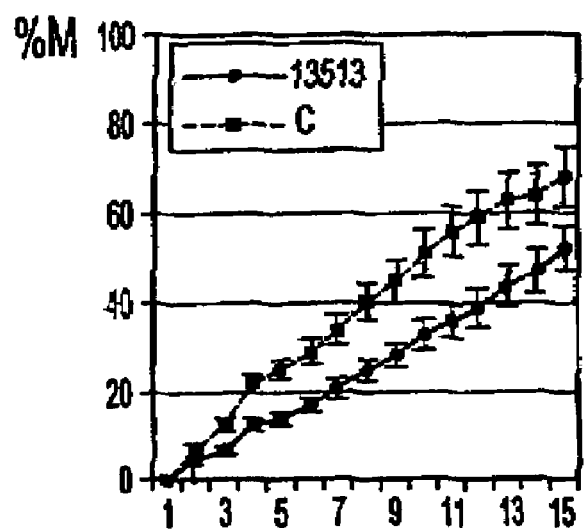
FIG. 7(a) illustrates the effects of ROB5 gene expression in canola, for the purposes of assessing drought tolerance. Moisture loss was assessed over 15 days of drought (no water) conditions. The figure illustrates percentage moisture loss (% M) for control canola and COR78:ROB5 transformed line 13513 over 15 days of withholding water.
Figure 7B:
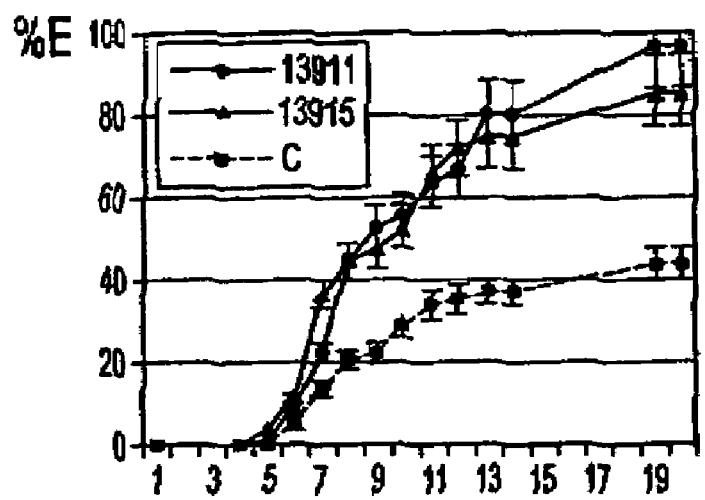
FIG. 7(b) illustrates percentage emergence of seedlings (% E) from 1 to 20 days after seeding for control and two COR78:ROB5 transformed lines (13911 and 13915).

Transgenic Canola Plants Expressing ROB5 Exhibit Increased Tolerance to Drought Compared to Control Plants FIG. 7 shows the effects of drought stress on transgenic plants expressing ROB5.Drought tolerance was determined by withholding water from potted plants (in the three to five leaf stage) for up to 14 days followed by re-watering. The plants were then rated for re-growth potential. Drought tolerance in the field was determined by measuring 1000 Kernal Weights. In drought studies, ROB5 transgenics lost moisture at a slower rate than controls (FIG. 7a). Moreover, transgenic seedling emergence occured more quickly and vigorously compared to the control plants under dry conditions (FIG. 7b). FIGS. 7c and 7d provide comparative photographs of control and transformed plants following exposure to drought conditions.

EXAMPLE 9

Figure 8A:
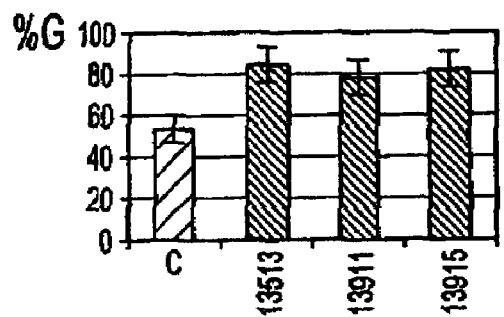
FIG. 8(a) illustrates the effects of ROB5 gene expression in canals, for the purposes of assessing seedling emergence and vigor. Seedling germination conditions pertained to 22° C. for 24h, or 8° C. over time, and included control and COR78:ROB5 transformed plants. The figure illustrates percentage germination (% G) of control and transformed lines (13513, 13911, and 13915) of seeds after 24h at 22° C.
Figure 8B:
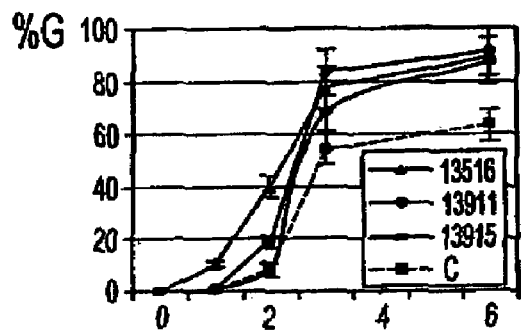
FIG. 8(b) illustrates seedling emergence (E) per meter for control and transformed plants (lines 13909, 13911, and 13912) over days after planting (field trial).
Figure 8C:
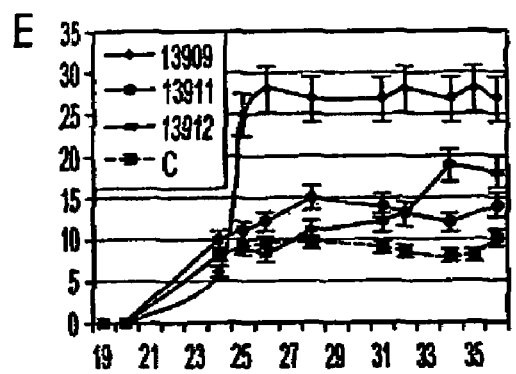
FIG. 8(c) illustrates percentage germination (% G) for control and transformed plants (lines 13516, 13911, and 13915) over days after planting at 8° C.
Figure 9A:
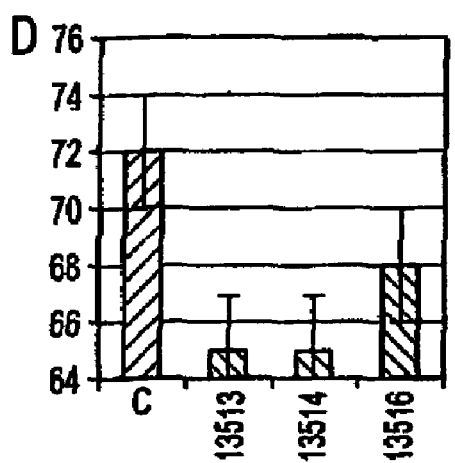
FIG. 9(a) illustrates the effects of ROB5 gene expression in canola, for the purposes of assessing days to flowering and overall yield. Plants were grown in 41 pots outside, and included control and COR78:ROB5 transformed plants. The figure illustrates a comparison of the number of days that control and transformed lines took to flower.
Figure 9B:
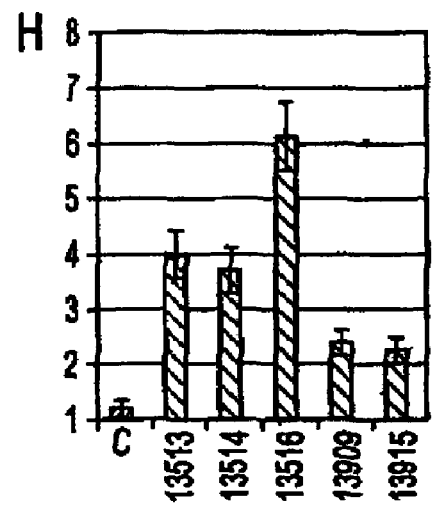
FIG. 9(b) illustrates the percentage of seeds larger than 2.00 mm in diameter (% S) for control and transformed lines.
Figure 9C:
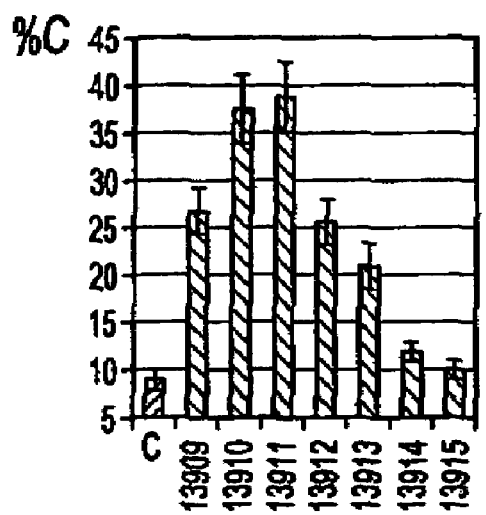
FIG. 9(c) illustrates the height in inches (H) of control and transformed lines 69 days after planting.
Figure 9D:
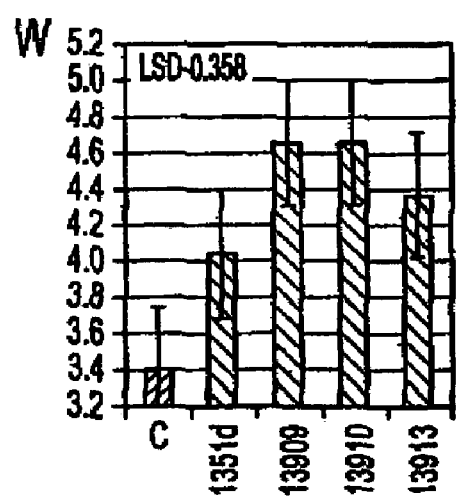
FIG. 9(d) illustrates average weight W (in grams) of 1000 kernel seeds harvested from control and transformed plants.
Figure 9E:
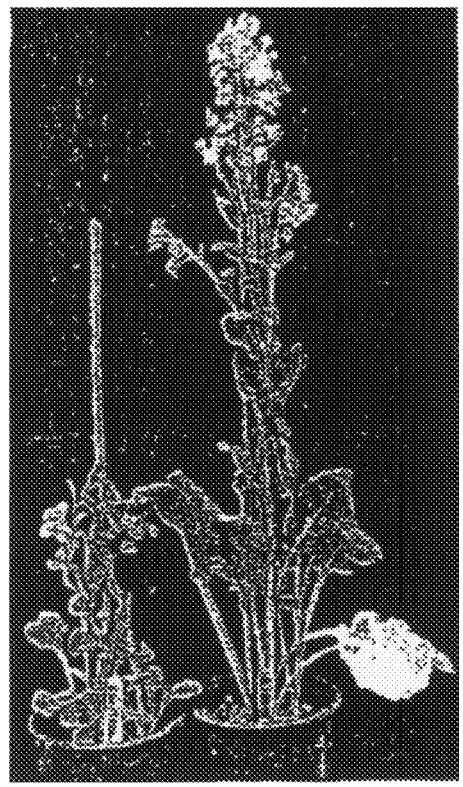
FIG. 9(e) provides comparative photographs of control and transformed line 13514 at 69 days after planting.

Transgenic Canola Plants Expressing ROB5 Exhibit Faster Germination and Emergence Compared to Control Plants FIG. 8 compares the germination and emergence characteristics of control and COR78:ROB5 transformed canola plants. FIG. 8a illustrates a significantly higher germination rate for transformed plants compared to control plants following 24 hours at 22° C. A higher rate of germination was observed for transformed plants at 8° C. over a 6 day monitoring period (FIG. 8c). Field testing was also conducted, and seedling emergence was more rapid with transgenic lines compared to control plants, particularly for line 13909 (FIG. 8b).

EXAMPLE 10

Transgenic Canola Plants Expressing ROB5 Flower and Mature more Quickly than Control Plants FIG. 9 compares the flowering and maturation characteristics of control and COR78:ROB5 transformed canola plants. Transformed plants flowered more quickly (up to 7 days more quickly for selected lines) than control plants (FIG. 9a). Most of the transgenic lines included a much greater percentage of large seeds (diameter >2.00 mm) and a much higher 1000 Kernel Seed Weight compared to control plants (FIGS. 9b and 9d). Moreover, transformed plants were significantly taller than control plants after a 69 day growth period (from planting) (FIGS. 9c, and 9e).

EXAMPLE 11

Figure 10A:
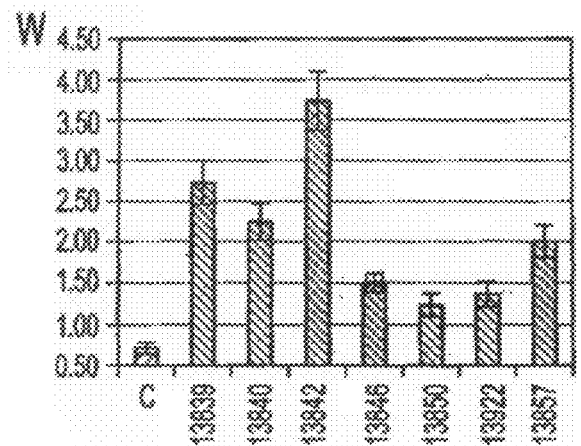
FIG. 10(a) illustrates the effects of ROB5 gene expression in flax, for the purposes of assessing frost tolerance. Plants were incubated at 2° C. (light) and 0° C. (dark) with a 16h photoperiod for 2 days, and then were tested with incubation temperatures as low as −9° C. for 2 cycles over 2 days at the flowering stage. The figure provides a graph to compare the total weight of seeds (W) in grams harvested from control flax plants to various lines transformed with the COR78:ROB5 construct.
Figure 10B:
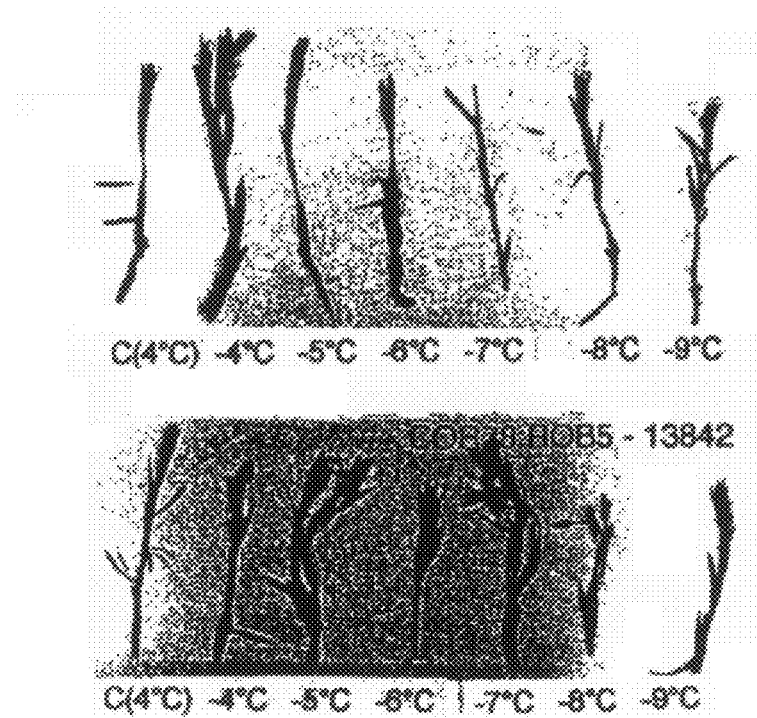
FIG. 10(b) provides comparative photographs of control and COR78:ROB5 transformed lines exposed to different temperatures.

Transgenic Flax Plants Expressing ROB5 Exhibit Increased Tolerance to Frost Compared to Control Plants FIG. 10 compares the frost tolerance characteristics of control and COR78:ROB5 transformed flax plants. FIG. 10a provides a graph to compare the productivity of seven selected flax lines transformed with COR78:ROB5 and control plants after frost stress testing. Frost tolerance was determined by either controlled freeze tests in the laboratory or by assessing natural frosts in the field. Freezing injury was evaluated either by electrolyte leakage or regrowth. Plants were incubated at 2° C. (light) and 0° C. (dark) with a 16 h photoperiod for 2 days, and then were tested with incubation temperatures as low as −9° C. for 2 cycles over 2 days. The results shown in FIG. 10a indicate that the total weight in grams of the control canola plants was significantly lower compared to each of the various lines transformed with the COR78:ROB5 construct. The comparative photographs shown in FIG. 10b indicate the degree of frost damage in control plants, and relatively little frost damage in COR78:ROB5 transformed line 13842 following frost exposure. In summary, expression of ROB5 in transgenic flax resulted in significant protection against freezing injury.

EXAMPLE 12

Figure 11A:
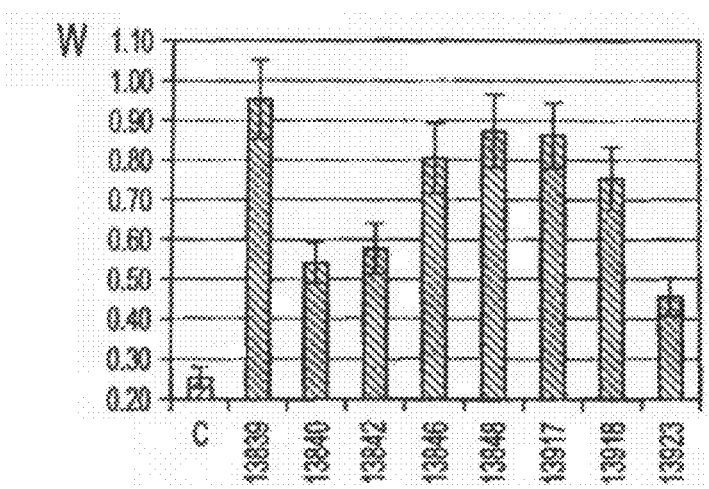
FIG. 11(a) illustrates the effects of ROB5 gene expression in flax, for the purposes of assessing heat tolerance. Plants were incubated at 42° C. for 16h for 2 cycles over 2 days at the flowering stage. The figure provides a graph to compare the total weight of seeds (W) in grams harvested after heat stress of control flax plants to various lines transformed with COR78:ROB5 construct.
Figure 11B:
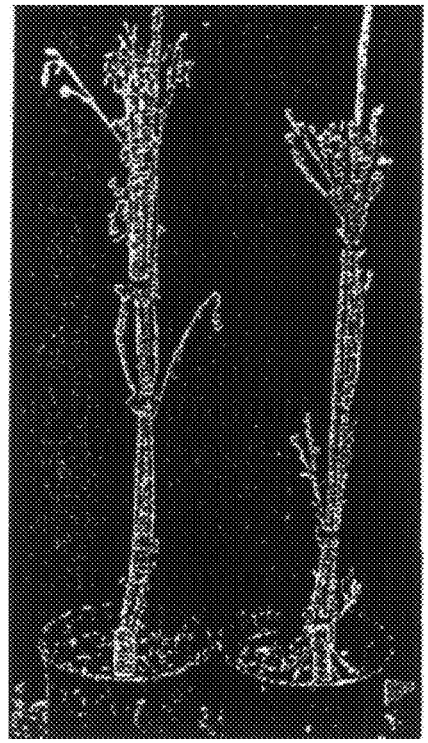
FIG. 11(b) provides comparative photographs of control and COR78:ROB5 transformed line 13467 following heat exposure.

Transgenic Flax Plants Expressing ROB5 Exhibit Increased Tolerance to Heat Compared to Control Plants FIG. 11 shows the effects of heat stress on transgenic flax plants expressing ROB5.Whole plants or plant parts were heated from 22 to 42° C. over a 12 hour period prior to isothermal incubation at 42° C. Viability was assayed by analyzing plant weight. Most transgenic plants showed better recovery and increased seed yields compared to unmodified plants, as measured by the average plant weight (FIG. 11a). FIG. 11b provides comparative photographs for control and COR78:ROB5 transformed line 13467 after heat stress.

EXAMPLE 13

Figure 12A:
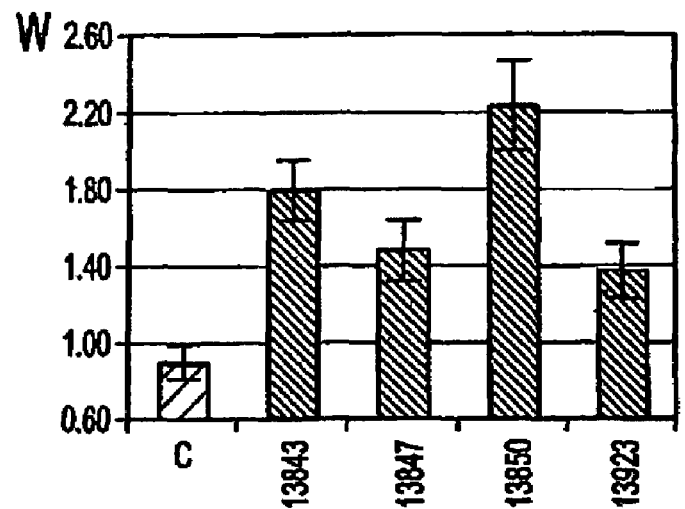
FIG. 12(a) illustrates the effects of ROB5 gene expression in flax, for the purposes of assessing drought tolerance. Moisture loss was assessed over 15 days of drought (no water) conditions. The figure illustrates plant weight (W) for control flax and COR78:ROB5 transformed lines.
Figure 12B:
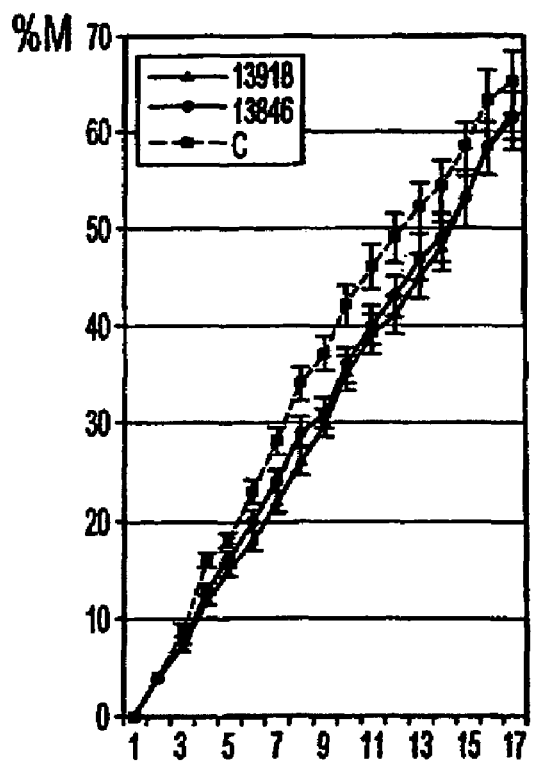
FIG. 12(b) illustrates percentage moisture loss (% M) for seedlings from 1 to 17 days for control and two COR78:ROB5 transformed lines.
Figure 12C:
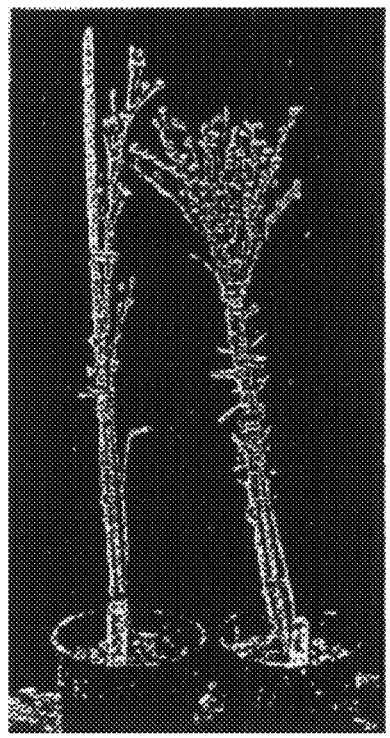
FIG. 12(c) provides comparative photographs of control and COR78:ROB5 transformed plants after extended drought conditions (transformed line 13818).

Transgenic Flax Plants Expressing ROB5 Exhibit Increased Tolerance to Drought Compared to Control Plants FIG. 12 shows the effects of drought stress on transgenic flax plants expressing ROB5. Drought tolerance was determined by withholding water from potted plants (in the three to five leaf stage) for up to 15 days followed by re-watering. The weight of the plants was then measured. In drought studies, ROB5 transgenics were significantly heavier than control plants following drought conditions (FIG. 12a). Moreover, the transformed plants lost moisture at a slower rate than controls (FIG. 12b). FIG. 12c provides comparative photographs of control and transformed plants following exposure to drought conditions.

EXAMPLE 14

Figure 13A:
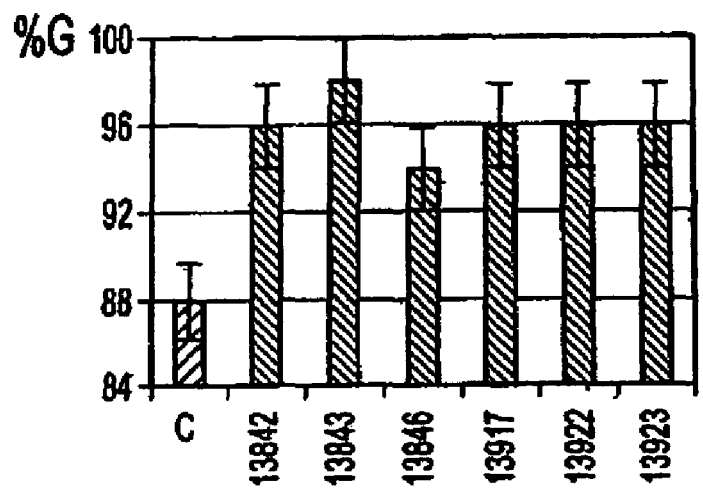
FIG. 13(a) illustrates the effects of ROB5 gene expression in flax, for the purposes of assessing seedling emergence and germination. Seedling germination conditions pertained to 22° C. for 24h, or 8° C. for 3 days, and included control and COR78:ROB5 transformed plants. The figure illustrates percentage germination (% G) of control and transformed lines of seeds after 3 days at 8° C.
Figure 13B:
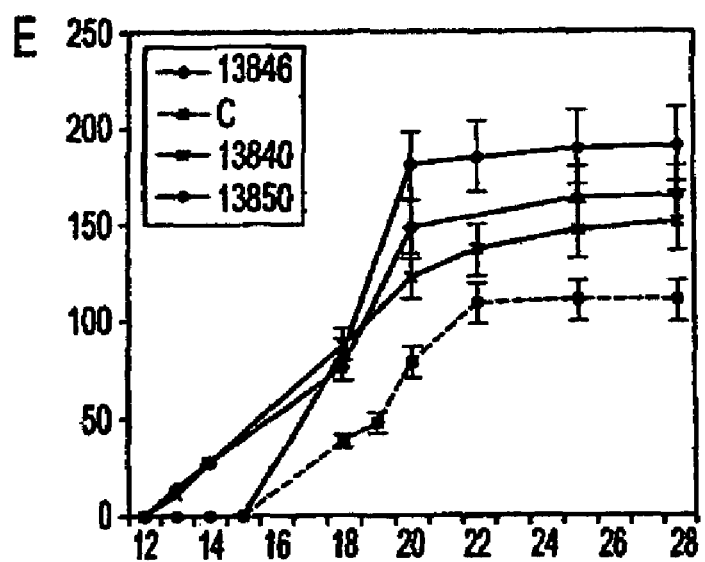
FIG. 13(b) illustrates seedling emergence (E) per meter for control and transformed lines after 12-28 days from planting (field trials).
Figure 13C:
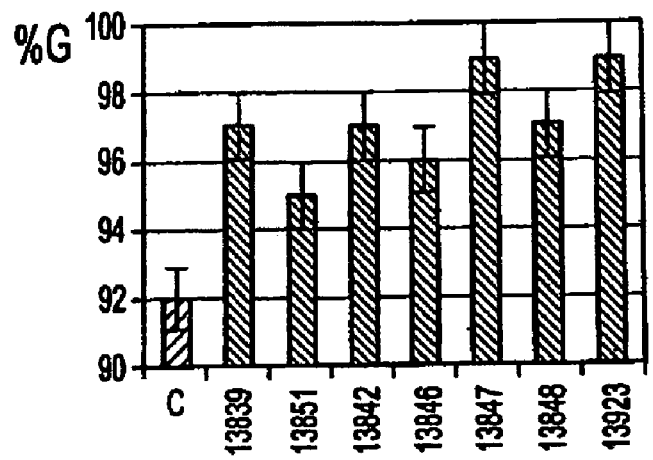
FIG. 13(c) illustrates percentage germination (% G) for control and transformed plants after 24 hours germination time at 22° C.

Transgenic Flax Plants Expressing ROB5 Exhibit Faster Germination and Emergence Compared to Control Plants FIG. 13 compares the germination and emergence characteristics of control and COR78:ROB5 transformed flax plants. FIG. 13a illustrates a significantly higher germination rate for transformed plants compared to control plants following 3 days at 8° C. A higher rate of germination was observed for transformed plants at 22° C. over a 24 hour period (FIG. 13c). Field testing was also conducted, and seedling emergence was more rapid with transgenic lines compared to control plants (FIG. 13b).

EXAMPLE 15

Figure 14A:
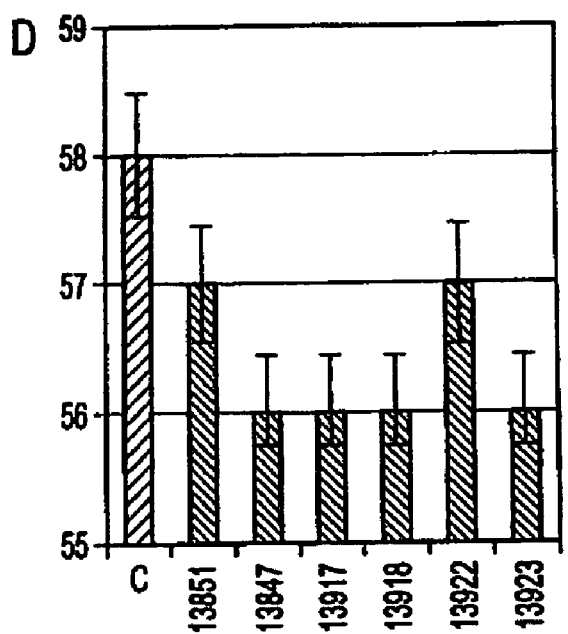
FIG. 14(a) illustrates the effects of ROB5 gene expression in flax, for the purposes of assessing days to flowering and overall yield. Plants were grown in 41 pots outside, and included control and COR78:ROB5 transformed plants. The figure illustrates a comparison of the number of days after planting that control and transformed lines took to flower.
Figure 14B:
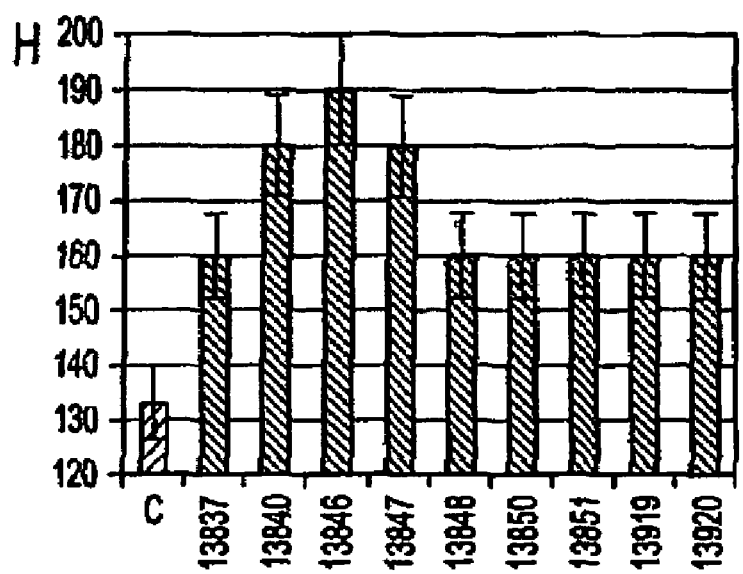
FIG. 14(b) illustrates the height in mm (H) of control and transformed lines 48 days after planting.
Figure 14C:
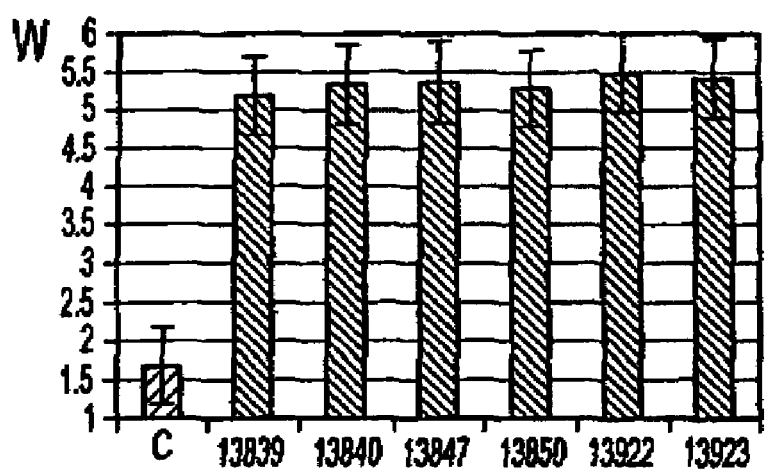
FIG. 14(c) illustrates average weight (in grams) of 1000 kernel seeds harvested from control and transformed plants.
Figure 14D:
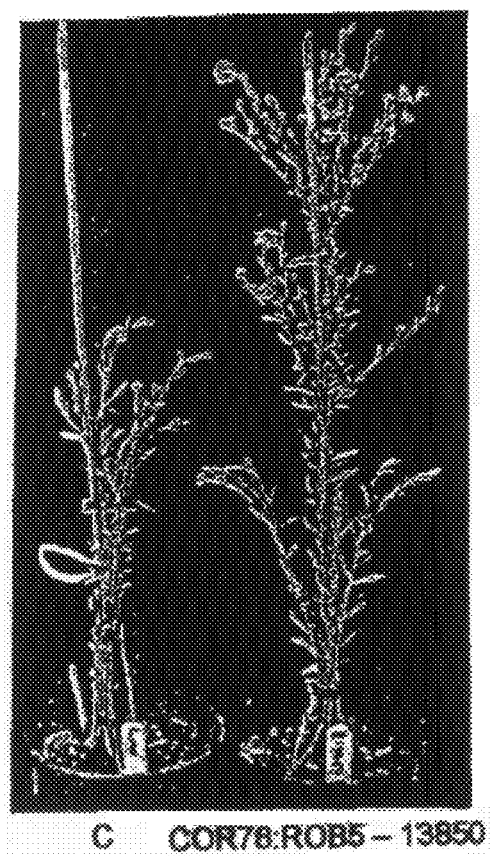
FIG. 14(d) provides comparative photographs of a control flax plant and transformed flax plant line 13850 at 48 days after planting.

Transgenic Flax Plants Expressing ROB5 Flower and Mature More Quickly than Control Plants Compared to Control Plants FIG. 14 compares the flowering and maturation characteristics of control and COR78:ROB5 transformed flax plants Transformed plants flowered more quickly than control plants (FIG. 14a). The transgenic plants were taller than the control plants after a 69 day growing period (FIG. 14b), and in field trials exhibited a much higher 1000 Kernel Seed Weight compared to control plants (FIG. 14c). FIG. 14d provides comparative photographs of a control and transformed COR78:ROB5 plant (line 13850).

EXAMPLE 16

Transgenic Potato Plants Expressing ROB5 Exhibit Increased Tolerance to Frost Compared to Control Plants The following examples provide the results of expressing ROB5 by both constitutive and inducible methods in Desiree potatoes and in the case of freezing tolerance, with a double construct containing ROB5 constitutively expressed and pryrophosphorylase A induced using COR15 (a low temperature inducible promoter). A unique double construct was designed (PsH 737 35S:ROB5+COR15:PPA). This construct results in constitutive expression of the 43 kDa protein and low temperature induction of sucrose. This construct was used in some experiments with potato plants.

Figure 15A:
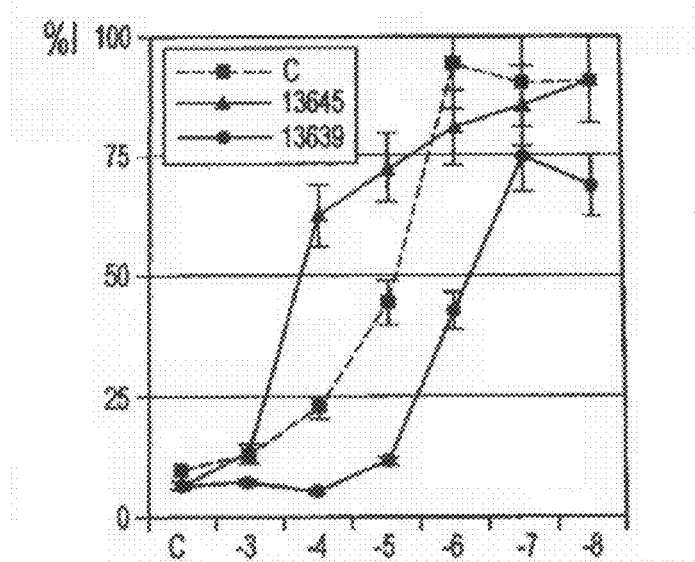
FIG. 15(a) illustrates the effects of ROB5 gene expression in potato, for the purposes of assessing frost tolerance. Plants were incubated at 2° C. (light) and 0° C. (dark) with a 16h photoperiod for 2 days, and then were tested with incubation temperatures as low as −6° C. for 2 cycles over 2 days at the flowering stage. The figure provides a graph to compare percentage ion leakage (% I) for control potato plants to various lines transform with the COR78:ROB5 construct.
Figure 15B:
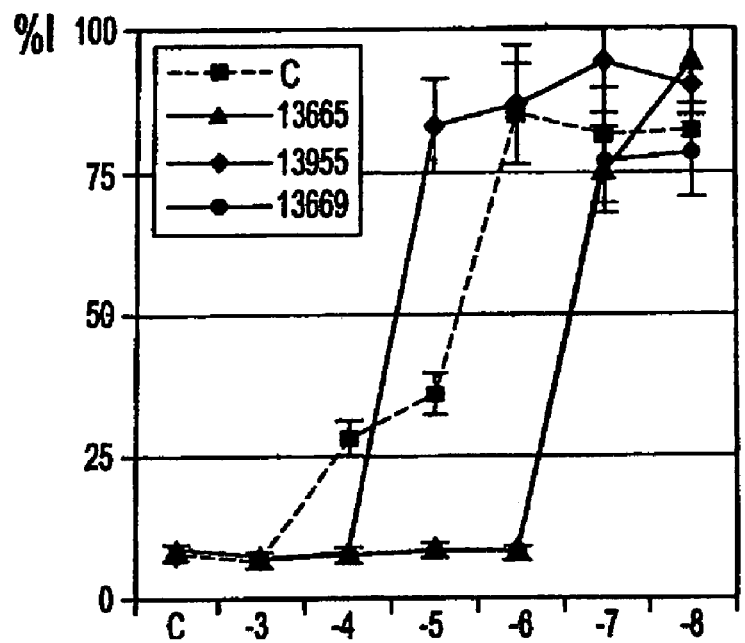
FIG. 15(b) provides a graph to compare percentage ion leakage (% I) for control potato plants to various transformed cell lines.
Figure 15C:
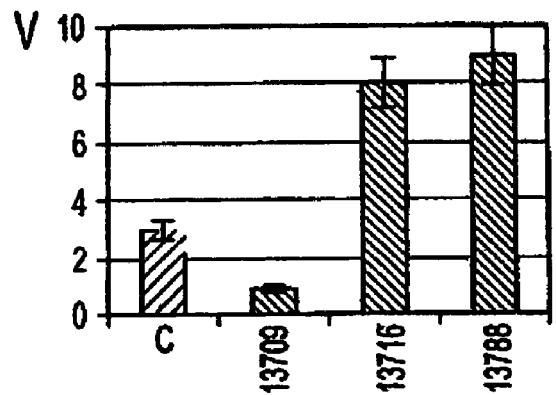
FIG. 15(c) compares a visual assessment of plant survival (V) for control and various transformed plants at −4° C.
Figure 15D:
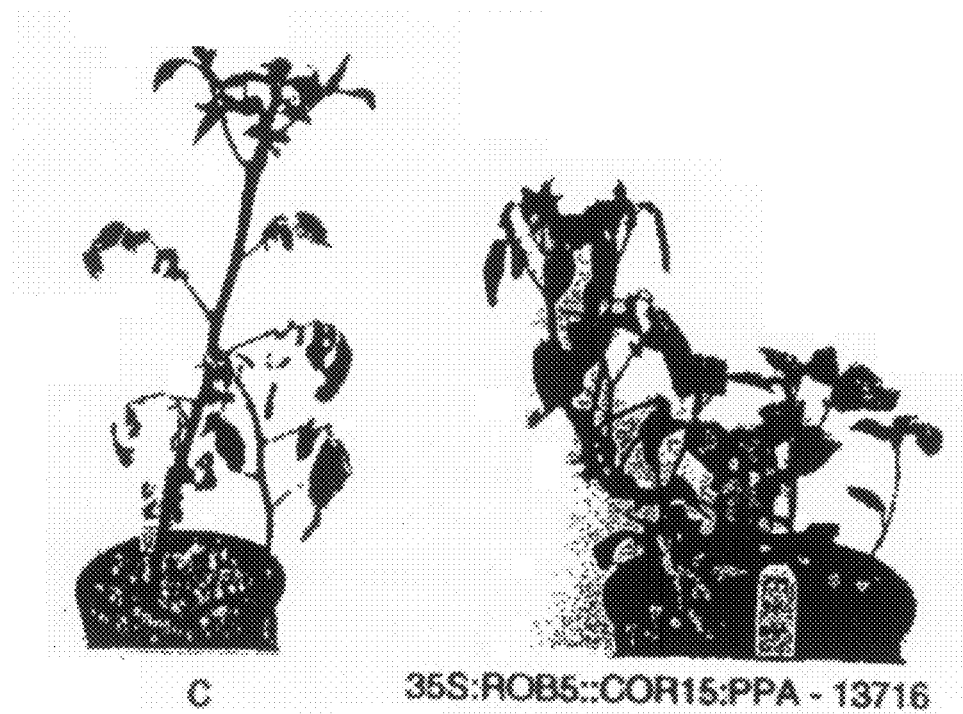
FIG. 15(d) provides comparative photographs of control and 35S:ROB5:COR15:PPA transformed line 13716 following frost exposures.
Figure 15E:
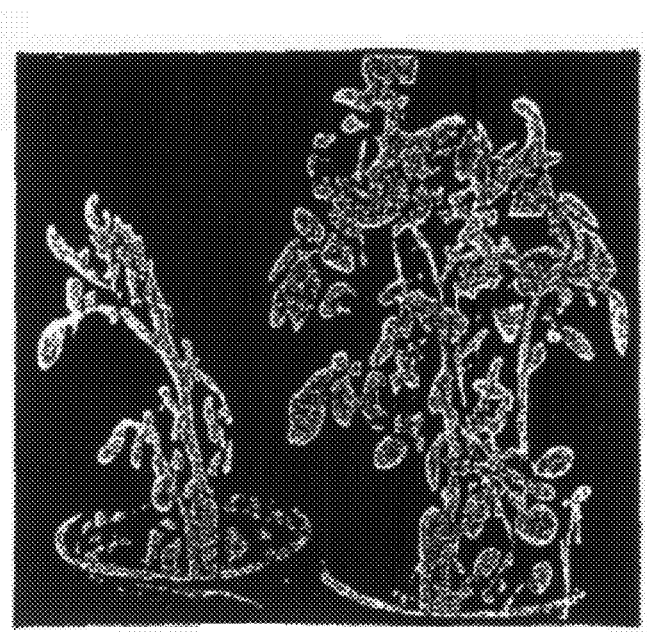
FIG. 15(e) provides comparative photographs of control and COR78:ROB5 transformed line 13669 following frost exposure.

FIG. 15a provides a graph to compare the productivity of selected potato lines transformed with S35:ROB5 and control plants after frost stress testing. Plants were incubated at 2° C. (light) and 0° C. (dark) with a 16 h photoperiod for 2 days, and then were tested with incubation temperatures as low as −9° C. for 2 cycles over 2 days. The results shown in FIGS. 15a and 15b indicate the electrolyte leakage of control potato plants compared to the various lines transformed with the COR78:ROB5 construct. FIG. 15c illustrates a significant increase in survival rates for potato transformed lines 13716 and 13788 following frost stress. The comparative photographs shown in FIGS. 15d and 15e indicate the degree of frost damage in control plants, and relatively little frost damage in transformed lines following frost exposure. In summary, expression of ROB5 in transgenic flax resulted in significant protection against freezing injury.

EXAMPLE 17

Figures 16A, 16B:
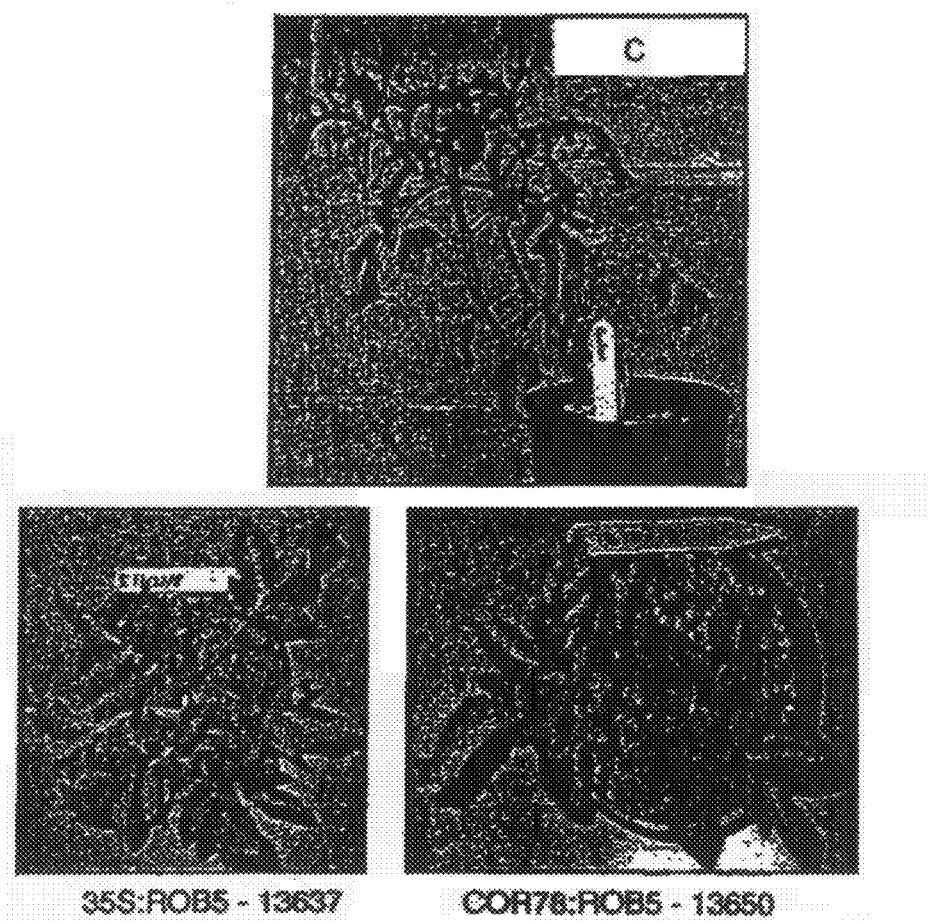
FIG. 16(a) illustrates the effects of ROB5 gene expression in potato, for the purposes of assessing heat tolerance. Plants were incubated at 42° C. for 16h for 2 cycles over 2 days at the flowering stage. The figure illustrates a visual comparison of the degree of frost damage to control and various plant lines transformed with either the 35S:ROB5 or COR78:ROB5 constructs, wherein C=control, P=Visual observation of the degree of frost damage, 0=No damage, +=some damage (50% ion leakage), and ++=heavy damage (>50% ion leakage).
FIG. 16(b) provides comparative photographs of control and 35S:ROB5 transformed plant 13637, and COR78:ROB5 transformed plant 13650 following heat exposure.

Transgenic Potato Plants Expressing ROB5 Exhibit Increased Tolerance to Heat Compared to Control Plants FIG. 16 shows the effects of heat stress on transgenic potato plants expressing ROB5.Whole plants or plant parts were heated from 22 to 42° C. for 16 h, 2 cycles over 2 days at the flowering stage. Viability was assayed initially by visual inspection of control and transformed plants for heat damage (FIG. 16a). FIG. 16b provides comparative photographs for control and COR78:ROB5 or 35S:ROB5 transformed lines after heat stress. The results indicate that ROB5 expression confers heat stress resistance to correspondingly transformed plants.

EXAMPLE 18

Figure 17A:
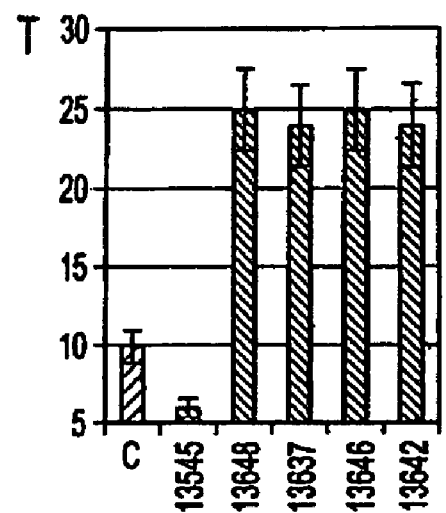
FIG. 17(a) illustrates the effects of ROB5 gene expression in potato, for the purposes of assessing drought tolerance. Moisture loss was assessed over 15 days of drought (no water) conditions. The figure illustrates tuber yield (T) for control potato and 35S:ROB5 transformed lines.
Figure 17B:
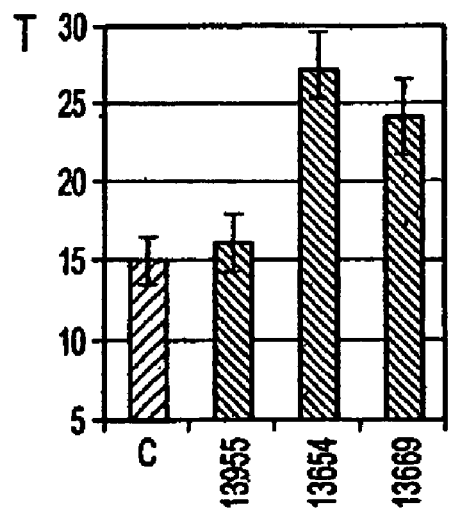
FIG. 17(b) illustrates tuber yield (T) for control potato and COR78:ROB5 transformed lines.
Figure 17C:
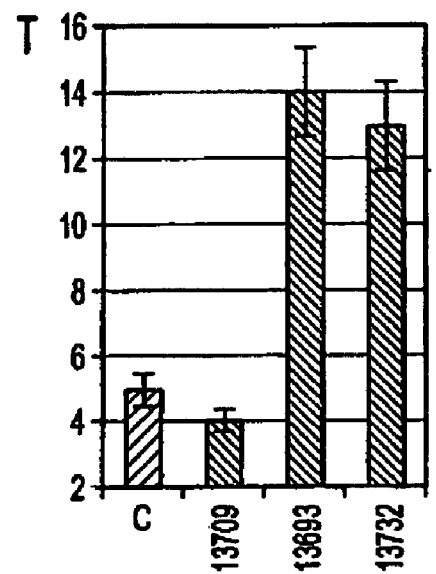
FIG. 17(c) illustrates tuber yield (T) for control potato and 35S:ROB5:COR15:PPA transformed lines.

Transgenic Potato Plants Expressing ROB5 Exhibit Increased Tolerance to Drought Compared to Control Plants FIG. 17 shows the effects of drought stress on transgenic potato plants expressing ROB5. Drought tolerance was determined by withholding water from potted plants for up to 15 days followed by re-watering. The number of tubers harvested from each plant was then measured. In drought studies, ROB5 transgenics tended to exhibit significantly more tubers than control plants following drought conditions regardless of the transformation construct used (FIGS. 17a, 17b and 17c).

EXAMPLE 19

Figure 18A:
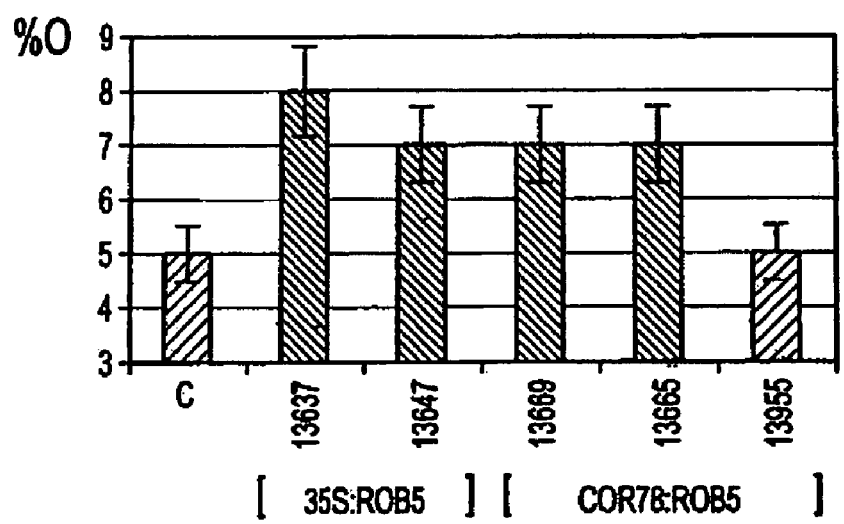
FIG. 18(a) illustrates the effects of ROB5 gene expression in potato, for the purposes of assessing emergence. The figure illustrates percentage hills emerged in the field at 40 days after planting (% D) of control and transformed lines.
Figure 18B:
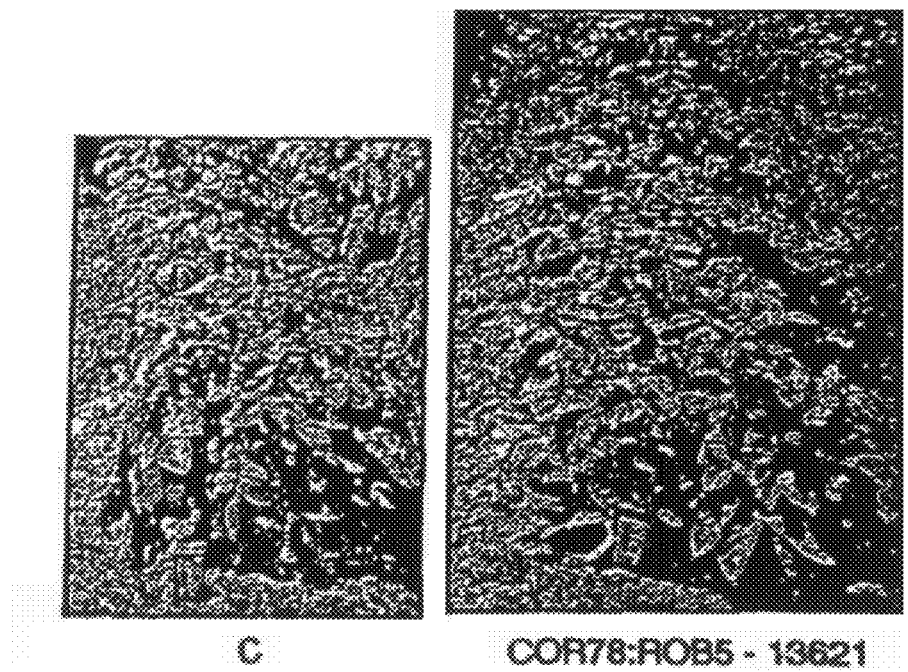
FIG. 18(b) provides comparative photographs of control and COR78:ROB5 transformed plants at 40 days after planting in the field.

Transgenic Potato Plants Expressing ROB5 Exhibit Faster Germination and Emergence Compared to Control Plants FIG. 18 compares the emergence characteristics of control and transformed potato plants. FIG. 18a illustrates a significantly higher emergence rate for transformed potato plants compared to control plants as measured by counting the number of 'hills' emerged in the field at 40 days after planting. FIG. 18b provides comparative photographs of emerged and COR78:ROB5 transgenic plants.

EXAMPLE 20

Figure 19A:
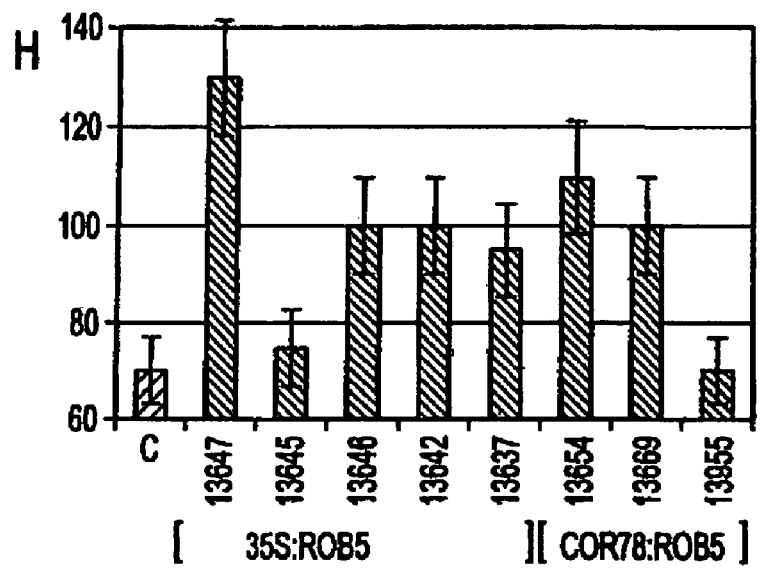
FIG. 19(a) illustrates the effects of ROB5 gene expression in potato, for the purposes of assessing days to niatwity and overall yield. The figure illustrates a comparison of height (H) of control and transformed plants (in mm) 51 days after planting.
Figure 19B:
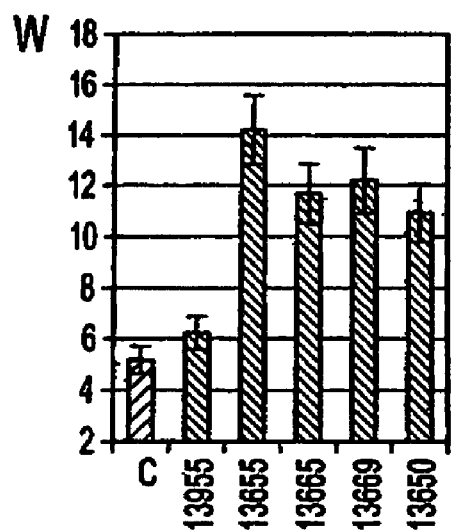
FIG. 19(b) illustrates the total harvested tuber weight (W) (in kg) of control and transformed potato plants 51 days after planting.

Transgenic Potato Plants Expressing ROB5 Mature More Quickly than Control Plants FIG. 19 compares the maturation characteristics of control and transformed potato plants. Transformed plants were significantly taller than control plants (FIG. 19a) and exhibited increased weight compared to control plants (FIG. 19b). These results suggest more rapid maturation of ROB5 transformed potato plants compared to unmodified plants.

EXAMPLE 21

Western Blot Analysis of ROB5 Expression in Transgenic Plants

Figure 20A:
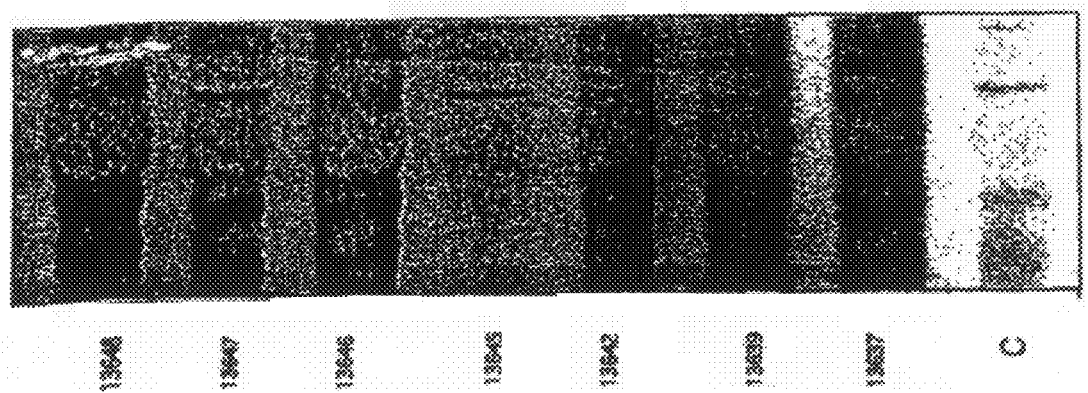
FIG. 20(a) illustrates Western blot analysis of control and potato transgenic lines expressing ROB5 protein (41-43 kDa). The figure shows lines transformed with 35S:ROB5.
Figure 20B:
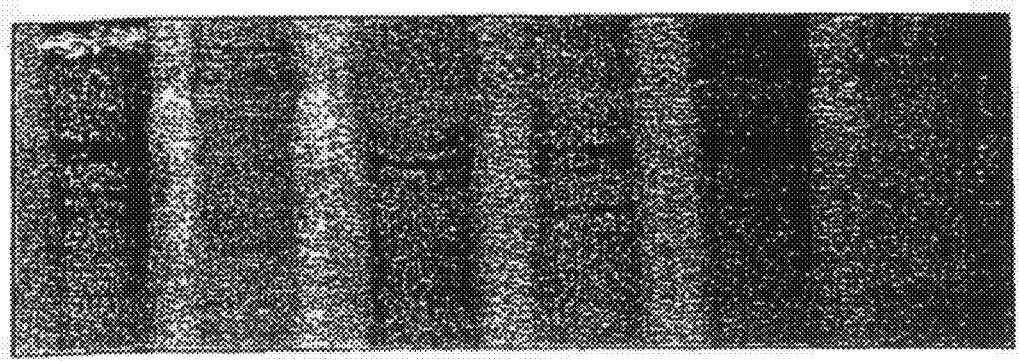
FIG. 20(b) shows lines transformed with COR78:ROB5.
Figure 20C:
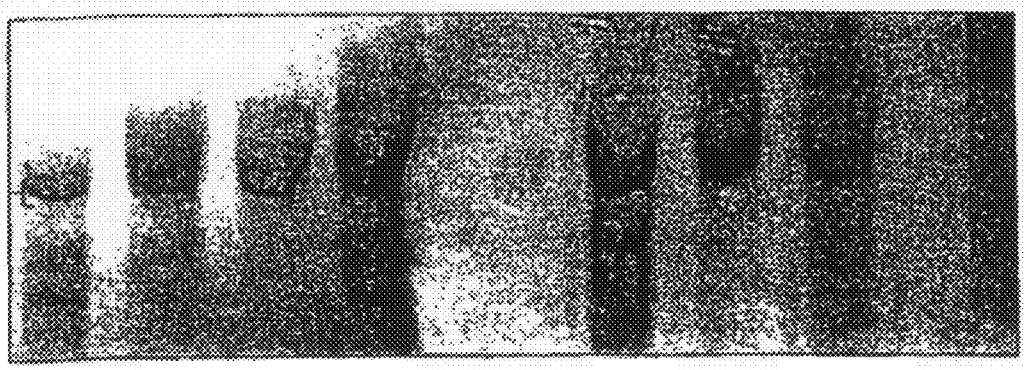
FIG. 20(c) shows lines transformed with 35S:ROB5:COR15:PPA. Aliquots of total soluble protein fractions (60,000×g supernatants) isolated from each line were subjected to one dimensional SDS-PAGE prior to electroblotting and probing with a polyclonal antibody against ROB5 protein. Potato plants were grown in growth chambers prior to harvesting leaves for protein isolation. COR78 and COR15 were cold acclimated at 8° C. 16 hour photoperiod for 4 days.

FIG. 20 provides Western blots to analyse the exogenous expression of ROB5 in various transgenic plant lines. Transgenic potato isolates (construct 35S:ROB5) 13646 and 13637 (FIG. 20a) show strong expression of the 43 kDa protein and increased tolerance to heat, which correlates to an increased tolerance to heat stress. Transgenic isolate 13645 (FIG. 20a) shows very poor or no expression of the 43 kDa protein and heat tolerance similar to the control. Expression of ROB5 with the COR78 promoter (FIG. 20b) shows similar results. Isolate 13955 showed poor heat tolerance and very low levels of expression, whereas isolates 13650 and 13665 showed significant levels of 43 kDa proteins (FIG. 20b) and increased heat tolerance. Transgenic isolated 13788 and 13716 transformed with 35S:ROB5:COR15:PPA and expressing the 43 kDa protein (FIG. 20c) in combination with increased sucrose levels show high levels of frost tolerance. Transgenic isolate 13709 shows no frost tolerance and no detectable expression of the 43 kDa protein (FIG. 20c). These observations correlate the expression of ROB5 with enhanced abiotic stress tolerance and confirm the function of the 43 kDa protein in increasing tolerance to frost and heat.

EXAMPLE 22

Expression of ROB5 in Other Species (Western Blots)

Figure 21A:
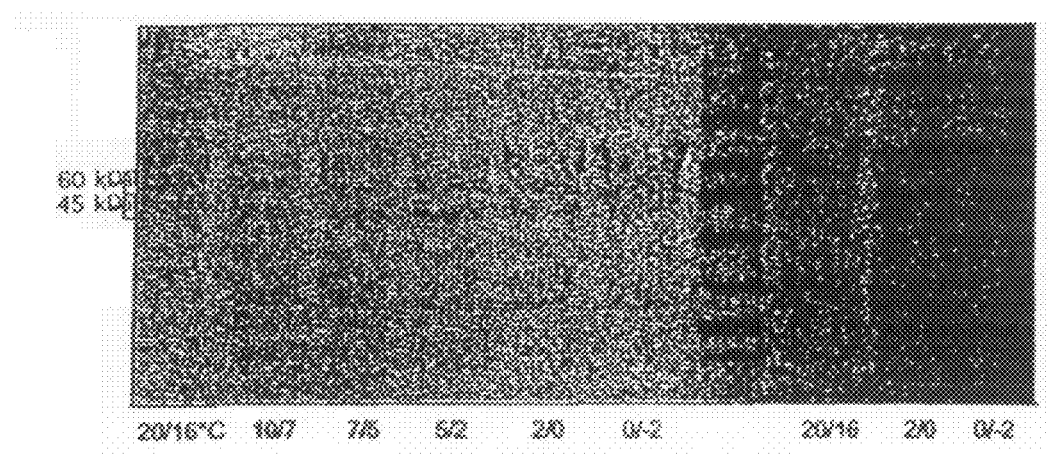
FIG. 21(a) provides Western blot analysis of spring canola cv. Quest.
Figure 21B:
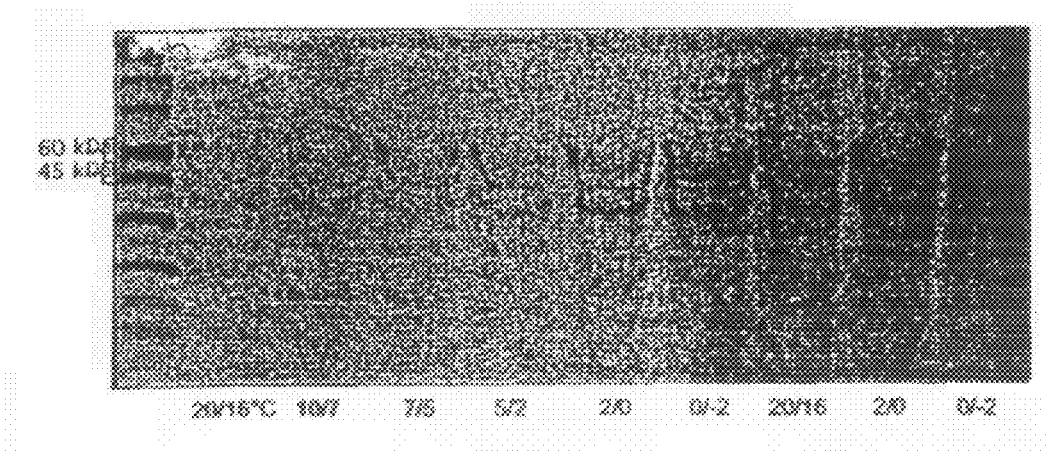
FIG. 21(b) provides winter canola cv. Express.
Figure 21C:
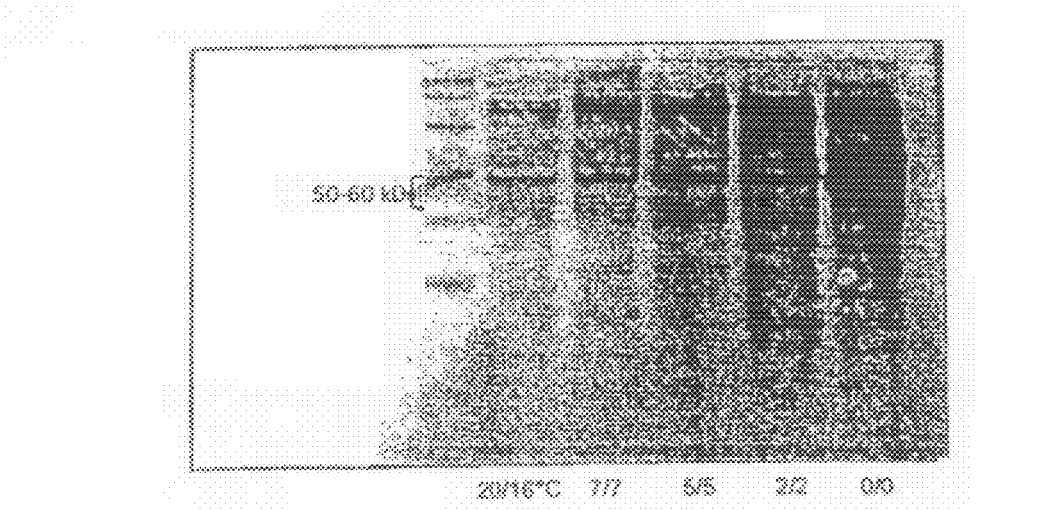
FIG. 21(c) provides spring wheat cv. Katepwa to assay for the expression of ROB5 or immunoreactive homologues thereof.
Figure 22A:
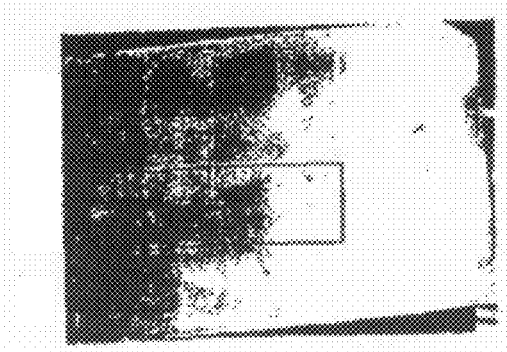
FIG. 22(a) illustrates 2D SDS-PAGE and electroblotting experiments to provide evidence for ROB5 homologues in species other than Bromegrass. Blots were derived from flax (*Linum usitatissimum*) cv. Norwin.
Figure 22D:
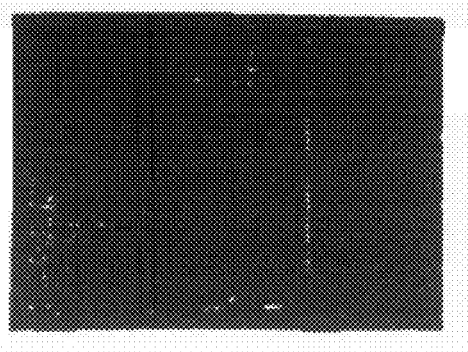
FIG. 22(d) illustrates 2D SDS-PAGE and electroblotting experiments to provide evidence for ROB5 homologues in species other than Bromegrass. Blots were derived from tomato (*Lycopersicon lycopersicum*).
Figure 22B:
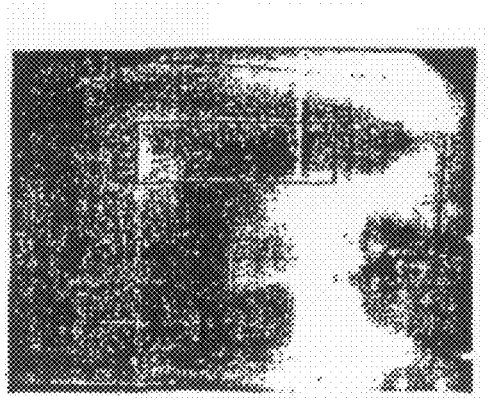
FIG. 22(b) illustrates 2D SDS-PAGE and electroblotting experiments to provide evidence for ROB5 homologues in species other than Bromegrass. Blots were derived from barley (*Hordeum vulgare*) cv. Harrington.
Figure 22E:
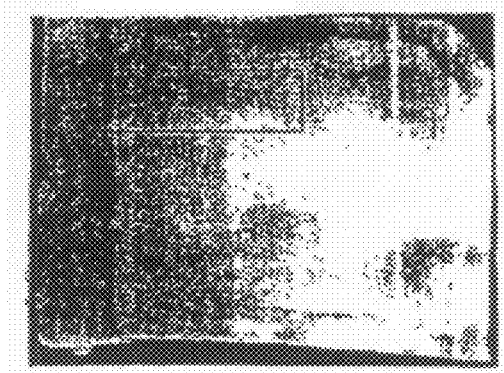
FIG. 22(e) illustrates 2D SDS-PAGE and electroblotting experiments to provide evidence for ROB5 homologues in species other than Bromegrass. Blots were derived from cucumber (*Cucumis sativus*).
Figure 22C:
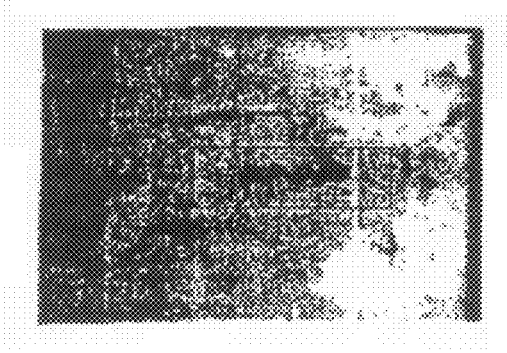
FIG. 22(c) illustrates 2D SDS-PAGE and electroblotting experiments to provide evidence for ROB5 homologues in species other than Bromegrass. Blots were derived from Tobacco (*Nicotiana tabacum*).
Figure 22F:
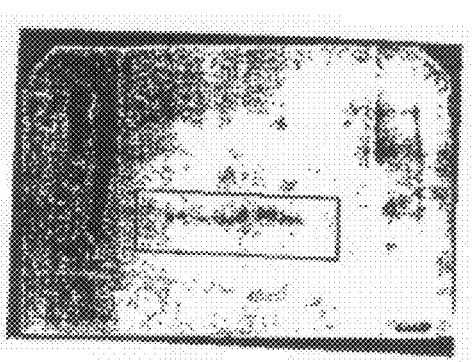
FIG. 22(f) illustrates 2D SDS-PAGE and electroblotting experiments to provide evidence for ROB5 homoloanes in species other than Bromegrass. Blots were derived from bromegrass (*Bromus inermus*) cv. Leyss.

The Western blots shown in FIG. 21 illustrate that ROB5 gene homologues are expressed in two very different plant species (including monocots and dicots). Each lane represents protein extracted from a different cold acclimation treatment of spring canola cv. Quest (FIG. 21a), winter canola cv. Express (FIG. 21b), or spring wheat cv. Katepwa (FIG. 21c), showing ROB5 homologous protein levels. ROB5 when isolated from bromegrass has a apparent molecular weight of 43 kDa. However due to the dye used to visualize the ladder, the band representing ROB5 is in the 50-60 kDa range (red band is 60 kDa). The SDS concentration was low in the gels therefore ROB5 may have remained in the dimer form, represented by the band at the top of each gel. A standard Western blot protocol was used. Protein was extracted with a borate buffer (Wisniewski et al., Planta vol:96), run on a 4-12% polyacrylamide gel, then transferred to a membrane using the Bio-Rad mini Protean II electrophoresis system. A ROB5 antibody raised in rabbits was used to probe the membrane, and alkaline phosphatase goat anti-rabbit antibodies were used to probe ROB5. Skim milk was used as a protein source in the blocking solution, versus Bovin Serum Albumin (BSA). Membranes were developed using NBT/BCIP as the developing agent.

EXAMPLE 23

2D Electrophoresis and Electroblotting

Proteins were extracted from cells of various plant species, and samples were loaded onto a 2D protein separation apparatus. Proteins were first separated according to their isoelectric point (horizontal axis for each blot), and subsequently separated according to molecular size by SDS-PAGE. Typically, protein was then blotted onto polyvinylidene fluoride (PVDF) membranes according to standard protocols. The blots were probed with a rabbit polyclonal antisera raised to synthetic ROB5, followed by a goat anti-rabbit antibody. Regions of bound antibody were visualized using an alkaline phosphatase developing solution comprising 5-Bromo-4-chloro-3-indoyl phosphate (BCIP) and nitrotetrazolium blue chloride (NBT).

The blots shown in FIG. 22 were derived from various plant species including (a) flax (*Linum usitatissium*) cv. Norwin, (b) barley (*Hordeum vulgare*) cv. Harrington, (c) Tobacco (*Nicotiana tabacum*), (d) tomato (*Lycopersicon lycopersicum*), (e) cucumber (*Cucmis sativus*), and (f) bromegrass (*Bromus inermus*) cv. Leyss. All blots presented multiple 'spots' that react with the antibody raised to the ROB5 protein. The multiple spots suggests various isoforms of ROB5, and provide strong evidence of ROB5 homologues in species other than Bromegrass.

The results discussed in Examples 22 and 23 demonstrate the expression of ROB5 homologues in a variety of plant species, and such ROB5 homologous genes and proteins are intended to fall within the scope of the present invention. Moreover, it is considered highly likely that exogenous expression of such ROB5 genes will give rise to similar improvements in stress tolerance and plant growth/vigor in plant species other than canola, flax, and potato. For example, the capacity of ROB5 expression to improve cold tolerance in plants may permit tropical plant species to be cultivated successfully in more temperate climates. Likewise, the capacity of ROB5 expression to improve heat tolerance in plants may permit temperate plant species to be growth in hotter, perhaps tropical conditions. It is intended to encompass all of such transgenic plants expressing ROB5 genes and derivatives thereof within the scope of the present invention.

The invention further encompasses non-plant transgenic organisms including for example insects, mammals and fish, wherein advantageous characteristics are conferred to the organisms. For example, transgenic fish expressing ROB5 may be expected to exhibit an increased tolerance to adverse environmental conditions including but not limited to excessive heat, cold, or toxins. Moreover, the invention encompasses transformed yeast strains expressing ROB5, and exhibiting superior industrial applications including, but not limited to increased fermentation temperatures, higher alcohol concentrations etc.

ADDITIONAL EXAMPLES

Field Trail Evaluations of Transgenic Plants at Multiple Field Sites

Site Locations and Trial Setup

Canola and flax PNT lines were tested in five field trails during the 2002 growing season. In terms of environmental factors, two of the sites were considered mildly stressed-to-stressed (hereinafter termed "non-stressed" sites) located in Manitoba, Canada. Two other sites located in Saskatchewan, Canada were considered moderately to severely stressed (hereinafter termed "stressed" sites). Another site located in Alberta, Canada was considered "severely stressed". Each field trail was set up using Randomized Complete lock Design (RCBD) with four replications. The lines were planted in rows, at a minimum of 20 plants per row, in standard commercial spacing. In addition to controls, an empty vector and a commercial variety were included in each of the trials.

Canola PNT ROB5 lines were also tested in three replicated field trials in the 2003 growing season. In 2003, the canola PNT ROB5 lines were further tested in three locations: one considered non-stressed (Manitoba, Canada), and two considered stressed (Saskatchewan, Canada). Each field trial was set up using Randomized Complete Block Design (RCBD) with two replications. The lines were planted in four rows, at a minimum of 20 plants per row, in standard commercial spacing. One control (empty vector) was included in each trial. Individual florets in this canola trial were not "bagged". Standard seed treatments were applied to all seed. The field locations of all trials were located in commercial flax and canola production regions across western Canada. None of the sites chosen had been planted with flax or canola in the previous year.

The following examples pertain to data collected for each field trial in addition to daily and weekly monitoring activities conducted in accordance with PBO/CFIA regulations. Any noticeable differences between the transgenic and non-transgenic (control) plants in terms of phenotype and/or agronomic traits was also recorded, and photographed if possible. All florets were "bagged" to ensure selfing of each canola plant and the controls. All seed was harvested at full maturity and weighed for each plant. Weather data was collected for all trial locations including, but not limited to, soil temperatures at planting and emergence, ambient temperatures, rainfall occurrences, and amount, relative humidity etc.

EXAMPLE 24

Enhanced Emergence of Transformed Canola Lines at Non-Stressed Sites (MacGregor, MB, and Portage la Prairie, MB)

Figure 23A:
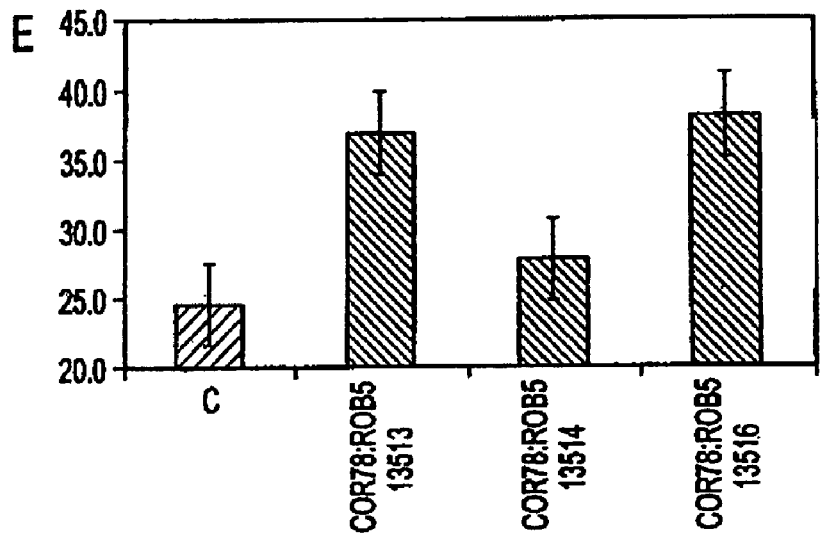
FIG. 23(a) illustrates enhanced emergence of COR78:ROB5 transformed canola plants compared to control plants at 'non-stressed' sites. The graph shows average number of emerged seedlings per meter of seeded ground (B) at MacGregor, MB.
Figure 23B:
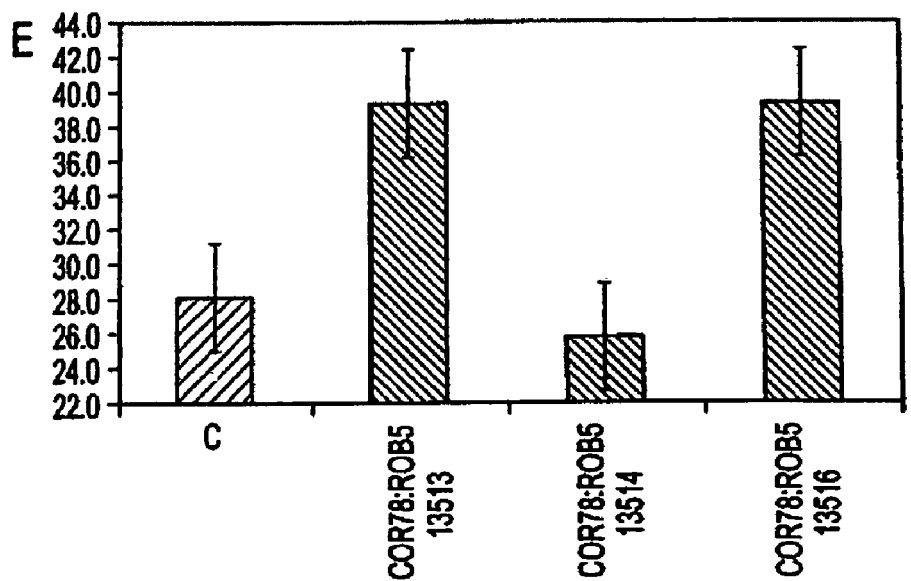
FIG. 23(b) shows average number of emerged seedlings per meter of seeded ground (E) at Portage la Prairie.

FIG. 23 illustrates enhanced emergence of COR78:ROB5 transformed plants compared to control plants at 'non-stressed' sites. (a) graph shows average number of emerged seedlings per meter of seeded ground (E) at MacGregor, MB, and (b) graph shows average number of emerged seedlings per meter of seeded ground (E) at Portage la Prairie, MB. Two COR78:ROB5 transformed lines(13513 and 13516) exhibited a significant increase in rate of emergence for seedlings compared to control seedlings at non-stressed sites.

EXAMPLE 25

Enhanced Growth and Development of Transformed Canola Lines at Non-Stressed Sites (MacGregor, MB, and Portage la Prairie, MB)

Figure 24A:
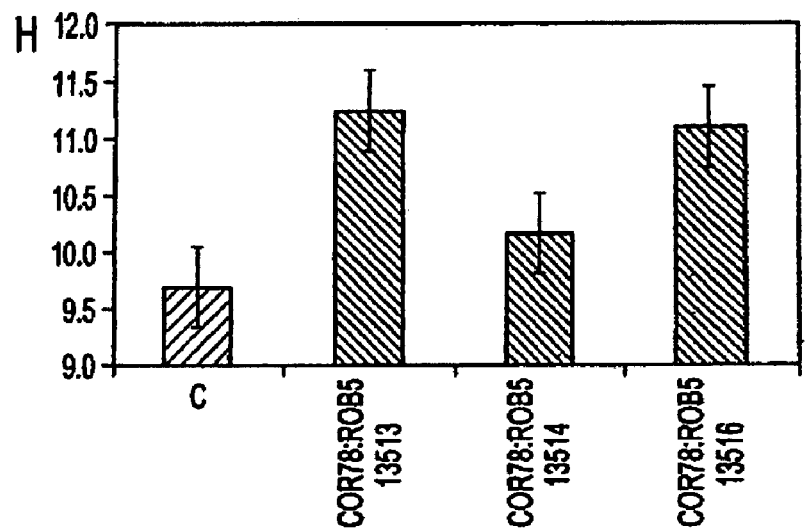
FIG. 24(a) illustrates enhanced growth and development of COR78:ROB5 transformed canola plants compared to control plants at 'non-stressed' sites at 3 weeks after emergence. The graph shows average height of seedlings H (in cm) for trials at MacGregor, MB.
Figure 24B:
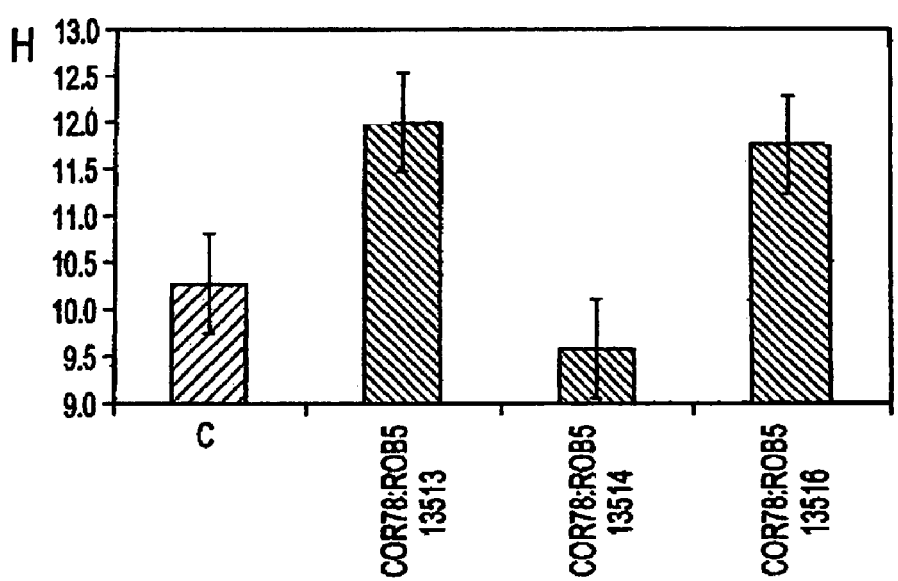
FIG. 24(b) shows average height of seedlings (H in cm) for trials at Portage la Prairie.

FIG. 24 illustrates enhanced growth and development of COR78:ROB5 transformed plants compared to control plants at 'non-stressed' sites at 3 weeks after emergence. (a) graph shows average height of seedlings (H in cm) for trials at MacGregor, MB, and (b) graph shows average height of seedlings (H in cm) for trials at Portage la Prairie, MB. Two COR78:ROB5 transformed lines(13513 and 13516) exhibited a significant increase in seedling height at 3 weeks after emergence compared to control seedlings at non-stressed sites.

EXAMPLE 26

More Rapid Flowing of Transformed Canola Lines at Non-Stressed Sites (MacGregor, MB, and Portage la Prairie, MB)

Figure 25A:
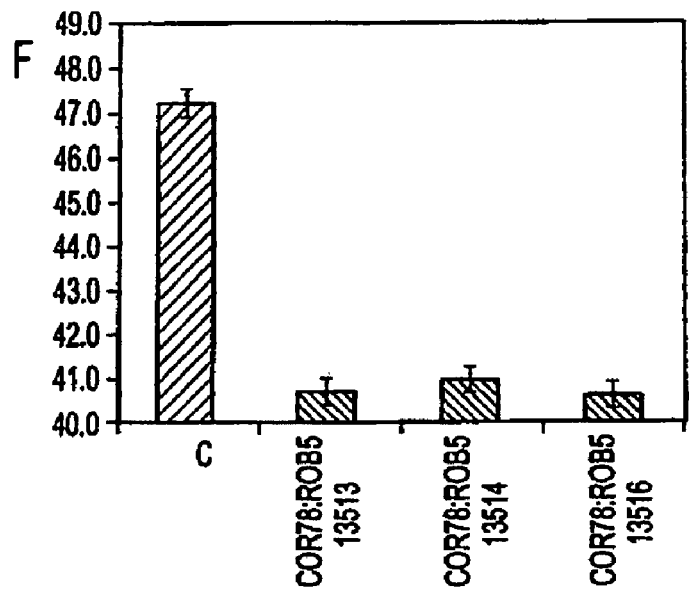
FIG. 25(a) illustrates enhanced maturity and decreased number of days to flowering of COR7:ROB5 transformed canola plants compared to control plants at 'non-stressed' sites. The graph shows average time to flowering (F) (days after planting) for trials at MacGregor, MB.
Figure 25B:
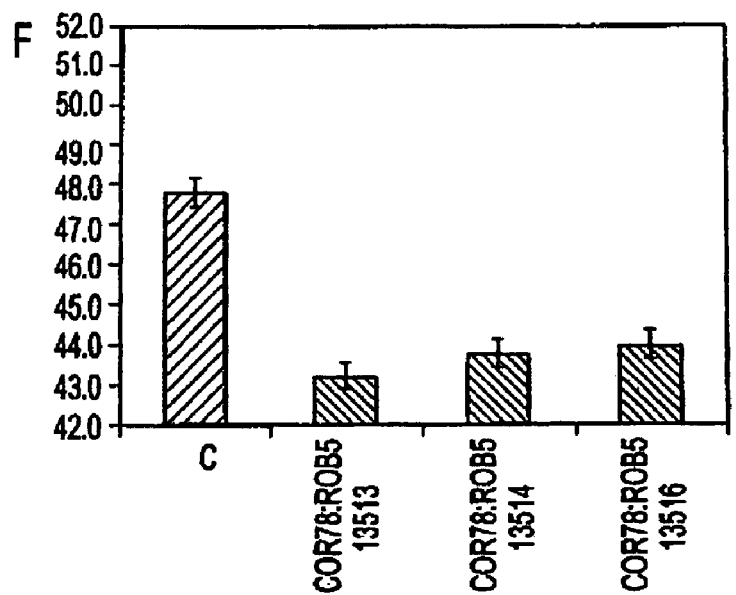
FIG. 25(b) shows time to flowering (F) (days after planting) for trials at Portage la Prairie.
Figure 26A:
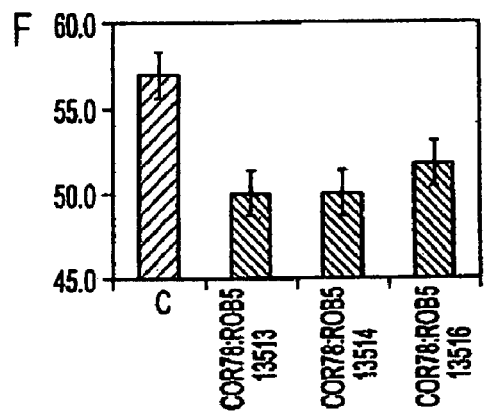
FIG. 26(a) illustrates enhanced maturity and decreased number of days to flowering of COR78:ROB5 transformed canola plants compared to control plants at 'stressed' sites. The graph shows average time to flowering (F) (days after planting) for trials at Wakaw, SK.
Figure 26B:
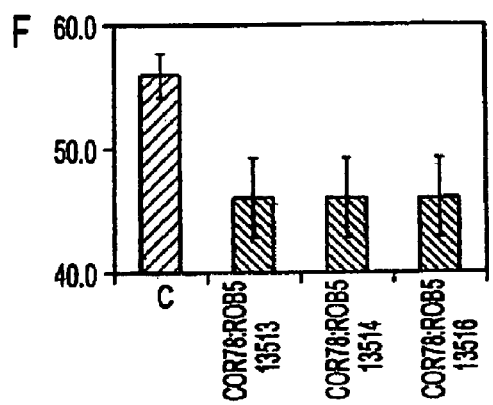
FIG. 26(b) shows time to flowering (F) (days after planting) for trials at Aberdeen, SK.
Figure 26C:
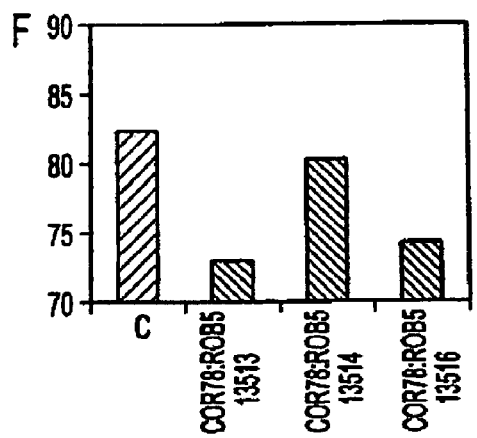
FIG. 26(c) shows average time to flowering (F) (days after planting) for trials at Saskatoon, SK.
Figure 26D:
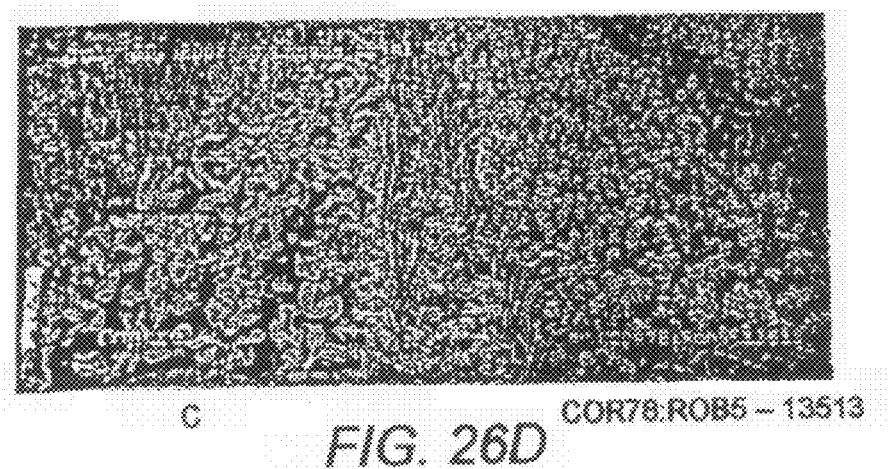
FIG. 26(d) is a comparative photograph of plants growth for FIG. 26(c), control plants shown in the left-hand row, and transgenic (13513) plants shown in the right hand row (note that florets were not "bagged" for this experiment).

FIG. 25 illustrates enhanced maturity and decreased number of days to flowering of COR78:ROB5 transformed plants compared to control plants at 'non-stressed' sites. (a) graph shows average time to flowering (F) (days after planting) for trials at MacGregor, MB, and (b) graph shows time to flowering (F) (days after planting) for trials at Portage la Prairie. Three COR78:ROB5 transformed lines (13513, 13514, and 13516) exhibited more rapid progression to flowing (after planting) compared to control seedlings at non-stressed sites.

EXAMPLE 27

More Rapid Flowing and Progression to Maturity of Transformed Canola Lines at Stressed Sites (Wakaw, SK, and Aberdeen, SK)

FIG. 26 illustrates enhanced maturity and decreased number of days to flowering of COR78:ROB5 transformed plants compared to control plants at 'stressed' sites. (a) graph shows average time to flowering (F) (days after planting) for trials at Wakaw, SK, (b) graph shows time to flowering (F) (days after planting) for trials at Aberdeen, SK, and (c) graph shows average time to flowering (F) (days after planting) for trials at Saskatoon, SK, and (d) comparative photograph of plants growth for (c), control plants shown in the left-hand row, and transgenic (13513) plants shown in the right hand row (note that florets were not "bagged" for this experiment). Three COR78:ROB5 transformed lines(13513, 13514, and 13516) exhibited more rapid progression to flowing (after planting) compared to control seedlings at stressed sites.

EXAMPLE 28

Enhanced Maturity at Harvest Time for Transformed Canola Lines at Non-Stressed Sites (MacGregor, MB, and Portage la Prairie, MB)

Figure 27A:
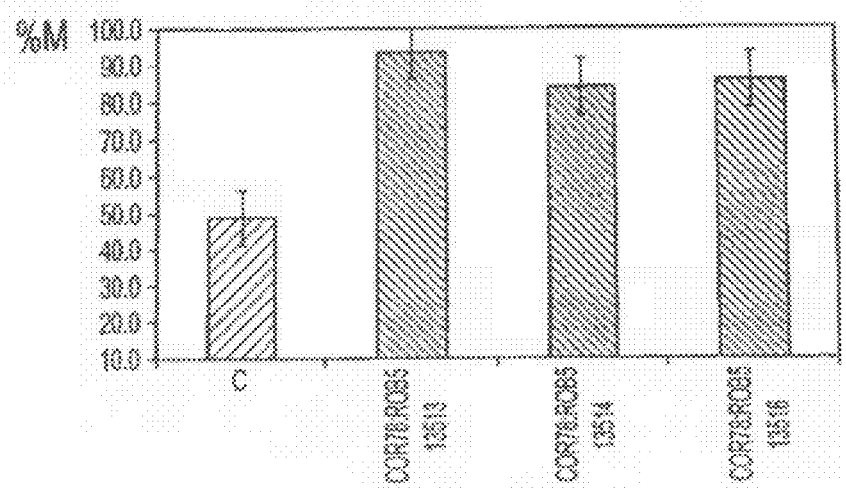
FIG. 27(a) illustrates enhanced maturity at harvest time for COR78:ROB5 transformed canola plants compared to control plants at 'non-stressed' sites. The graph shows average penentage maturity (% M) for trials at MacGregor, MB.
Figure 27B:
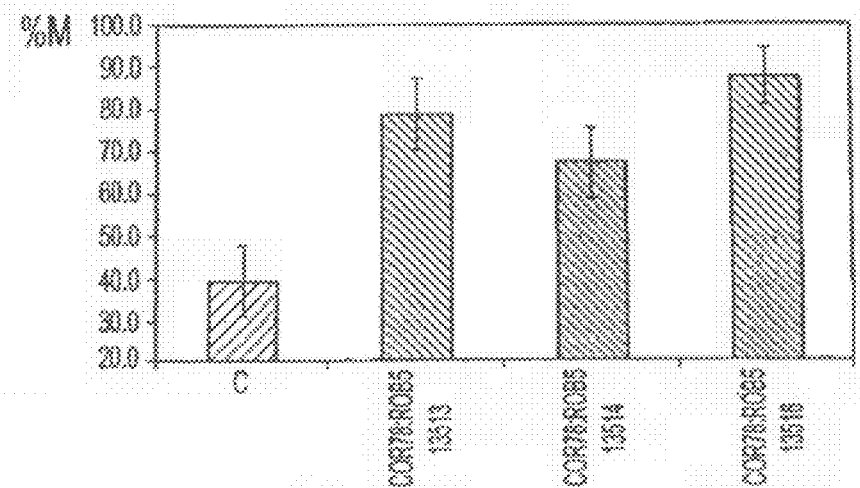
FIG. 27(b) shows average percentage maturity (% M) for trials at Portage la Prairie, MB.

FIG. 27 illustrates enhanced maturity at harvest time for COR78:ROB5 transformed plants compared to control plants at 'non-stressed' sites. (a) graph shows average percentage maturity (% M) for trials at MacGregor, MB, and (b) graph shows average percentage maturity (% M) for trials at Portage la Prairie. All three COR78:ROB5 transformed lines (13513, 13514, and 13516) exhibited significantly higher maturity compared to control plants.

EXAMPLE 29

Enhanced Maturity at Harvest Time for Transformed Canola Lines at Stressed Site (Saskatoon, SK)

Figure 28A:
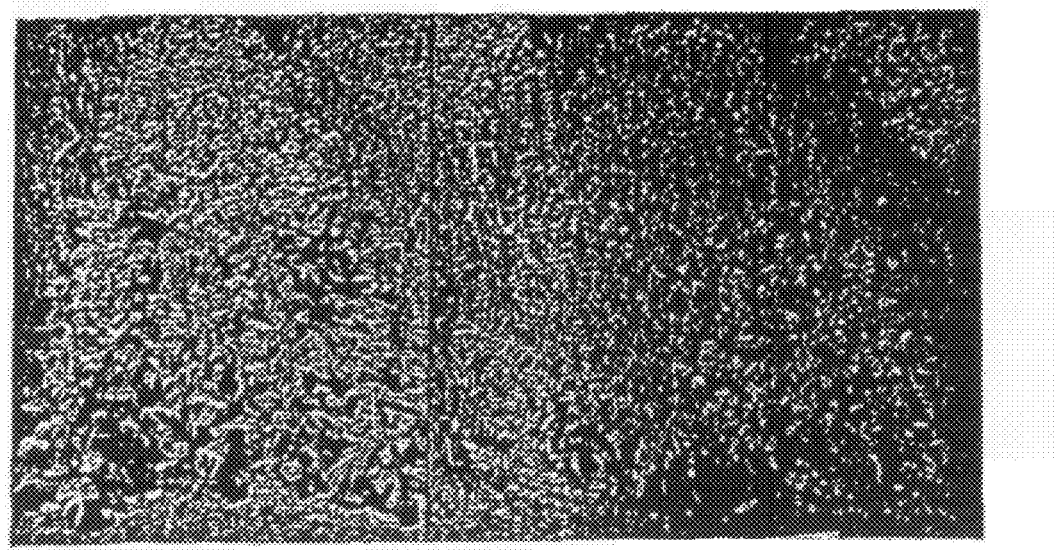
FIG. 28(a) illustrates enhanced maturity at harvest time for COR78:ROB5 transformed canola plants compared to control plants (at a 'stressed' site). The figure provides comparative photographs for control and transformed plants (line 13513) on Aug. 8, 2003.
Figure 28B:
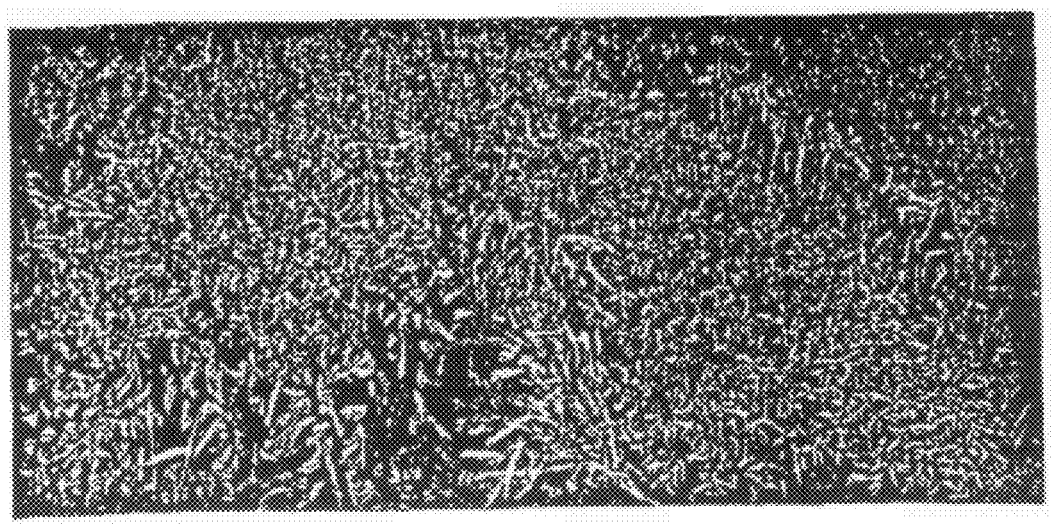
FIG. 28(b) provides comparative photographs for control and transformed plants (line 13513) on Sep. 26,2003. Note increased vigor and pod development for the transformed plants.

FIG. 28 illustrates enhanced maturity at harvest time for COR78:ROB5 transformed plants compared to control plants at a 'stressed' site. (a) provides comparative photographs for control and transformed plants (line 13513) on August 8, and (b) provides comparative photographs for control and transformed plants (line 13513) on Sep. 26, 2003. Note increased vigor and pod development for the transformed plants.

EXAMPLE 30

Enhanced Pod-Fill of Transformed Canola Lines at Non-Stressed Sites (MacGregor, MB, and Portage la Prairie, MB)

Figure 29A:
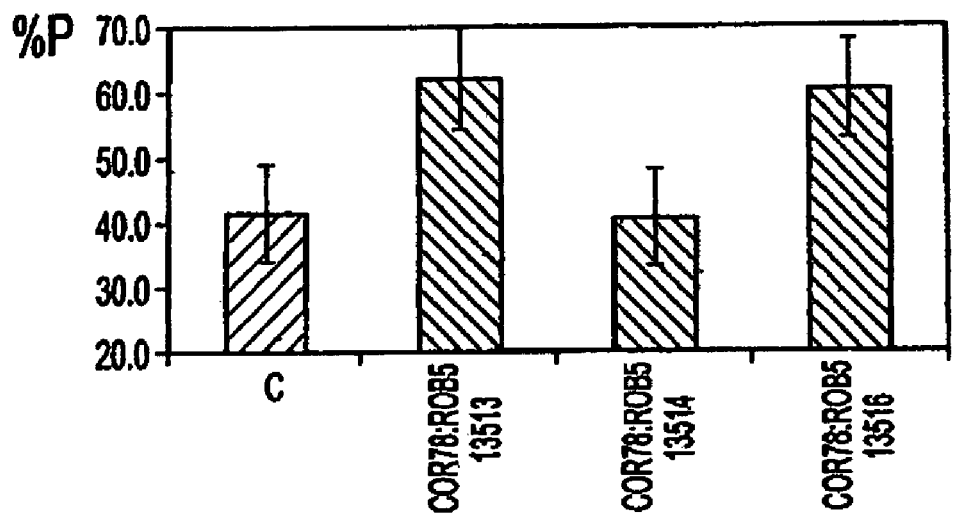
FIG. 29(a) illustrates enhanced pod fill for COR78:ROB5 transformed plants compared to control canola plants at 'non-stressed' sites. The graph shows average percentage pod fill (% P) for trials at MacGregor, MB.
Figure 29B:
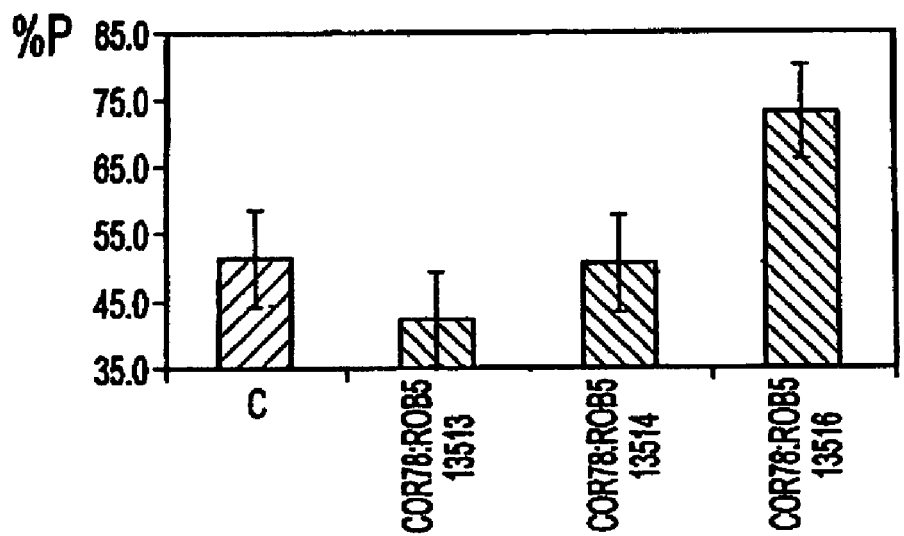
FIG. 29(b) shows average pod fill (% P) for trials at Portage la Prairie, MB.

FIG. 29 illustrates average pod fill for COR78:ROB5 transformed plants compared to control plants at 'non-stressed' sites. (a) graph shows average percentage pod fill (% P) for trials at MacGregor, MB, and (b) graph shows average pod fill (% P) for trials at Portage la Prairie. In particular, line 13516 exhibited significantly higher percentage pod fill at both non-stressed sites.

EXAMPLE 31

Enhanced Pod-Fill of Transformed Canola Lines at a Stressed Site (Aberdeen, SK) and a Severely Stressed Site (Nisku, AB)

Figure 30A:
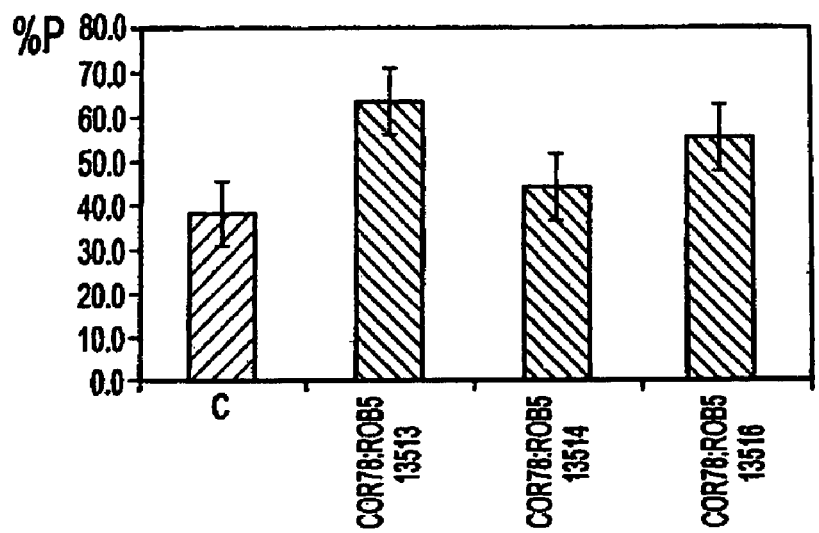
FIG. 30(a) illustrates enhanced pod fill for COR78:ROB5 transformed plants compared to control canola plants at 'stressed' or 'very-stressed' sites. The graph shows average percentage pod fill (% P) far trials at Aberdeen, SK (stressed).
Figure 30B:
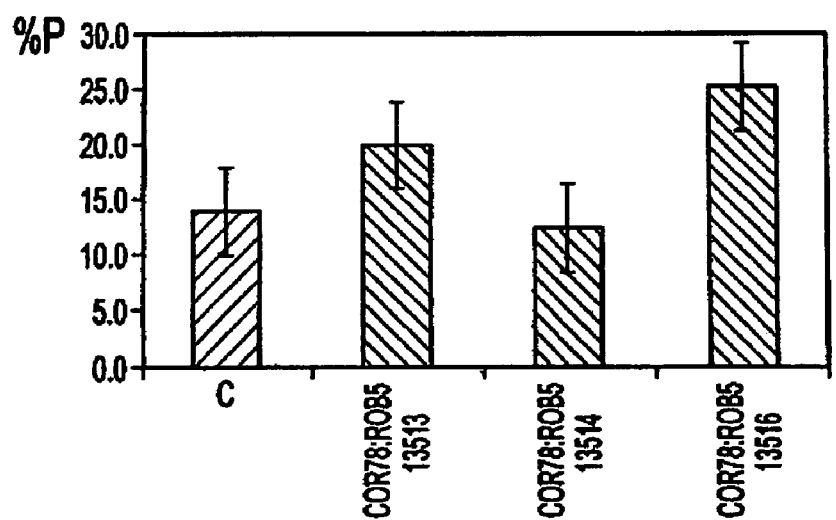
FIG. 30(b) shows average pod fill (% P) for trials at Nisku, AB (very stressed).

FIG. 30 illustrates average pod fill for COR78:ROB5 transformed plants compared to control plants at 'stressed' or 'very-stressed' sites. (a) graph shows average percentage pod fill (% P) for trials at Aberdeen, SK (stressed), and (b) graph shows average pod fill (% P) for trials at Nisku, AB (very stressed). Lines 13513 and 13516 exhibited significantly higher percentage pod fill at both stressed and severely stressed sites.

EXAMPLE 32

Advanced Maturity and Enhanced Root Development in Transformed Canola Lines

Figure 31A:
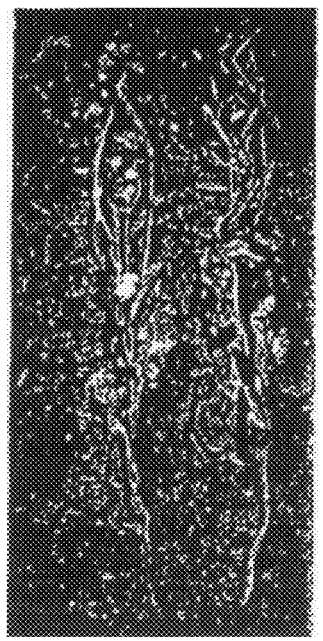
FIG. 31(a) illustrates enhanced maturity and root development in COR7:ROB5 transformed canola plants. The figure provides comparative photographs illustrating advanced maturity of canola transformed line 13516 (right) compared to a control plant (left) in the field at Wakaw, SK (stressed).
Figure 31B:
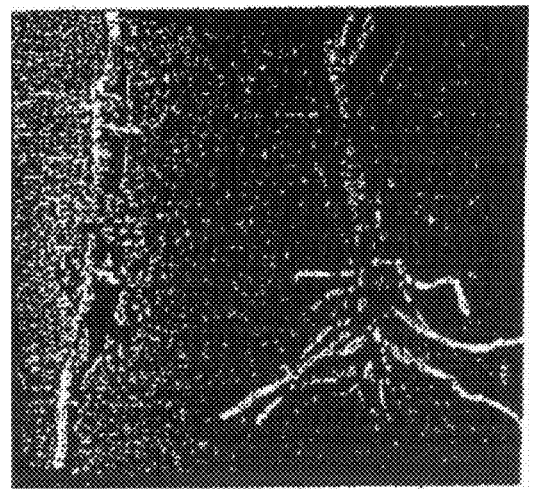
FIG. 31(b) provides comparative photographs showing root development of canola transformed line 13513 (right) compared to a control plant (left) at Wakaw, SK.

FIG. 31 illustrates enhanced maturity and root development in COR78:ROB5 transformed plants. (a) provides comparative photographs illustrating advanced maturity of canola transformed line 13516 (right) compared to a control plant (left) in the field at Wakaw, SK (stressed), and (b) provides comparative photographs showing root development of canola transformed line 13513 (right) compared to a control plant (left) at Wakaw, SK.

EXAMPLE 33

Enhanced Seed Yield for Transformed Canola at a Non-Stressed Site (Portage la Pairie, SK)

Figure 32:
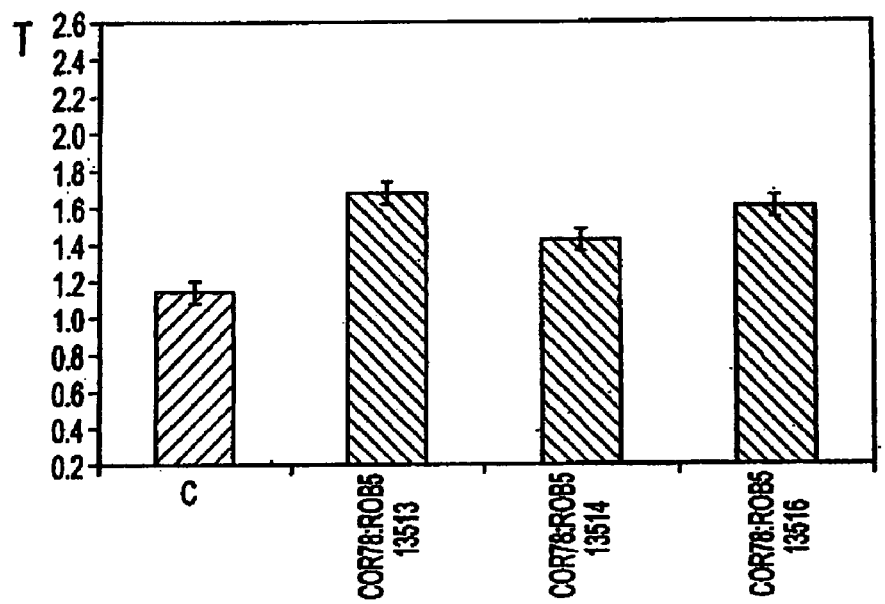
FIG. 32 illustrates a graph showing total yield and quality of seeds per plant (T in grams) for COR78:ROB5 transformed canola plants compared to control plants at a 'non-stressed' site (Portage la Prairie, MB).

FIG. 32 illustrates a graph showing total yield and quality of seeds per plant (T in grams) for COR78:ROB5 transformed plants compared to control plants at a 'non-stressed' site (Portage la Prairie). All three transformed lines 13513, 13514, and 13516 exhibited significantly higher yields of seed compared to control plants.

EXAMPLE 34

Enhanced Seed Yield for Transformed Canola at Stressed Sites (Aberdeen SK, and Saskatoon, SK)

Figure 33A:
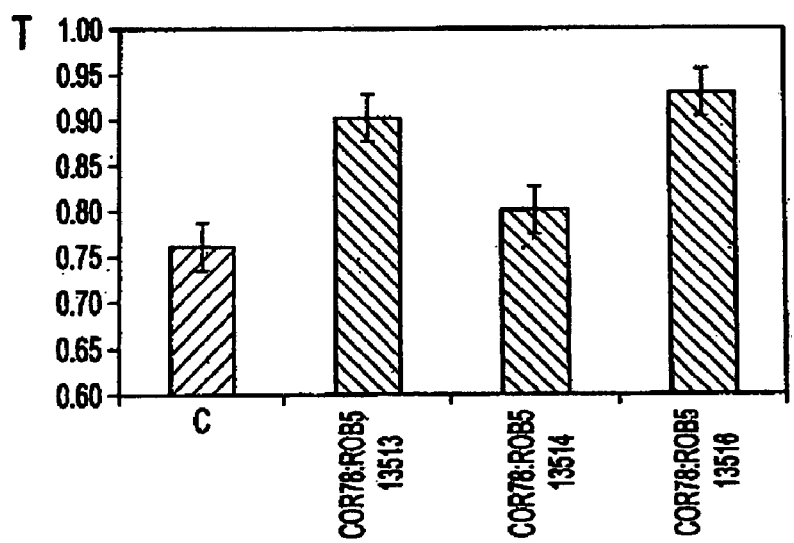
FIG. 33(a) illustrates total yield and quality of seeds for COR78:ROB5 transformed canola plants compared to control plants at 'stressed' sites. The graph shows total yield of seeds (T in grams) for control and transformed plants at Aberdeen, SK.
Figure 33B:
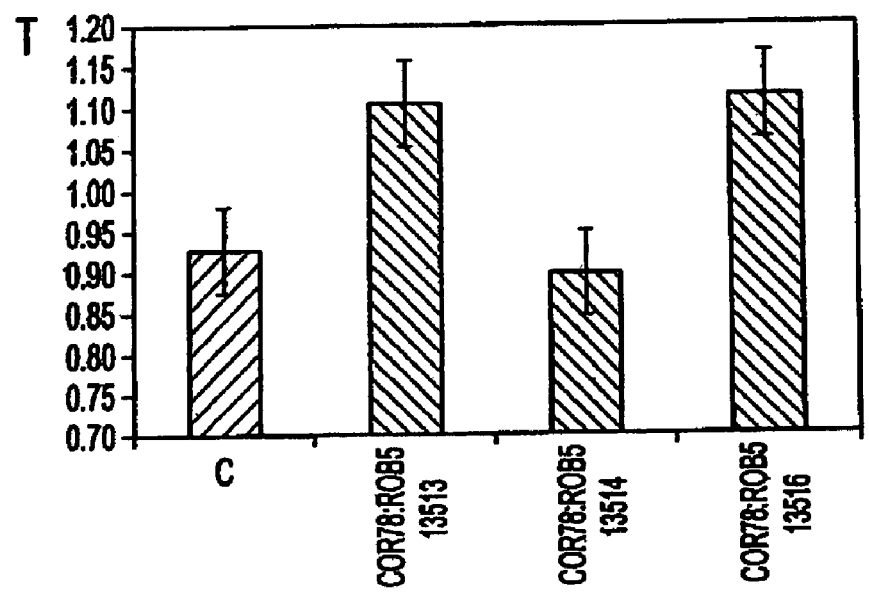
FIG. 33(b) shows total yield of seeds (T in grams) for control and transformed plants at Wakaw, SK.

FIG. 33 illustrates total yield and quality of seeds for COR78:ROB5 transformed plants compared to control plants at 'stressed' sites. (a) graph shows total yield of seeds (T in grams) for control and transformed plants at Aberdeen, SK, and (b) graph shows total yield of seeds (T in grams) for control and transformed plants at Wakaw, SK. Lines 13513 and 13516 shows particularly significant increases in total average yields per plant compared to control plants.

EXAMPLE 35

Enhanced Seed Quality with Increased Seed Size for Transgenic Canola Lines at Non-Stressed Sites (MacGregor, MB)

Figure 34:
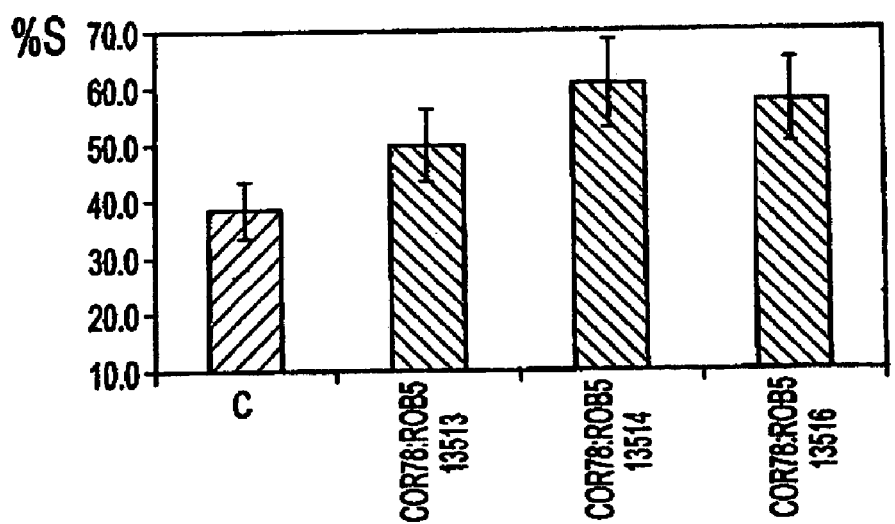
FIG. 34 illustrates the percentage number of seeds greater than 2.22 mm diameter (%S) for COR78:ROB5 transformed canola plants compared to control plants at a 'non-stressed' site (MacGregor, MB).

FIG. 34 illustrates the percentage number of seeds greater than 2.22 mm diameter (% S) for COR78:ROB5 transformed plants compared to control plants at a 'non-stressed' site (MacGregor, MB). All three transformed lines 13513, 13514, and 13516 exhibited significantly larger seeds compared to control plants.

EXAMPLE 36

Enhanced Seed Quality with Increased Seed Size for Transgenic Canola Lines at Stressed Sites (Wakaw, SK, and Aberdeen, SK)

Figure 35A:
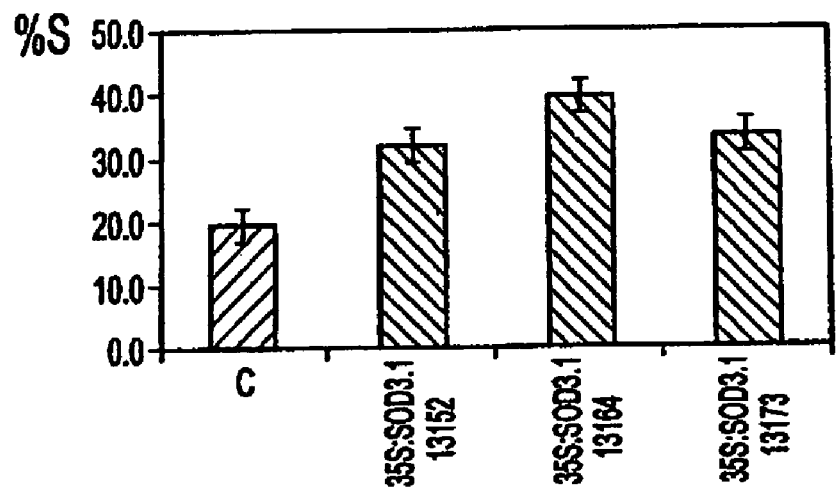
FIG. 35(a) illustrates the percentage number of seeds greater than a predetermined diameter (% S) for COR78:ROB5 transformed canola plants compared to control plants at 'stressed' sites. The graph shows the total percentage of seeds having a diameter greater than 2.22 mm harvested from plants at the Wakaw, SK site.
Figure 35B:
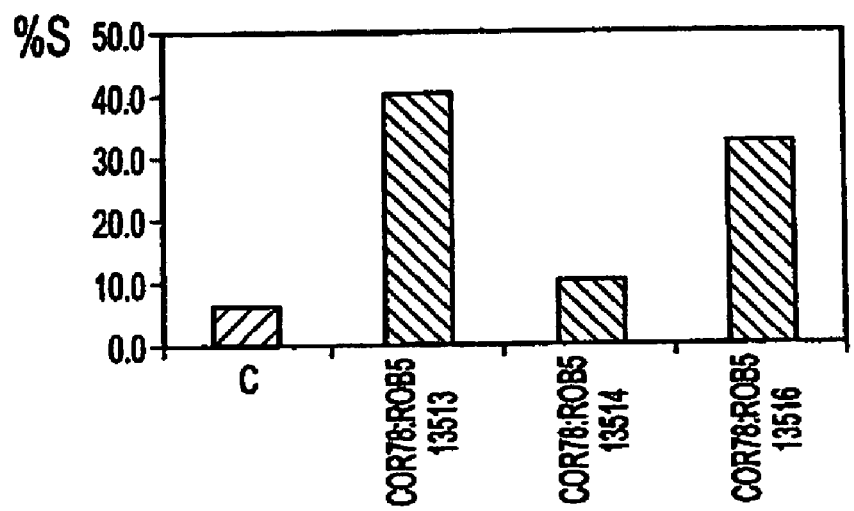
FIG. 35(b) shows the total percentage of seeds having a diameter greater than 2.00 mm harvested from plants at the Saskatoon, SK site.

FIG. 35 illustrates the percentage number of seeds greater than a predetermined diameter (% S) for COR78:ROB5 transformed plants compared to control plants at 'stressed' sites. (a) graph shows the total percentage of seeds having a diameter greater than 2.22 mm harvested from plants at the Wakaw, SK site, and (b) graph shows the total percentage of seeds having a diameter greater than 2.00 mm harvested from plants at the Saskatoon, SK site. All three transformed lines 13513, 13514, and 13516 exhibited significantly larger seeds compared to control plants at the Wakaw, SK site.

EXAMPLE 37

Enhanced Seed Quality and Increased Seed Weight for Transgenic Canola Lines at a Stressed site (Saskatoon, SK)

Figure 36A:
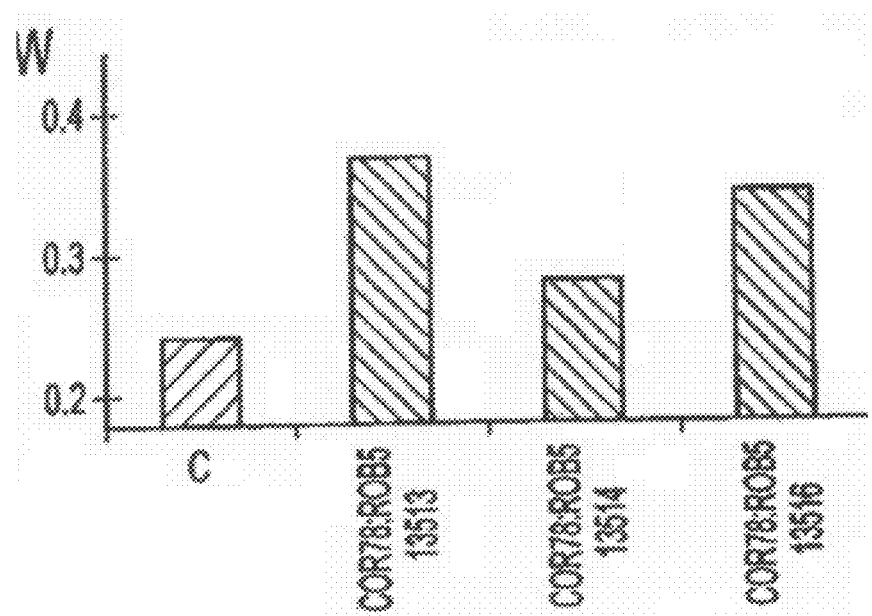
FIG. 36(a) provides a comparison of seeds harvested from control and COR78:ROB5 plants grown at a stressed site (Saskatoon. SK). The graph shows the 1000 Kernel Seed Weight W (in g) of seeds harvested from control and transformed canola plants.
Figure 36B:
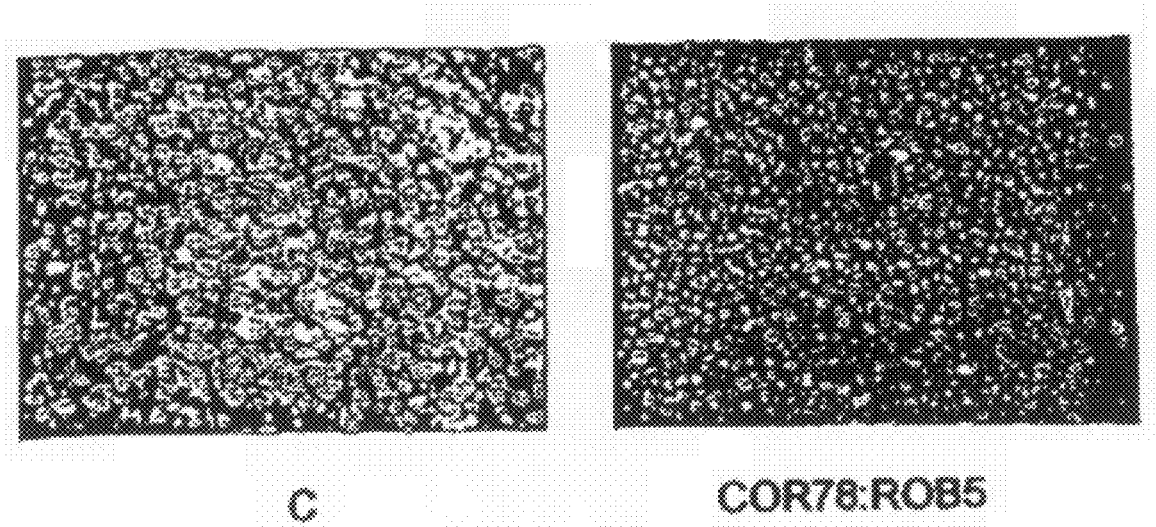
FIG. 36(b) provides comparative photographs of seeds derived from control (left) and COR78:ROB5 transformed plants (right). Note improved seed quality and maturity in seeds derived from transgenic plant.

FIG. 36 provides a comparison of seeds harvested from control and COR78:ROB5 plants grown at a stressed site (Saskatoon, SK). (a) graph shows the 1000 Kernel Seed Weight (g) of seeds harvested from control and transformed plants, and (b) provides comparative photographs of seeds derived from control (left) and COR78:ROB5 transformed plants (right). Note improved seed quality and maturity in seeds derived from transgenic plant.

EXAMPLE 38

Enhanced Germination and Seed Quality for Transformed Canola Lines Under Non-Salt Stressed and Salt Stressed Conditions FIG. 37 illustrates enhanced germination and seed quality of COR78:ROB5 transformed plants compared to control plants under both non salt stressed and salt stressed conditions. (a) graphs show percentage germination (% G) for control and transformed plants (mean 4 plates) over an 8 day period at stressed sites under conditions of no salt stress (ddH2O applied at 24° C.), and (b) graphs show percentage germination (% G) for control and transformed plants (mean 4 plates) over a 7 day period at stressed sites under conditions of salt stress (80 mM salt $KH_2PO_4/K_2HPO_4$ applied at 24° C.).

While the invention has been described with reference to particular preferred embodiments thereof, it will be apparent to those skilled in the art upon a reading and understanding of the foregoing that ROB5 genes and peptides encoded thereby, plants expressing corresponding ROB5 constructs, and plant products thereof, other than the specific embodiments illustrated are attainable, which nonetheless lie within the spirit and scope of the present invention. It is intended to include all such systems and methods, and equivalents thereof within the scope of the appended claims.

TABLE 1

Sequence pair distances of alignment.
Sequence pair distances of alignment.MEG, using J.
Hein method with PAM250 residue weight table.
Thursday, Apr. 04, 2002 2:26 PM

| | | \multicolumn{13}{c}{Percent Identity} | |
| --- | --- | --- | --- | --- | --- | --- | --- | --- | --- | --- | --- | --- | --- | --- | --- |
| | | 1 | 2 | 3 | 4 | 5 | 6 | 7 | 8 | 9 | 10 | 11 | 12 | 13 | |
| Divergence | 1 | | 24.7 | 29.5 | 22.5 | 27.2 | 28.0 | 27.8 | 29.5 | 30.6 | 26.6 | 26.1 | 23.5 | 25.5 | 1 Rob5.pro |
| | 2 | 100.0 | | 25.3 | 24.7 | 51.9 | 17.5 | 55.7 | 22.6 | 23.1 | 25.9 | 19.7 | 16.8 | 20.2 | 2 white birch.PRO |
| | 3 | 100.0 | 100.0 | | 60.3 | 29.0 | 47.8 | 26.2 | 22.0 | 23.0 | 88.2 | 23.4 | 29.6 | 20.3 | 3 wheat.PRO |
| | 4 | 100.0 | 100.0 | 55.9 | | 27.9 | 46.7 | 23.8 | 18.3 | 21.8 | 62.8 | 22.2 | 30.2 | 18.5 | 4 rice.PRO |
| | 5 | 100.0 | 74.8 | 100.0 | 100.0 | | 26.6 | 48.8 | 23.3 | 26.0 | 27.8 | 19.0 | 22.7 | 20.1 | 5 *Arabidopsis2*.PRO |
| | 6 | 100.0 | 100.0 | 86.0 | 89.1 | 100.0 | | 21.9 | 21.3 | 21.7 | 48.8 | 21.1 | 28.6 | 17.7 | 6 *Brassica napus*.PRO |
| | 7 | 100.0 | 65.8 | 100.0 | 100.0 | 83.0 | 100.0 | | 21.3 | 24.8 | 27.3 | 21.4 | 20.8 | 16.4 | 7 carrot.PRO |
| | 8 | 100.0 | 100.0 | 100.0 | 100.0 | 100.0 | 100.0 | 100.0 | | 28.2 | 23.1 | 30.0 | 25.4 | 33.1 | 8 cotton.PRO |
| | 9 | 100.0 | 100.0 | 100.0 | 100.0 | 100.0 | 100.0 | 100.0 | 100.0 | | 21.8 | 20.2 | 18.7 | 24.0 | 9 *Glycine max*.PRO |
| | 10 | 100.0 | 100.0 | 12.9 | 51.0 | 100.0 | 83.2 | 100.0 | 100.0 | 100.0 | | 24.0 | 31.0 | 21.5 | 10 Hva-1.pro |
| | 11 | 100.0 | 100.0 | 100.0 | 100.0 | 100.0 | 100.0 | 100.0 | 100.0 | 100.0 | 100.0 | | 26.1 | 32.2 | 11 *Morus bombycis*.PRO |
| | 12 | 100.0 | 100.0 | 100.0 | 100.0 | 100.0 | 100.0 | 100.0 | 100.0 | 100.0 | 100.0 | 100.0 | | 20.7 | 12 *Riccia fluitans*.PRO |
| | 13 | 100.0 | 100.0 | 100.0 | 100.0 | 100.0 | 100.0 | 100.0 | 100.0 | 100.0 | 100.0 | 100.0 | 100.0 | | 13 *Arabidopsis*.PRO |
| | | 1 | 2 | 3 | 4 | 5 | 6 | 7 | 8 | 9 | 10 | 11 | 12 | 13 | |

TABLE 2

Transformation vector construction using Rob-5.

| Name or Construct (Promoter: Gene) | vector | Promoter (Restriction Sites) | Gene (Restriction Sites) |
| --- | --- | --- | --- |
| 35S:ROB5 | Bin19 | 35S (Hind III, Xba I) | ROB5 (BamH I, Kpn I) |
| COR78:ROB5 | PHS737 | COR78 (Sal I, BamH I) | ROB5 (BamH I, Kpn I) |
| 35S:RUB5::COR15:PPA | PHs737 | 35S (Hind III, Xba I) COR15 (Xho, Sac I) | ROB5 (BamH I, Kpn I) PPA (Sac I, Kpn I) |

TABLE 3

Transgenic lines of canola, flax and potato expressing Rob-5 that showed enhanced tolerance to multiple stresses (frost, heat, and drought). In addition, the selected transgenic lines demonstrated increased or improved germination, emergence (seedling vigour), plant height, earlier maturity (days to flower), and yield (seed weight harvested).

| | Transgenic Line | Frost Tolerance | Heat Tolerance | Drought Tolerance | Germination | Emergence | Plant Height | Days to Flower | Seed Weight |
| --- | --- | --- | --- | --- | --- | --- | --- | --- | --- |
| 35S:ROB5 | Potato | | | | | | | | |
| | 13646 | | X | | | | X | | X |
| | 13637 | | X | X | | X | X | | |
| COR78:ROB5 | Canola | | | | | | | | |
| | 13513 | X | X | | X | | | X | |
| | Flax | | | | | | | | |
| | 13847 | X | | | | X | | X | |
| | 13850 | X | | X | | | | | |

TABLE 3-continued

Transgenic lines of canola, flax and potato expressing Rob-5 that showed enhanced tolerance to multiple stresses (frost, heat, and drought). In addition, the selected transgenic lines demonstrated increased or improved germination, emergence (seedling vigour), plant height, earlier maturity (days to flower), and yield (seed weight harvested).

| Transgenic Line | Frost Tolerance | Heat Tolerance | Drought Tolerance | Germination | Emergence | Plant Height | Days to Flower | Seed Weight |
|---|---|---|---|---|---|---|---|---|
| Potato | | | | | | | | |
| 13665 | X | X | | | X | | | X |
| 13669 | X | | X | | X | X | | X |

---

The invention claimed is:

1. An isolated polynucleotide comprising a nucleotide sequence characterized in that said nucleotide sequence is selected from a group consisting of a) a nucleotide sequence as shown in SEQ ID NO: 1 and b) a nucleotide sequence encoding a polypeptide having the amino acid seguence as shown in SEQ ID NO: 2 wherein expression of said isolated nucleotide sequence in a transgenic plant increases an abiotic stress tolerance in the transgenic plant compared to an untransformed plant of the same species.

2. The isolated polynucleotide of claim 1, characterized in that expression of said nucleotide sequence confers on said transgenic plant an increased tolerance to the abiotic stress selected from the group consisting of heat, cold, frost, and drought as compared to an untransformed plant of the same species.

3. The isolated polynucleotide of claim 1, characterized in that expression of said nucleotide sequence also confers on said transgenic plant faster germination, faster seedling emergence or an earlier maturity as compared to an untransformed plant of the same species.

4. The isolated polynucleotide according to claim 1 characterized in that the nucleotide sequence is obtained from a bromegrass plant.

5. A DNA expression cassette characterized in that said DNA expression cassette comprises the polynucleotide according to claim 1, operably linked to a promoter.

6. A construct characterized in that the construct comprises the DNA expression cassette according to claim 5.

7. The construct according to claim 6 characterized in that said promoter is selected from the group consisting of a constitutive promoter, an inducible promoter, an organ specific promoter, and a stress inducible promoter.

8. A plant cell characterized in that said plant cell is transformed with the construct according to claim 6 and said plant cell expresses said nucleotide sequence.

9. A transgenic plant characterized in that said tranagenic plant is obtained from regeneration of said plant cell according to claim 8.

10. The tranagenic plant according to claim 9 characterized in that said transgenic plant is selected from a species of grain producing crop, a fruit or vegetable species, and a horticultural species.

11. The transgenic plant according to claim 10 characterized in that said transgenic plant is a species selected from the group consisting of canola, flax, and potato.

12. A method of genetically modifying a plant, characterized in that the method comprises the steps of:
  (a) introducing into a plant cell capable of being transformed a construct comprising, in addition to DNA sequences required for transformation and selection in plants, the polynucleotide according to claim 1, operably linked to a promoter;
  (b) regenerating a transgenic plant from the transformed plant cell wherein the transformed plant contains said nucleotide sequence; and
  (c) expressing the nucleotide sequence in cells of the transformed plant.

13. The method according to claim 12 characterized in that said plant exhibits an increased tolerance to an abiotic stress compared to an untransformed plant of the same species.

14. The method according to claim 13 characterized in that said plant exhibits an increased tolerance to the abiotic stress selected from the group consisting of heat, cold; frost, and drought, as compared to an untransformed plant of the same species.

15. The method according to claim 12 characterized in that said plant exhibits faster germination, faster seedling emergence or an earlier maturity as compared to an untransformed plant of the same species.

16. The method according to claim 12 characterized in that said nucleotide sequence is oriented in a sense direction relative to the promoter.

* * * * *